US011590102B2

(12) United States Patent
Pimentel et al.

(10) Patent No.: US 11,590,102 B2
(45) Date of Patent: *Feb. 28, 2023

(54) ANTI-METHANOGENIC LOVASTATIN ANALOGS OR DERIVATIVES AND USES THEREOF

(71) Applicant: CEDARS-SINAI MEDICAL CENTER, Los Angeles, CA (US)

(72) Inventors: Mark Pimentel, Los Angeles, CA (US); Vince Wacher, Rockville, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 252 days.

This patent is subject to a terminal disclaimer.

(21) Appl. No.: 16/915,427

(22) Filed: Jun. 29, 2020

(65) Prior Publication Data
US 2021/0015790 A1    Jan. 21, 2021

Related U.S. Application Data

(63) Continuation of application No. 15/560,145, filed as application No. PCT/US2016/025214 on Mar. 31, 2016, now Pat. No. 10,736,871.

(60) Provisional application No. 62/141,413, filed on Apr. 1, 2015.

(51) Int. Cl.
| | | |
|---|---|---|
| A61K 31/366 | (2006.01) | |
| A61K 45/06 | (2006.01) | |
| A61P 1/14 | (2006.01) | |
| A61K 9/00 | (2006.01) | |
| A61K 9/24 | (2006.01) | |
| A61K 9/16 | (2006.01) | |

(52) U.S. Cl.
CPC .......... *A61K 31/366* (2013.01); *A61K 9/0053* (2013.01); *A61K 45/06* (2013.01); *A61P 1/14* (2018.01); *A61K 9/167* (2013.01); *A61K 9/209* (2013.01); *G01N 2800/065* (2013.01)

(58) Field of Classification Search
CPC .... A61K 31/366; A61K 9/0053; A61K 45/00; A61P 1/14
See application file for complete search history.

(56) References Cited

U.S. PATENT DOCUMENTS

| | | | |
|---|---|---|---|
| 225,202 | A | 3/1880 | Wylie |
| 5,225,202 | A | 7/1993 | Hodges et al. |
| 5,232,946 | A | 8/1993 | Humaus et al. |
| 5,447,850 | A | 9/1995 | McCann |
| 5,840,332 | A | 11/1998 | Lerner et al. |
| 5,889,038 | A | 3/1999 | Lencer et al. |
| 5,977,175 | A | 11/1999 | Lin |
| 5,985,907 | A | 11/1999 | Wolin et al. |
| 6,036,950 | A | 3/2000 | Baker et al. |
| 6,201,014 | B1 | 3/2001 | Gardiner |
| 6,299,774 | B1 | 10/2001 | Ainsworth et al. |
| 6,328,959 | B1 | 12/2001 | Kayar et al. |
| 6,368,591 | B2 | 4/2002 | Chen et al. |
| 6,495,567 | B1 | 12/2002 | Lencer et al. |
| 6,558,708 | B1 | 5/2003 | Lin |
| 6,562,629 | B1 | 5/2003 | Lin et al. |
| 6,805,852 | B2 | 10/2004 | Lin et al. |
| 6,861,053 | B1 | 3/2005 | Lin et al. |
| 9,066,962 | B2 | 6/2015 | Pimentel et al. |
| 9,192,618 | B2 | 11/2015 | Pimentel et al. |
| 9,289,418 | B2 | 3/2016 | Pimentel et al. |
| 9,358,245 | B2 | 6/2016 | Pimentel et al. |
| 9,744,208 | B2 | 8/2017 | Pimentel et al. |
| 9,845,511 | B2 | 12/2017 | Pimentel et al. |
| 9,956,292 | B2 | 5/2018 | Pimentel et al. |
| 10,226,505 | B2 | 3/2019 | Pimentel et al. |
| 10,328,151 | B2 | 6/2019 | Pimentel et al. |
| 10,519,515 | B2 | 12/2019 | Pimentel et al. |
| 10,668,159 | B2 | 6/2020 | Pimentel et al. |
| 10,688,149 | B2 | 6/2020 | Pimentel et al. |
| 10,736,871 | B2 * | 8/2020 | Pimentel .............. A61K 9/0053 |
| 11,235,022 | B2 | 2/2022 | Pimentel et al. |
| 11,344,501 | B2 | 5/2022 | Pimentel et al. |
| 2002/0028269 | A1 | 3/2002 | Verrips |
| 2002/0039599 | A1 | 4/2002 | Lin et al. |
| 2006/0057197 | A1 | 3/2006 | Han et al. |

(Continued)

FOREIGN PATENT DOCUMENTS

| | | |
|---|---|---|
| AU | 2003273141 | 8/2009 |
| AU | 2014239164 | 9/2015 |

(Continued)

OTHER PUBLICATIONS

Alander et al., The effect of probiotic strains on the microbiota of the Simulator of the Human Intestinal Microbial Ecosystem (SHIME), Int. J. Food Microbiol., 1999, 46(1):71-79.
Bakker-Arkema et al., Safety Profile of Atorvastatin-Treated Patients With Low LDL-Cholesterol Levels, Atherosclerosis, 2000, 149(1): 123-129.
Basseri et al., Intestinal Methane Production in Obese Individuals Is Associated with a Higher Body Mass Index. Gastroenterology & Hepatology 2012; 8(1): 22-28.
Bentley et al., The microflora of the human ileum and intrabdominal colon: results of direct needle aspiration at surgery and evaluation of the technique, J Lab Clin Med., 1972, 79(3):421-429.
Bjorneklett et al., Bacterial overgrowth in jejunal and ileal disease, Scand J Gastroenterol., 1983, 18(2):289-298.
Black et al., An Overview of the Clinical Safety Profile of Atorvastatin (Lipitor), A New HMG-CoA Reductase Inhibitor, Archives of Internal Medicine, 1998, 158(6):577-584.

(Continued)

*Primary Examiner* — Kevin E Weddington
(74) *Attorney, Agent, or Firm* — Nixon Peabody LLP; Linda B. Huber

(57) ABSTRACT

The present invention relates to, in part, methods for the treatment of methanogen-associated disorders such as, for example, Irritable Bowel Syndrome (IBS) using at least one anti-methanogenic lovastatin analog or derivative. In addition, modified-release formulations comprising at least one anti-methanogenic lovastatin analog or derivative are provided which release the anti-methanogenic lovastatin analog or derivative in the gastrointestinal tract.

12 Claims, 8 Drawing Sheets

(56) References Cited

U.S. PATENT DOCUMENTS

| | | |
|---|---|---|
| 2006/0111436 A1 | 5/2006 | Griffin |
| 2006/0246045 A1 | 11/2006 | Pimentel et al. |
| 2007/0280949 A1 | 12/2007 | Alfa |
| 2008/0182291 A1 | 7/2008 | Pimentel et al. |
| 2009/0048175 A1 | 2/2009 | Shailubhai et al. |
| 2009/0233888 A1 | 9/2009 | Lin |
| 2009/0246177 A1 | 10/2009 | Horn et al. |
| 2010/0048595 A1 | 2/2010 | Gordon et al. |
| 2010/0005173 A1 | 3/2010 | Penhasi et al. |
| 2010/0172874 A1 | 7/2010 | Turnbaugh et al. |
| 2010/0184624 A1 | 7/2010 | Samuel et al. |
| 2012/0219527 A1 | 8/2012 | Perdok et al. |
| 2014/0228431 A1 | 8/2014 | Pimentel et al. |
| 2014/0271561 A1 | 9/2014 | Pimentel et al. |
| 2016/0038562 A1 | 2/2016 | Pimentel et al. |
| 2016/0045604 A1 | 2/2016 | Pimentel et al. |
| 2016/0244813 A1 | 8/2016 | Pimentel et al. |
| 2018/0071359 A1 | 3/2018 | Pimentel et al. |
| 2018/0119206 A1 | 5/2018 | Pimentel et al. |
| 2018/0289667 A1 | 10/2018 | Pimentel et al. |
| 2018/0289816 A1 | 10/2018 | Pimentel et al. |
| 2019/0142895 A1 | 5/2019 | Pimentel et al. |
| 2019/0328885 A1 | 10/2019 | Pimentel et al. |
| 2020/0087711 A1 | 3/2020 | Pimentel et al. |
| 2020/0323781 A1 | 10/2020 | Pimentel et al. |
| 2020/0360468 A1 | 11/2020 | Pimentel et al. |
| 2020/0390742 A1 | 12/2020 | Wacher et al. |

FOREIGN PATENT DOCUMENTS

| | | |
|---|---|---|
| AU | 2015301596 | 2/2017 |
| BR | 11 2015 022825-9 A2 | 11/2017 |
| BR | 11 2017 002761-5 A2 | 12/2017 |
| CA | 2486585 | 12/2003 |
| CA | 2903493 | 9/2014 |
| CA | 2955666 | 2/2016 |
| CA | 2903493 C | 5/2022 |
| CN | 1681522 | 10/2005 |
| CN | 101312716 A | 11/2008 |
| CN | 102497786 | 6/2012 |
| CN | 103142552 A | 6/2013 |
| CN | 103230593 A | 8/2013 |
| CN | 105208861 | 12/2015 |
| CN | 106687107 | 5/2017 |
| CN | 106687107 B | 12/2020 |
| EP | 1 505 989 | 2/2005 |
| EP | 1 609 852 | 12/2005 |
| EP | 2 251 017 | 11/2010 |
| EP | 2 967 060 | 1/2016 |
| EP | 3179983 | 6/2017 |
| EP | 3277274 | 2/2018 |
| GB | 423083 | 1/1935 |
| GB | 2 338 244 | 12/1999 |
| HK | 1214752 | 8/2016 |
| HK | 1238153 | 4/2018 |
| IL | 250568 B | 9/2021 |
| JP | 60-133852 | 7/1985 |
| JP | 03-275630 | 12/1991 |
| JP | 08-310960 | 11/1996 |
| JP | 2005-526861 | 9/2005 |
| JP | 2006504686 | 2/2006 |
| JP | 2007512287 | 5/2007 |
| JP | 2016-516717 | 6/2016 |
| JP | 2017-528516 A | 9/2017 |
| JP | 2017528516 | 9/2017 |
| JP | 2019-31501 | 2/2019 |
| JP | 6667526 B2 | 3/2020 |
| KR | 20170041769 | 4/2017 |
| KR | 102425303 B1 | 7/2022 |
| MX | 2015012444 | 10/2016 |
| MX | 2017001971 | 9/2017 |
| MX | 2017001971 A | 3/2020 |
| RU | 2017106896 | 9/2018 |
| RU | 2697851 | 8/2019 |
| WO | WO 2000033821 | 6/2000 |
| WO | WO 2001/011077 | 2/2001 |
| WO | WO 2001/032162 | 5/2001 |
| WO | WO 2001/034123 | 5/2001 |
| WO | WO 03000180 | 1/2003 |
| WO | WO 2003/100023 | 12/2003 |
| WO | WO 2004/021972 | 3/2004 |
| WO | WO 2005/058861 | 6/2005 |
| WO | WO 2005/115380 | 12/2005 |
| WO | WO 2006/102350 | 9/2006 |
| WO | WO 2008/044236 | 4/2008 |
| WO | WO 2010/088633 | 8/2010 |
| WO | WO 2011/103123 | 8/2011 |
| WO | WO 2012/124973 | 9/2012 |
| WO | WO 2014110090 | 7/2014 |
| WO | WO 2014/152754 | 12/2014 |
| WO | WO 2016/025762 | 2/2016 |
| WO | WO 2016/161085 | 10/2016 |
| WO | WO 2017223177 | 12/2017 |
| ZA | 201700566 | 7/2018 |

OTHER PUBLICATIONS

Bond Jr. et al., Investigation of small bowel transit time in man utilizing pulmonary hydrogen (H2) measurements, J Lab Clin Med., 1975, 85(4):546-555.

Camilleri et al., Efficacy and safety of alosetron in women with irritable bowel syndrome: a randomised, placebo-controlled trial, Lancet., 2000, 355(9209):1035-1040.

Cann et al., Irritable bowel syndrome: relationship of disorders in the transit of a single solid meal to symptom patterns, Gut, 1983, 24(5):405-411.

Castiglione et al. Orocecal transit time and bacterial overgrowth in patients with Crohn's disease, J Clin Gastroenterol., 2000, 31(1):63-66.

Chang et al., Increased accuracy of the carbon-14 D-xylose breath test in detecting small-intestinal bacterial overgrowth by correction with the gastric emptying rate, Eur. J. Nucl. Med., 1995, 22(10):1118-1122.

Charteris et al., Antibiotic susceptibility of potentially probiotic *Lactobacillus* species, J. Food Prot., 1998, 61(12):1636-1643.

Chatterjee et al., The degree of breath methane production in IBS correlates with the severity of constipation, Am. J. Gastroenterology 2007, 102: 837-841.

Chaucheryras et al., In vitro $H_2$ utilization by ruminal aceto genic bacterium cultivated alone or in association with an archaea methanogen is stimulated by a probiotic strain of *Saccharomy ces cerevisiae*, Appl Environ Microbiol, 1995, 61(9):3466-3467.

Collins et al., Stress, inflammation and the irritable bowel syndrome, Canadian Journal of Gastroenterology. 1999, 13 Suppl:47A-49A.

Corazza et al., Prevalence and consistency of low breath H2 excretion following lactulose ingestion, Possible implications for the clinical use of the H2 breath test, Dig. Dis. Sci., 1993, 38(11):2010-2016.

De Boissieu et al., Small-Bowel bacterial overgrowth in children with chronic diarrhea, abdominal pain, or both, J Pediatr., 1996, 128(2):203-207.

Dellert et al., The $^{13}$C-xylose breath test for the diagnosis of small bowel bacterial overgrowth in children, J. Pediatr. Gastroenterol. Nutr. 1997, 25(2):153-158.

Drossman et al., Bowel patterns among subjects not seeking health care. Use of a questionnaire to identify a population with bowel dysfunction, Gastroenterology., 1982, 83(3):529-534.

Dobson et al., The effect of oleic acid on the human ileal brake and its implications for small intestinal transit of tablet formulations, Pharm. Res., 1999, 16(1):92-96.

Engels et al., Symptomless Colonisation by Clostridium Difficile and Risk of Diarrhoea, The Lancet, 1998, 351:9117, p. 1733.

Evonik Industries, Eudragit, 2015, 16 Pages, Retrieved from the internet: http://eudragit.evonik.com/sites/lists/HN/Documents/evonik-brochure-eudragit-EN.pdf on Jul. 13, 2016.

Fass. et al., Evidence and consensus-based practice guidelines for the diagnosis of irritable bowel syndrome, Arch Intern Med., 2001, 161(17):2081-2088.

(56) References Cited

OTHER PUBLICATIONS

Fiedorek et al., Breath methane production in children with constipation and encoparesis, J Pediatr Gastroenterol., 1990, 10(4):473-477.
Funayama et al., Monitoring and antibacterial treatment for postoperative bacterial overgrowth in Crohn's disease, Dis Colon Rectum., 1999, 42(8):1072-1077.
Galatola et al., Diagnosis of bacterial contamination of the small intestine using the 1g [14C] xylose breath test in various gastrointestinal diseases, Menerva Gastroenterologic Dietologica, 1991, 37(3):169-175, (Abstract in English).
Gardiner et al., Development of a probiotic cheddar cheese containing human-derived Lactobacillus paracasei strains, Appl. Environ. Microbiol., 1998, 64(6):2192-2199.
Ghoshal et al., Irritable bowel syndrome and small intestinal bacterial overgrowth: Meaningful association or unnecessary hype. World Journal of Gastroenterology, 2014, 20(10):2482-2491.
Gorbach, S.L., Intestinal Microflora, Gastroenterology, 1971, 60(6):1110-1129.
Grundy, D., Mechanisms for the symptoms of irritable bowel disease-possible role of vagal afferents, In, Neurogastroenterology from the Basics to the Clinics. H-J Drammer and MV Singer, Editors, Klumer Academic Publishers, Boston, 2000, pp. 659-663.
Hoeg et al., Effects of Combination Cholestyramine-Neomycin Treatment on Plasma Lipoprotein Concentrations In Type II Hyperlipoproteinemia, American Journal of Cardiology, 1985; 55(11):1282-1286.
Hoshino et al., Maldigestion/Malabsorption in the Various Gastrointestinal and Liver Diseases. Results of Breath Hydrogen and Methane Analysis, Digestion & Absorption, 1998, 21(1):55-60.
Hutchinson et al., Scintigraphic measurement of ieocaecal transit in irritable bowel syndrome and chronic idiopathic constipation, Gut, 1995, 36(4):585-589.
Hwang et al., Evaluating Breath Methane as a Diagnostic Test for Constipation-Predominant IBS. Dig Dis Sci 2010, 55(2): 398-403.
Joseph Jr., et al., Breath testing: diseased versus normal patients, J Pediatr Gastroenterol., 1988, 7(5):787-788.
Kang et al., Anti-Obesity Drugs: A Review about Their Effects and Safety. Diabetes Metab J, 2012, 36:13-25.
Kehrer et al., Modulation of Irinotecan-Induced Diarrhea by Cotreatment With Neomycin in Cancer Patients. Clinical Cancer Research, 2001, 7(1), pp. 1136-1141.
Kerlin et al., Breath hydrogen testing in bacterial overgrowth of the small intestine, Gastroenterology, 1988, 95(4):982-988.
Kim et al., Methanobrevibacter smithii Is the Predominant Methanogen in Patients with Constipation-Predominant IBS and Methane on Breath. Digestive Diseases and Sciences 2012, 57(12): 3213-3218.
King et al., Breath tests in the diagnosis of small intestinal bacterial overgrowth, Crit. Rev. Lab. Sci., 1984, 21(3):269-281.
King et al., Comparison of the 1-gram [14C]xylose, 10-gram lactulose-H2, and 80 gram glucose-H2 breath tests in patients with small intestine bacterial overgrowth, Gastroenterology, 1986, 91(6):1447-1451.
King et al., Abnormal colonic fermentation in irritable bowel syndrome, Lancet, 1998, 352(9135):1187-1189.
Koide et al., Quantitative analysis of bowel gas using plain abdominal radiograph in patients with irritable bowel syndrome, Am J Gastroenterol, 2000, 92(7):1735-1741.
Kontula et al., The effect of lactose derivatives on intestinal lactic acid bacteria, J. Dairy Sci., 1999, 82(2):249-256.
Kruis et al., A diagnostic score for the irritable bowel syndrome, Gastroenterology, 1984, 87(1):1-7.
Kumar et al., The irritable bowel syndrome: a paroxysmal motor disorder, Lancet., 1985, 2(8462):973-977.
Kunkel et al., Methane on Breath Testing is Associated with Constipation: A systematic review and Meta-analysis. Dig Dis Sci, 2011, 56(6):1612-1618.
Levitt et al., Hydrogen and methane production in man, Ann NY Acad Sci., 1968, 150(1):75-81.
Lewindon et al., Bowel dysfunction in cystic fibrosis: importance of breath testing, J. Pediatr. Child Health, 1998, 34(1):79-82.
Lin et al., Intestinal transit is more potently inhibited by fat in the distal (ileal brake) than in the proximal (jejunal brake) gut, Dig. Dis. Sci., 1997, 42(1):19-25.
Lin et al., Jejunal brake: inhibition of intestinal transit by fat in the proximal small intestine, Dig. Dis. Sci., 1996, 41(2):326-329.
Low et al., A Combination of Rifaximin and Neomycin Is Most Effective in Treating Irritable Bowel Syndrome Patients with Methane on Lactulose Breath Test. J Clin Gastroenterol, 2010, 44:547-550.
Mathur et al., Intestinal *Methanobrevibacter smithii* but Not Total Bacteria is Related to Diet-Induced Weight Gain in Rats. Obesity Journal 2013; 21(4):748-754.
Melcher et al., Methane production and bowel function parameters in healthy subjects on low-and high fiber diets, Nutrition and Cancer, 1991, 16(2):85-92.
Miller et al., Inhibition of Growth of Methane-Producing Bacteria of the Ruminant Forestomach by Hydroxymethylglutaryl-SCoA Reductase Inhibitors. J Dairy Sci, 2001, 84:1445-1448.
McKay et al., Methane and hydrogen production by human intestinal anaerobic bacteria, Acta Pathol Microbiol Immunol Scand [B], 1982, 90(3):257-260.
McKay et al., Methane excretion in man—a study of breath, flatus and faeces, Gut, 1983, 26(1):69-74.
The Merck Index (11th Edition), 1989, Entry 5225, p. 844.
Naidu et al., Probiotic spectra of lactic acid bacteria, Crit. Rev. Food Sci. Nutr., 1999, 38(1):13-126.
Nayak et al., Metronidazole relieves symptoms in irritable bowel syndrome: the confusion with so-called 'chronic amebiasis', Indian J Gastroenterol, 1997, 16(4):137-139.
Neal et al., Prevalence of gastrointestinal symptoms six months after bacterial gastroenteritis and risk facts for development of the irritable bowel syndrome: postal survey of patients, BMJ, 1997, 314(7083):779-782.
Nguyen et al., Diarrhea Caused by Enterotoxigenic Bacteroides Fragilis in Children Less Than 5 Years of Age in Hanoi, Vietnam, Anaerobe, 2005, 11:1-2, pp. 109-114.
Nichols et al., Ileal microflora in surgical patients, J Urol, 1971, 105(3):351-353.
Niedzielin et al., A controlled, double-blind, randomized study on the efficacy of Lactobacillus plantarum 299V in patients with irritable bowel syndrome, Euro. J. of Gastroenterology & Hepatology, 2001, vol. 13(10), pp. 1143-1147.
Nobaek et al., Alteration of intestinal microflora is associated with reduction in abdominal bloating and pain in patients with irritable bowel syndrome, Am. J. Gastroenterology, 2000, 95, 1231-1238.
Novick et al., A randomized, double-blind, placebo-controlled trial of tegaserod in female patients suffering from irritable bowel syndrome with constipation, Aliment. Pharmacol. Ther. 2002, 16: 1877-1888.
Olesen et al., Efficacy, safety, and tolerability of fructooligosaccharides in the treatment of irritable bowel syndrome, Am. J. Clin. Nutr., 2000; 72: 1570-1575.
Peled et al., Factors affecting methane production in humans. Gastrointestinal diseases and alterations of colonic flora, Dig Dis Scr., 1987, 32(3):267-271.
Pimentel et al., Eradication of small intestinal bacterial overgrowth reduces symptoms of irritable bowel syndrome, Am J Gastroenterol., 2000, 95(12):3503-3506.
Pimentel et al., Methane, a gas produced by enteric bacteria, slows intestinal transit and augments small intestinal contractile activity, Am. J. Physiol. Gastrointest. Liver Physiol., 2006, 290: G1089-G1095.
Pimentel et al., Neomycin improves constipation-predominant irritable bowel syndrome in a fashion that is dependent on the presence of methane gas: Subanalysis of a double-blind randomized controlled study, Dig. Dis. Science, 2006, 51: 1297-1301.
Plaut et al., Studies of intestinal microflora. 3. The microbial flora of human small intestinal mucosa and fluids, Gastroenterology, 1967, 53(6):868-873.

(56) References Cited

OTHER PUBLICATIONS

Quigley et al., Small Intestinal Bacterial Overgrowth: Roles of Antibiotics, Prebiotics, and Probiotics. Gastroenterology, 2006, 130:S78-S90.
Read et al., Simultaneous measurement of gastric emptying, small bowel residence and colonic filling of a solid meal by the use of the gamma camera, Gut, 1986, 27(3):300-308.
Rhodes et al., The lactulose hydrogen breath test as a diagnostic test for small bowel bacterial overgrowth, Scand J Gastroenterol, 1979, 14(3):333-336.
Riordan et al., The lactulose breath hydrogen test and small intestinal bacterial overgrowth, Am. J. Gastroentrol., 1996, 91(9):1795-1803.
Rooks et al., SU1940, Methanobrevibacter Smithii is Highly Prominent in the Small Bowel of Rates, Gastroenterology—Proceedings from Digestive Week, 2012, vol. 142(5), Suppl. 1, page S-541, Abstract Only.
Rumessen et al., Carbohydrate Malabsorption: Quantification by Methane and Hydrogen Breath Tests, Scandinavian Journal of Gastroenterology, 1994, 29:826-832.
Rutgeerts et al., Ileal dysfunction and bacterial overgrowth in patients with Crohn's disease, European J Clin Invest., 1981, 11(3):199-206.
Salminen et al., Clinical uses of probiotics for stabilizing the gut mucosal barrier: successful strains and future challenges, Antonie Van Leeuwenhoek., 1996, 70(2-4):347-358.
Sameshima et al., Effect of intestinal Lactobacillus starter cultures on the behaviour of *Staphylococcus aureus* in fermented sausage, Int. J. Food Microbiol., 1998, 41(1):1-7.
Schneider et al., Value of the 14C-D-xylose breath test in patients with intestinal bacterial overgrowth, Digestion, 1985, 32(2):86-91.
Silverman et al., Regional cerebral activity in normal and pathological perception of visceral pain, Gastroenterology, 1997, 112(1):64-72.
Soares et al., Metano no ar Expirado de Criancas com Constipacao Cronica Funcional, Arq. Gastroenterol., 2002, vol. 39(1), pp. 66-72.
Soares et al., Breath methane associated with slow colonic transit time in children with chronic constipation, J. Clin. Gastroenterol. 2005, vol. 39(6), pp. 512-515.
Spanhaak et al., The effect of consumption of milk fermented by Lactobacillus casei suain Shirota on the intestinal microflora and immune parameters in humans, Eur. J. Clin. Nutr., 1998, 52(12):899-907.
Strocchi et al., Detection of malabsorption of low doses of carbohydrate: accuracy of various breath H2 criteria, Gastroenterology, 1993, 105(5):1404-1410.
Sullivan, S.N., A prospective study of unexplained visible abdominal bloating, N Z Med J., 1994, 107(988)428-430.
Swart et al., $^{13}$C breath test in gastrointestinal practice, Scand. J. Gastroenterol., 1998, Suppl. 225:13-18.
Tannock, G. W., Probiotic properties of lactic acid bacteria: plenty of scope for R & D, Trends Biotechnol., 1997, 15(7):270-274.
Thompson et al., Functional bowel disorders in apparently healthy people. Gastroenterology, 1980, 79(2):283-288.
Thompson, et al., Functional bowel disorders and functional abdominal pain. Rome II: A multinational consensus document on functional gastrointestinal disorders, Gut, 1999, 45 Suppl. 2:II43-II47.
Thompson, W., Grant. Probiotics for irritable bowel syndrome: a light in the darkness?, Euro. J. of Gastroenterology & Hepatology, 2001, vol. 13(10), pp. 1135-1136.
Tuohy et al., The prebiotic effects of biscuits containing partially hydrolysed guar gum and fructo-oligosaccharides—a human volunteer study, Br J Nutr, 2001, 86(3):341-348.
Vanderhoof et al., Use of probiotics in childhood gastrointestinal disorders, J Pediatr Gastroenterol Nutr., 1998, 27(3):323-332.
Veldhuyzen Van Zanten et al., Design of treatment trials for functional gastrointestinal disorders, Gut, 1999, 45 Suppl II:II69-II77.
Weaver et al., Incidence of methanogenic bacteria in a sigmoidoscopy population: an association of methanogenic bacteria and diverticulosis, Gut, 1986, 27(6):698-704.
Whitehead et al., Effects of stressful life events on bowel symptoms: Subjects with irritable bowel syndrome compared with subjects without bowel dysfunction, Gut, 1992, 33(6):825-830.
Whitehead et al., Definition of a responder in clinical trials for functional gastrointestinal disorders: reports on a symposium, Gut, 1999, 45 Suppl 2:II78-II79.
Wolf et al., Safety and tolerance of Lactobacillus reuteri supplementation to a population infected with the human immunodeficiency virus, Food Chem. Toxicol. 1998, 36(12):1085-1094.
Zhang et al., Human gut microbiota in obesity and after gastric bypass, PNAS, 2008, pp. 1-6.
PCT/US2003/16656 International Search Report dated Dec. 18, 2003; 2 pages.
PCT/US2003/16656 International Preliminary Examination Report dated Jun. 14, 2004); 4 pages.
PCT/US2014/027697 International Search Report and Written Opinion dated Oct. 3, 2014; 10 pages.
PCT/US2014/027697 International Preliminary Report on Patentability dated Sep. 15, 2015; 7 pages.
PCT/US2015/045140 International Search Report and Written Opinion dated Nov. 19, 2015, 8 pages.
PCT/US2015/045140 International Preliminary Report on Patentability dated Feb. 14, 2017, 6 pages.
PCT/US2016/025214 International Search Report and Written Opinion dated Jun. 2, 2016; 13 pages.
PCT/US2016/025214 International Preliminary Report on Patentability dated Oct. 3, 2017; 11 pages.
EP 03741819.1 Supplemental Search Report dated Apr. 5, 2007, 4 pages.
EP 10173966.2 Supplemental Search Report dated Sep. 30, 2010, 3 pages.
EP 10173966.2 European Extended Search Report dated Oct. 14, 2010, 8 pages.
EP 14770590.9 Extended Search Report dated Oct. 26, 2016; 11 pages.
EP 15831885.7 Extended Search Report dated Dec. 13, 2017, 18 Pages.
International Search Report and Written Opinion of PCT/US2017/038499, dated Aug. 29, 2017, 7 Pages.
Extended European Search Report of EP 16774176.8, dated Oct. 31, 2018, 12 Pages.
Synthetic Biologics, Synthetic Biologies' Novel Irritable Bowel Syndrome with Constipation (IBS-C) Program Featured in American College of Gastroenterology Poster, 2015, 3 Pages.
clinicaltrials.gov., A Study of the Effect of SYN-010 on Subjects with IBS-C—Study Results, 2017, Retrieved from the Internet: URL: https://clinicaltrials.gov/ct2/show/results/NCT02495623?sect-X70156#outcome1, Retrieved on Jul. 19, 2018, 7 Pages.
Gottlieb et al., Review Article: Inhibition of Methanogenic Archaea by Statins as a Targeted Management Strategy for Constipation and Related Disorfers, 2016, Alimentary Pharmacology & Therapeutics, vol. 43(2), pp. 197-212.
Jahromi et al., Lavastatin-Enriched Rice Straw Enhances Biomass Quality and Supresses Ruminal Methanogenesis, 2013, Biomed Research Int'l, vol. 2013, Article ID 397934, 13 Pages.
Jahromi et al., Lavastatin in Aspergillus Terms: Fermented Rice Straw Extracts Interferes with Methane Production and Gene Expression in Methanobrevibacter Smithii, 2013, Biomed Research Int'l, vol. 2013, Article ID 604721, 10 Pages.
Marsh et al., Lavastatin Lactone Inhibits Methane Production in Human Stool Homogenates, 2015, American Journal of Gastroenterology, vol. 110, No. Suppl. 1, Page S753.
Morales et al., Lovastatin Improvies Stool Form in Methanobrevibacter Smithii Colonized Rats with Constipation, 2015, Gastroenterology, Pages S-779-S-780.
Syntheticbiologics, SYN-010—Treatment of IBS-C, 2015, Retrieved from the Internet: URL: https://www.youtube.com/watch?v=-1xzseth6Z8, Retrieved on Oct. 3, 2018, 1 Page.
International Preliminary Report on Patentability of PCT/US2017/038499, dated Dec. 25, 2018, 6 Pages.
clinicaltrials.gov, A Single-Dose, Open-Label, Study to Evaluate the Sustainability of the Effects of SYN-010 in Patients with IBS-C, 2018, NCT02493036, 5 Pages.

(56) References Cited

OTHER PUBLICATIONS

Hubert et al., Development of a Modified-Release Formulation of Lovastatin Targeted to Intestinal Methanogens Implicated in Irritable Bowel Syndrome with Constipation, 2018, Journal of Pharmaceutical Sciences, vol. 107, pp. 662-671.
Mello et al., Methane Production and Small Intestinal Bacterial Overgrowth in Children Living in a Slum, 2012, World J. Gastroenterol., vol. 18(41), 5932-5939.
Reddymasu et al., Small intestinal bacterial overgrowth in irritable bowel syndrome: are there any predictors? 2010, BMC Gastroenterology, vol. 10(23), 5 Pages.
Morgavi et al., Fungal Secondary Metabolites from *Monascus* spp. Reduce Rumen Methane Production in vitro and in vivo., 2013, J. Anim. Sci., vol. 91(2), pp. 848-860.
Lekha Saha, Irritable bowel syndrome: Pathogenesis, diagnosis, treatment, and evidence-based medicine, World Journal of Gastroenterology, 2014, vol. 20(22), pp. 6759-6773.
Anonymous, Synthetic Biologies' Initiates SYN-010 Phase 2 Clinical Trial to Treat Irritable Bowel Syndrom with Constipation (IBS-C), PR Newswire, 2015, downloaded from the internet: https://prnewswire.com/news-releases/synthetic-biologics-initiates-syn-010-phase-2-clinical-trial-to-treat-irritable-bowel-syndrome-with-constipation-ibs-c-300105780.html, 4 pages.
Hubert et al., Development of a Modified-Release Formulation of Lovastatin Targeted to Intestinal Methanogens Implicated in Irritable Bowel Syndrome With Constipation, Journal of Pharmaceutical Sciences, 2018, vol. 107, pp. 362-671.

\* cited by examiner

ANTI-METHANOGENIC LOVASTATIN ANALOGS OR DERIVATIVES AND USES THEREOF

CROSS-REFERENCE TO RELATED APPLICATIONS

This application is a continuation of U.S. patent application Ser. No. 15/560,145 filed Apr. 27, 2018 which is a National Phase of International Application No. PCT/US2016/025214 filed Mar. 31, 2016, which designated the U.S. and that International Application was published under PCT Article 21(2) in English, which claims the benefit of and priority under 35 U.S.C. § 119(e) to U.S. Provisional Patent Application No. 62/141,413, filed Apr. 1, 2015, the entirety of which is hereby incorporated by reference.

FIELD OF THE INVENTION

The present invention relates to, in part, methods and compositions for the treatment of methanogen-associated disorders such as, for example, Irritable Bowel Syndrome (IBS) using anti-methanogenic lovastatin analogs and derivatives thereof.

BACKGROUND

The human microbiome is proving to be a vital component of both human health and disease. For example, the microbiome of the gastrointestinal (GI) tract underlies central processes of nutrient capture and metabolism; however, disruption of this microbiome is believed to be causative of a number of disorders that may severely reduce the quality of an afflicted subject's life, or worse.

Irritable Bowel Syndrome (IBS) affects an estimated 30 million people in the United States alone. IBS is a functional GI disorder that results in abdominal pain and/or discomfort, along with changes in bowel habits. It is often classified into four subtypes: constipation-associated IBS (IBS-C); diarrhea-associated IBS (IBS-D); mixed (or alternating) IBS (IBS-M or IBS-A); and unsubtyped (or unspecified) IBS (IBS-U).

Recent studies suggest a link between intestinal methane ($CH_4$) production and constipation in IBS-C as well as chronic idiopathic constipation (CIC). Methane ($CH_4$) production in humans, which is due to methanogenic archaea in the intestine (including *Methanobrevibacter smithii* (*M. smithii*)), likely reflects a microbiome disruption.

Antibiotic therapy may not be a feasible treatment for this affliction, as methanogens such as *M. smithii* are highly resistant to most classes of antibiotics and the likely chronic administration of antibiotics comes with a number of therapeutic risks, including further microbiome disruption.

Recent studies have suggested that certain statin drugs, including lovastatin, are promising candidates for the treatment of disorders such as IBS-C and CIC. Accordingly, the field would benefit from further related agents that may be able to provide treatment effects with benefits such as reduced doses and/or more extensive benefits.

SUMMARY OF THE INVENTION

Accordingly, the present invention provides, inter alia, improved compositions, formulations and methods for the treatment of various methanogen-associated disorders. In one aspect, the present invention provides for methods of inhibiting or reducing methanogenesis and/or methane accumulation by administering an anti-methanogenic lovastatin analog or derivative to a subject in need thereof. In some embodiments, the subject suffers from IBS, such as IBS-C. In other embodiments, the subject suffers from obesity. In yet another embodiment, the subject suffers from diabetes. In various embodiments, the present invention provides for methods of treating or preventing a methanogen-associated disorder optionally selected from one or more of IBS, such as IBS-C, diabetes, and obesity by administering an anti-methanogenic lovastatin analog or derivative to a subject in need thereof. In an embodiment, methods are provided for treating constipation. In another embodiment, methods are provided for reducing or eliminating enteric methane production. In various embodiments, the anti-methanogenic lovastatin analog or derivative is a compounds described herein, such as lovastatin did lactone.

In another aspect, the present invention provides, in part, modified-release formulations comprising anti-methanogenic lovastatin analogs or derivatives. In some embodiments, the modified-release formulations release at least 60% of the anti-methanogenic lovastatin analog or derivative, after the stomach and into one or more regions of the intestinal tract. In certain embodiments, the formulation releases the anti-methanogenic lovastatin analog or derivative in the small intestine, including one or more of the duodenum, jejunum, and ileum. In other embodiments, the formulation releases the anti-methanogenic lovastatin analog or derivative in the large intestine (e.g., one or more of the cecum, ascending, transverse, descending or sigmoid portions of the colon, and rectum).

In various embodiments, the anti-methanogenic lovastatin analog or derivative is in either the lactone or ß-hydroxyacid form. In some embodiments, the anti-methanogenic lovastatin analog or derivative is in the lactone form. In some embodiments, the anti-methanogenic lovastatin analog or derivative is lovastatin diol lactone.

In various embodiments, the modified-release formulation is administered orally to a subject in need thereof. In one embodiment, the formulation may be in the form of a capsule or a tablet. In an embodiment, the formulation comprises a modified-release coating that is substantially stable in gastric fluid. In another embodiment, the modified-release coating may be degraded by a microbial enzyme present in the gut flora. In a further embodiment, the modified-release coating may have a solubility and/or stability that is pH dependent. In other embodiments, the modified-release coating may have a time-dependent erosion profile.

In various embodiments, the modified-release formulation comprises a first dose of lovastatin or at least one anti-methanogenic lovastatin analog or derivative and a second dose of at least one anti-methanogenic lovastatin analog or derivative (e.g. the first and second doses may be the same or different anti-methanogenic lovastatin analog or derivative at a given dose, or the first and second doses may be the same anti-methanogenic lovastatin analog or derivative at the same or different doses, or the first or second doses may comprise lovastatin). In various embodiments, the first dose and the second dose are released at different times and/or at different pHs and in different regions of the gastrointestinal tract. In some embodiments, the first and/or second dose of at least one anti-methanogenic lovastatin analog or derivative is encapsulated in a core particle. A modified-release coating may be disposed over the core particle to form a modified-release particle. In certain embodiments, the formulation comprises a plurality of modified-release particles. In an illustrative embodiment, the formulation maybe in the form of a capsule. In another embodiment, the first and second dose of at least one anti-methanogenic lovastatin analog or derivative is encapsulated in a layer. A modified-release coating may be disposed over the layer to form a modified-release layer. In certain embodiments, the formulation comprises a plurality of modified-release layers. In an illustrative embodiment, the formulation maybe in the form of a multilayer tablet.

In some embodiments, the first dose and second dose of anti-methanogenic lovastatin analog or derivative are released at different times and or at different pHs. In illustrative embodiments, the first dose may release the anti-methanogenic lovastatin analog or derivative at the duodenum while the second dose may release the anti-methanogenic lovastatin analog or derivative at the ileum. In other embodiments, the first dose may release the anti-methanogenic lovastatin analog or derivative at the small intestine while the second dose may release the anti-methanogenic lovastatin analog or derivative at the large intestine.

The formulations of the present invention may further include a pharmaceutically acceptable excipient. In some embodiments, the formulation may further include an agent which prevents or reduces lactone ring-opening, such as an esterase inhibitor (e.g. grapefruit juice; including flavonoid components such as, for example, naringenin, kaempferol, morin, galangin, and quercetin; flavoring ester mixtures in, for example, strawberry juice (e.g. phenyl benzoate, propyl paraben, phenethyl isobutyrate, bacampicillin, talampicillin, p-tolyl benzoate, ethyl paraben, diethyl phthalate, octyl acetate, and pivampicillin) and/or a paraoxonase inhibitor (e.g. PON1 or PON3 inhibitor). In some embodiments, the formulation may further include an inhibitor of the organic anion transporting polypeptide (OATP) transporter, such as one or more of green tea extract, epicatechin gallate (EGG) and epigallocatechin gallate (EGCG). In some embodiments, the OATP inhibitor is released prior to release of the lovastatin analog or derivative. The formulations of the present invention may also further include an additional therapeutic agent such as, by way of non-limiting example, a prokinetic agent.

In various embodiments, the methods and formulations described herein eradicate or reduce methane production, which is causative of, or correlative with, various methanogen-associated disorders, including, for example, IBS (e.g. IBS-C), diabetes and obesity. In various embodiments, the methods and formulations described herein target the gastrointestinal (GI) tract and therefore provide for specific delivery to a site of methanogen colonization and/or methane production and/or accumulation while avoiding or reducing systemic exposure to anti-methanogenic lovastatin analogs or derivatives and minimizing their systemic effects. As such, the present invention provides for effective treatments that avoid side effects associated with chronic systemic administration (e.g. muscle pain, abnormalities in liver enzyme tests, etc). Further, in some embodiments, the present invention surprisingly treats bowel-disorders despite reports linking statin use to, for example, constipation (see, e.g., Fernandes et al. Possible association between statin use and bowel dysmotility. *BMJ Case Reports* 2012; 10.1136/bcr.10.2011.4918 and Merck Global Medical Information. Professional Information Response UK11-010274, the contents of which are hereby incorporated by reference in their entireties). Further, in some embodiments, the present invention surprisingly treats diabetes despite reports linking statin use to this disorder (see, e.g., *Circ Cardiovasc Qual Outcomes* 6 (4): 390-9, the contents of which are hereby incorporated by reference in their entirety).

In an embodiment, the present invention provides for methods of inhibiting or reducing methanogenesis and/or methane accumulation by administering formulations disclosed herein to a subject in need thereof. In various embodiments, the present invention provides for methods of treating or preventing a methanogen-associated disorder optionally selected from one or more of IBS, such as IBS-C, diabetes, and obesity by administering a formulations described herein to a subject in need thereof. In an embodiment, methods are provided for treating constipation using the formulations described herein. In another embodiment, methods are provided for reducing or eliminating enteric methane production using the formulations described herein.

DETAILED DESCRIPTION OF THE INVENTION

Figure 1A:
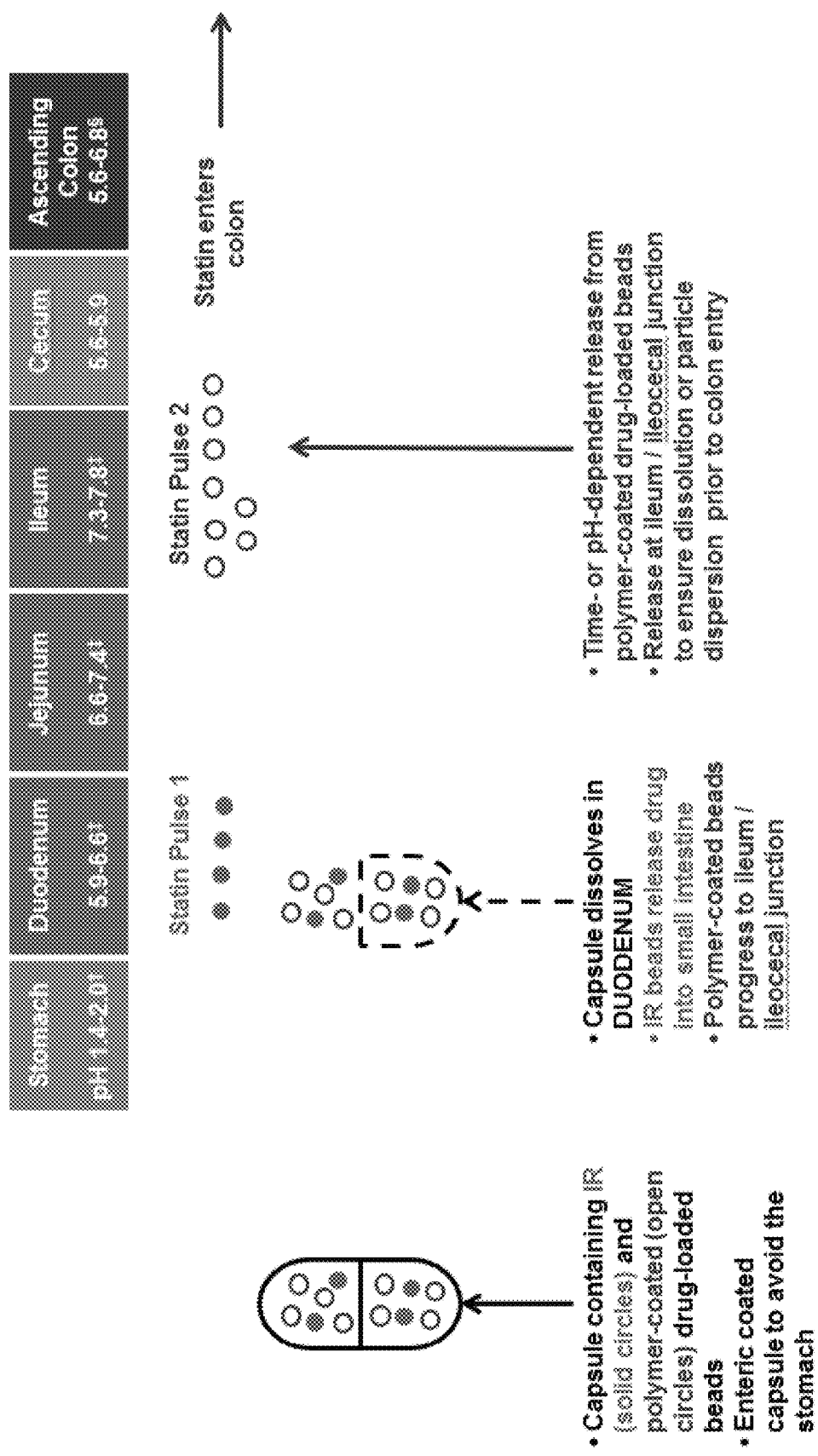
FIGS. 1A-1B depict some embodiments of a modified-release formulation in the form of encapsulated beads which releases a first dose of anti-methanogenic lovastatin analog or derivative at the duodenum and a second dose of anti-methanogenic lovastatin analog or derivative at the ileum.
Figure 1B:
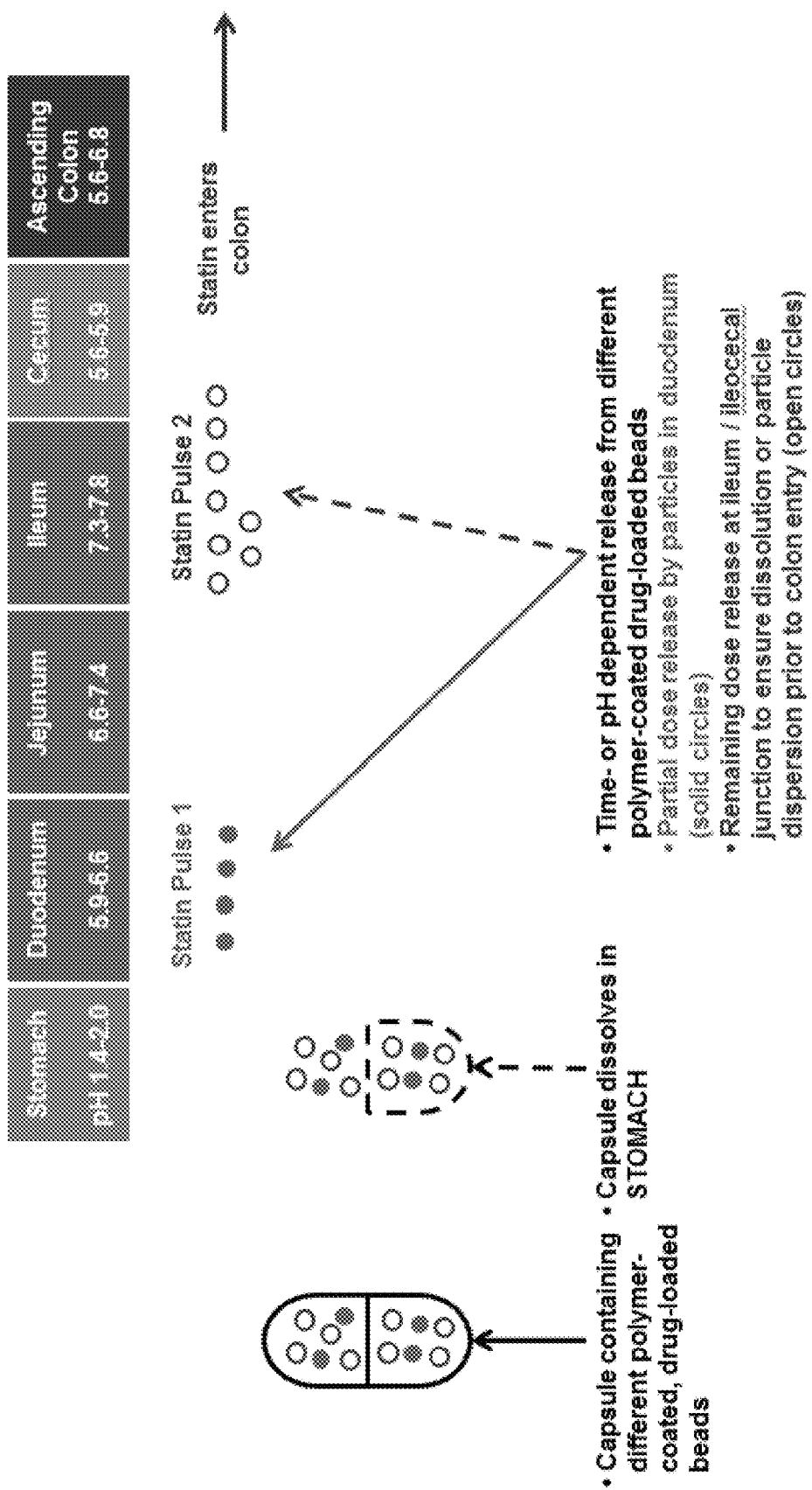
Figure 2:
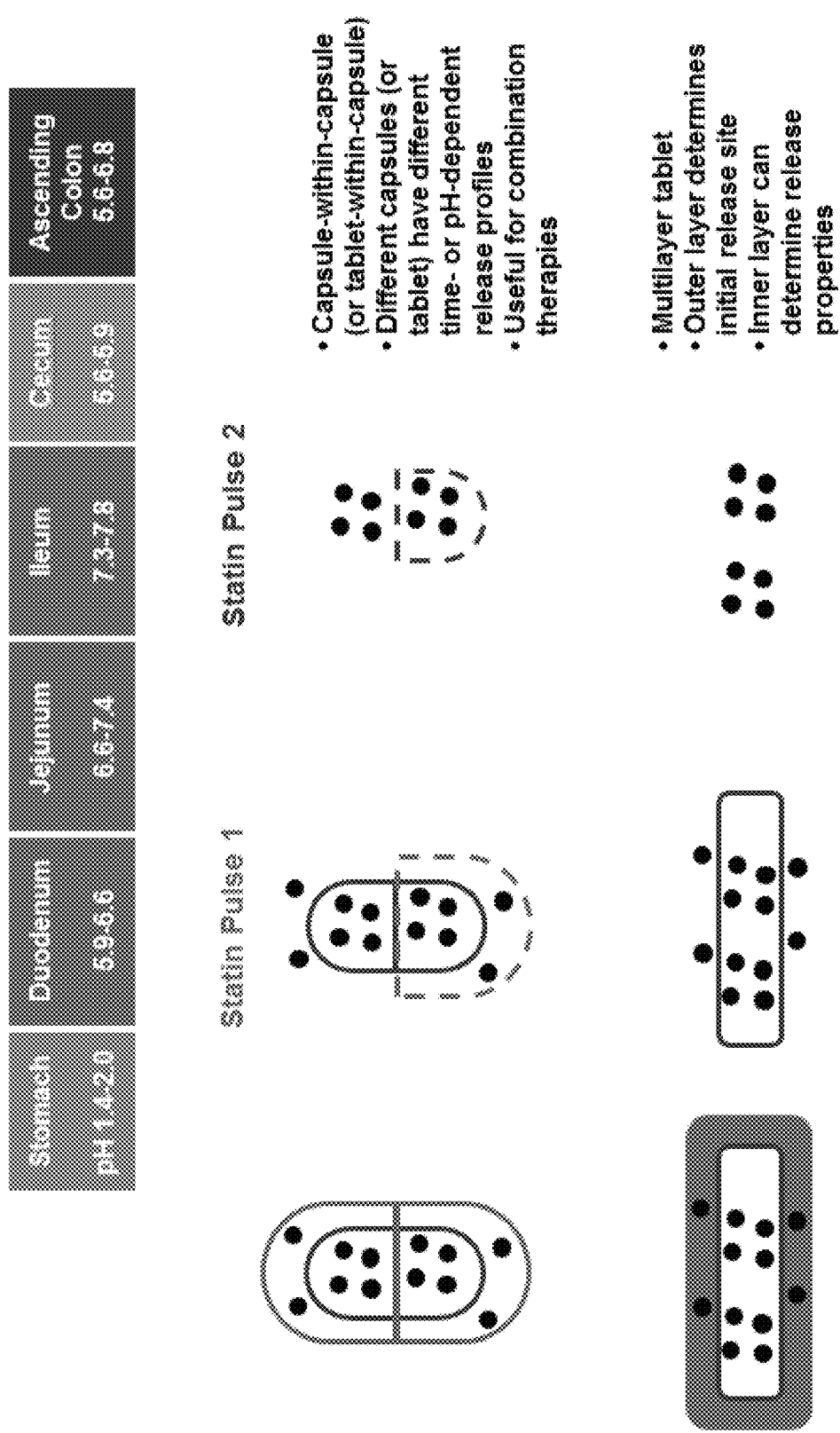
FIG. 2 depicts embodiments of modified-release formulations as multi-layer capsules or tablets for delivery of anti-methanogenic lovastatin analogs or derivatives to the intestines (an illustrative commercial material is shown, related materials are known in the art).
Figure 3A:
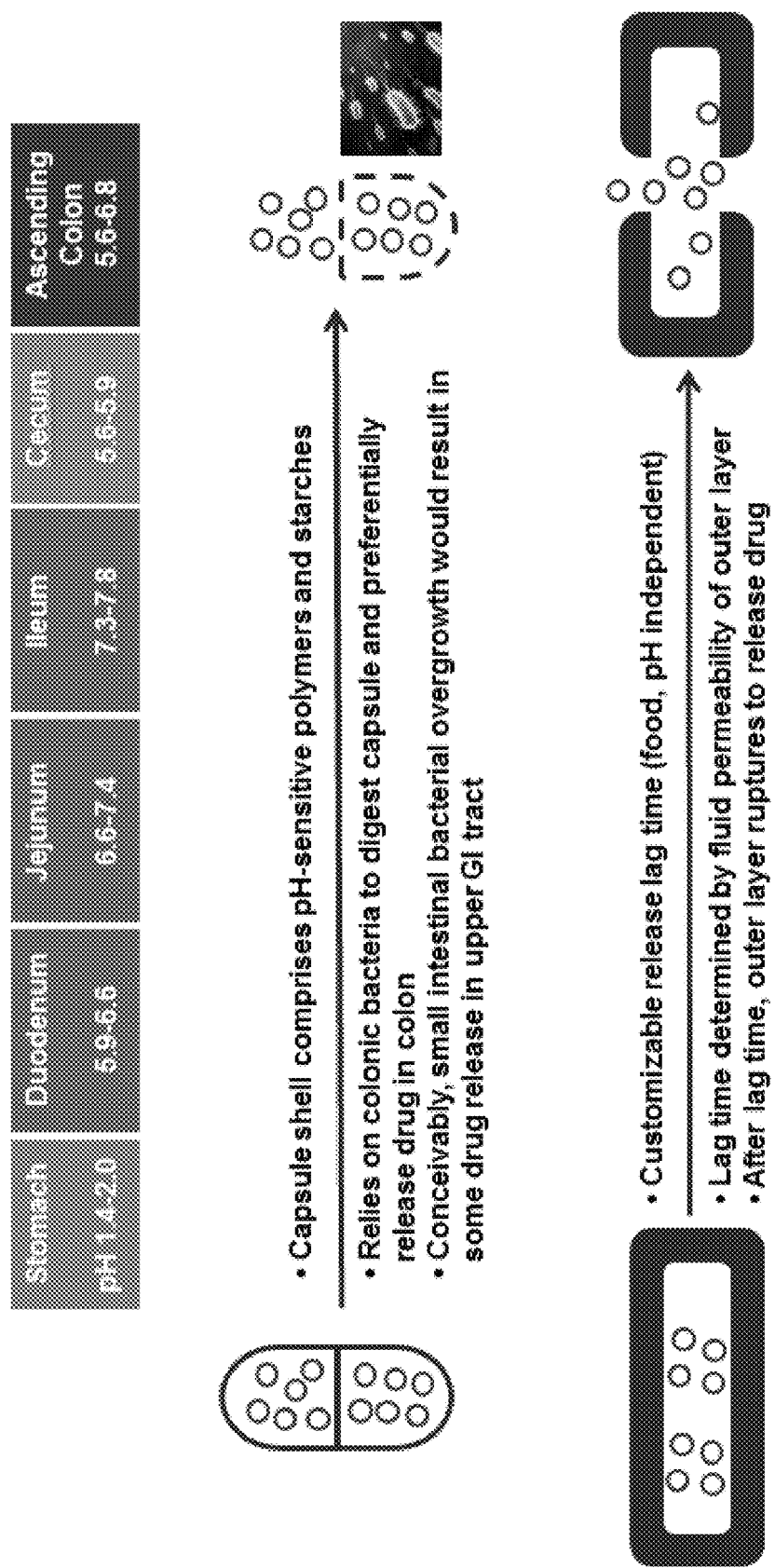
FIGS. 3A-3B depict embodiments of modified-release formulations for colonic delivery of anti-methanogenic lovastatin analogs or derivatives (an illustrative commercial material is shown, related materials are known in the art).
Figure 3B:
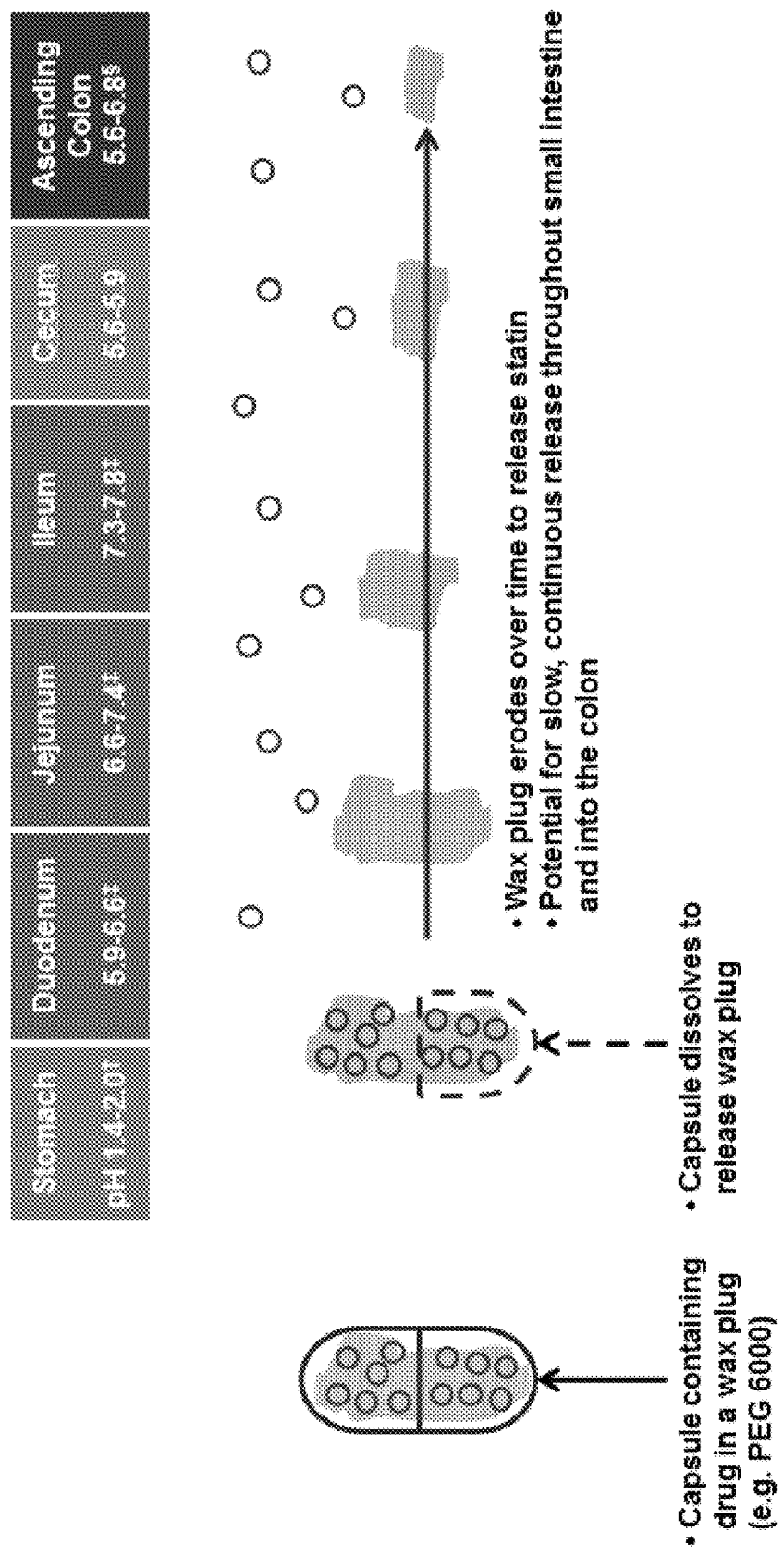

The present invention is based, in part, of the surprising discovery of methods and formulations that are useful in effectively treating or preventing methanogen-associated disorders while avoiding side effects. The present invention provides, inter alia, methods of treating or preventing methanogen-associated disorders using one or more anti-methanogenic lovastatin analogs or derivatives, including, without limitation, lovastatin diol lactone. The present invention additionally provides, inter alia, modified-release formulations comprising one or more anti-methanogenic lovastatin analogs or derivatives, including, without limitation, lovastatin diol lactone, which are useful in, for example, the treatment of methanogen-associated disorders such as, for example, IBS (including, for example, IBS-C).

As used herein, "lovastatin analogs or derivatives" refer to a class of compounds including pharmaceutically acceptable analogs, derivatives, esters, prodrugs, salts, solvates, enantiomers, stereoisomers, active metabolites, co-crystals, and other physiologically functional derivatives of lovastatin. Such lovastatin analogs or derivatives may be used as lipid lowering agents. However, the prior use of the lovastatin analogs or derivatives does not necessarily imply a mechanism of action in the treatment of methanogenesis. That is, in some embodiments, the lovastatin analog or derivative may inhibit the enzyme HMG-CoA reductase while in others it may have another manner of causing an effect. For example, the lovastatin analog or derivative may target a methanogenic enzyme, such as, for example, one or more of adh alcohol dehydrogenase; fdh formate dehydrogenase; fno F420-dependent NADP oxidoreductase; ftr formyl-MF:H4MPT formyltransferase; fwd formyl-MF dehydrogenase; hmd methylene-H4MPT dehydrogenase; mch methenyl-H4MPT cyclohydrolase; mtd F420-dependent methylene-H4MPT dehydrogenase; mer F420-dependent methylene-H4MPT reductase; mtr methyl-H4MPT:CoM-methyltransferase; mcr methyl-CoM reductase; and the mtaB methanol:cobalamin methyltransferase heterodisulfide reductase system. In some embodiments, the lovastatin analog or derivative does not substantially inhibit the enzyme HMG-CoA reductase. In some embodiments, the lovastatin analog or derivative is present in the lactone form, for example, as the active form (e.g. in a subject's GI tract). In some embodiments, the lovastatin analog or derivative is lovastatin diol lactone.

Illustrative "lovastatin analogs or derivatives" are compounds of Formulae Ia-e, IIa-e, IIIa-e, IVa-e, V, VI, VII, VIII, IX, X, XI, XII, XIII, XIV, XV, XVI, XVII, XVIII, XIX, XX, XXI, XXII, XXIII, XXIV, XXV, XVI, XVII, XVIII, XVIX, XXX, XXXI, XXXII, XXXIII, XXXIV, XXXV and XXXVI, as described herein. In some embodiments, the lovastatin analog or derivative is lovastatin diol lactone.

Systemic statin usage has been associated with adverse side effects such as elevation in hepatic enzyme levels and muscle problems (e.g., myalgias, rhabdomyolysis, and severe myopathy). Further, systemic statin usage has been linked to digestive disorders in some patients. The present invention also provides modified release formulations comprising anti-methanogenic lovastatin analogs or derivatives that minimize absorption of the administered lovastatin analogs or derivatives from the intestine into the systemic circulation and reduce potential side effects or disease exacerbating effects. Additionally, not all patients with IBS-C or CIC will require lipid lowering therapy, so systemic absorption of the anti-methanogenic lovastatin analogs or derivatives from the modified release formulations of the present invention will ideally be insufficient to provide a clinically-meaningful reduction in total cholesterol (total-C), or low-density lipoprotein cholesterol (LDL-C), or apolipoprotein B (Apo B), or triglycerides (TG), or a clinically-meaningful increase in high-density lipoprotein cholesterol (HDL-C) (for example, a reduction of less than 5% in serum LDL-C levels at 6 weeks).

Anti-Methanogenic Lovastatin Analogs or Derivatives

The present invention contemplates the use of lovastatin analogs or derivatives, which includes pharmaceutically acceptable analogs, esters, prodrugs, salts, solvates, enatiomers, stereoisomers, active metabolites, co-crystals, and other physiologically functional derivatives of lovastatin. Lovastatin, also known as mevinolin, was described, for example, in U.S. Pat. No. 4,231,938, the entire contents of which are incorporated by reference herein. Various anti-methanogenic lovastatin analogs or derivatives thereof are contemplated. In various embodiments, any of these anti-methanogenic lovastatin analogs or derivatives are in the lactone form (e.g. substantially in the lactone for, or in an equilibrium in which the lactone form is predominant of the beta-hydroxy form), where applicable.

In various embodiments, the anti-methanogenic lovastatin analog or derivative comprises polyhydronaphthyl moieties and various 8-acyloxy groups attached thereto. In an embodiment, the anti-methanogenic lovastatin analog or derivative may be a group of 6(R)-[2-(8'-acyloxy-2'-methyl-6'-methyl(or hydrogen)-polyhydronaphthyl-1')-ethyl]-4(R)-hydroxy-3,4,5,6-tetrahydro-2H-pyran-2-ones or the hydroxy acid form of said pyranones, the pharmaceutically acceptable salts of said hydroxy acids and to the lower alkyl (e.g., $C_{1-4}$alkyl ester) and phenyl, dimethylamino or acetylamino substituted lower alkyl esters of the lactone or hydroxy acid form. In some embodiments, the anti-methanogenic lovastatin analog or derivative may be a dihydro and tetrahydro analog of lovastatin. Such analogs and derivatives are described, for example, in U.S. Pat. Nos. 4,294,846, 4,450,171, and 4,444,784, the entire contents of which are incorporated by reference herein (including, by way of illustration, disclosures of specific compounds and synthetic schemes). For example, in some embodiments, the anti-methanogenic lovastatin analog or derivative may have the formula:

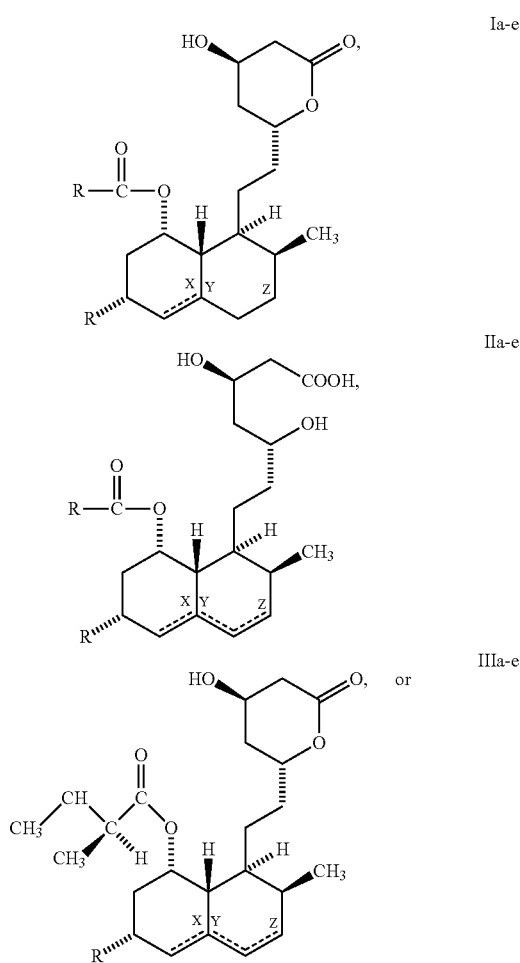

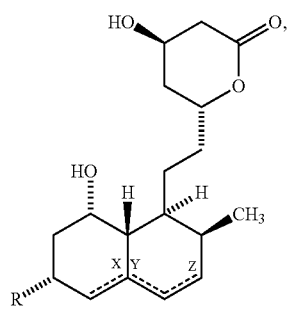

IVa-e

| STEREOCHEMISTRY OF THE HYDRONAPHTHYL SERIES | | |
|---|---|---|
| Series | Double Bonds Present | Structure |
| a | X and Z | 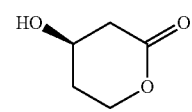 |
| b | X | |
| c | Y | |
| d | Z | |
| e | None | | or pharmaceutically acceptable salts thereof, wherein R' represents H or $CH_3$; X, Y, and Z represent possible double bonds; the series a-e are defined in the table above and, where applicable, R represents: (1) $C_{1-10}$ straight, or branched chain alkyl except (S)-2-butyl, (2) $C_{3-10}$ cycloalkyl, (3) $C_{2-10}$ alkenyl, (4) $C_{1-10}$ $CF_3$-substituted alkyl, (5) phenyl, (6) halophenyl, wherein halo is chloro, fluoro, bromo or iodo, (7) phenyl-$C_1$-3 alkyl, or (8) substituted phenyl-$C_1$-3 alkyl in which the substituent is halo, such as fluoro, chloro, bromo, or iodo, $C_1$-3 alkyl or $C_1$-3 alkoxy.

In another embodiment, the anti-methanogenic lovastatin analog or derivative may have one or more 8-acyloxy groups as described, for example, in U.S. Pat. No. 4,661,483, the entire contents of which are incorporated by reference herein (including, by way of illustration, disclosures of specific compounds and synthetic schemes). For example, the anti-methanogenic lovastatin analog or derivative may have the formula:

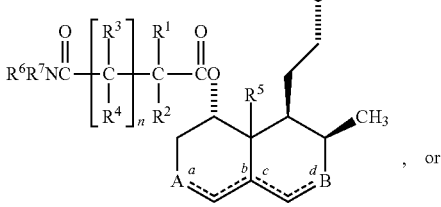

V

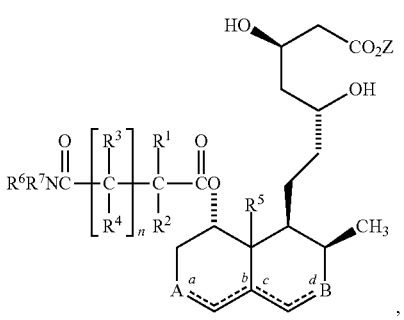

VI wherein: n is 0 to 5; $R^1$ is $C_{1-3}$ alkyl; $R^2$ is hydrogen or $C_{1-3}$ alkyl; $R^3$ and $R^4$ independently are hydrogen, $C_{1-3}$ alkyl, $C_{3-7}$ cycloalkyl, phenyl or substituted phenyl in which the substituents are X and Y and when n is 2 to 5, each of the $R^3$ s and $R^4$ s are independently hydrogen or $C_{1-3}$ alkyl, $C_{3-7}$ cycloalkyl or only one of the $R^3$ s and $R^4$ s is phenyl or substituted phenyl; $R^5$ is hydrogen or hydroxy; $R^6$ and $R^7$ independently are hydrogen, or $C_1$-3 alkyl or $R^6$ and $R^7$ together with the nitrogen atom to which they are attached form a heterocycle selected from piperidinyl, morpholinyl, pyrrolidinyl, piperazinyl or thiomorpholinyl; A is

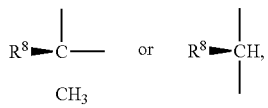

in which $R^8$ is hydrogen or hydroxy; B is

in which $R^9$ is hydrogen or hydroxy; a, b, c and d represent single bonds, one of a, b, c or d represents a double bond, or both a and c or both b and d represent double bonds provided that when a is a double bond, A is

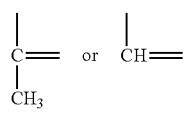

and when d is a double bond, B is

and X and Y independently are hydrogen, halogen, trifluoromethyl, $C_{1-3}$ alkyl, nitro, cyano or a group selected from: (a) $R^{10}O(CH_2)_m$ in which m is 0 to 3 and $R^{10}$ is hydrogen, $C_{1-3}$ alkyl or hydroxy-$C_{1-3}$ alkyl; (b)

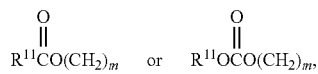

in which $R^{11}$ is hydrogen, $C_{1-3}$ alkyl, hydroxy-$C_{2-3}$ alkyl, phenyl, naphthyl, amino-$C_{2-3}$ alkyl, $C_{1-3}$ alkylamino-$C_{1-3}$ alkyl, di($C_{1-3}$ alkyl)amino-$C_{1-3}$ alkyl, hydroxy-$C_{a-s}$ alkylamino-$C_{1-3}$ alkyl or di(hydroxy-$C_{2-3}$ alkyl)-amino-$C_{1-3}$ alkyl; (c)

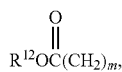

in which $R^{12}$ is hydrogen, $C_{1-3}$ alkyl, hydroxy-$C_{1-3}$-alkyl, $C_{1-3}$ alkoxy-$C_{1-3}$ alkyl, phenyl or naphthyl; (d) $R^{13}R^{14}N(CH_2)_m$,

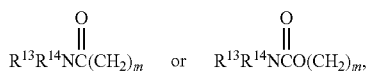

in which $R^{13}$ and $R^{14}$ independently are hydrogen, $C_{1-3}$ alkyl, hydroxy-$C_{2-3}$ alkyl or together with the nitrogen atom to which they are attached form a heterocycle group selected from piperidinyl, pyrrolidinyl, piperazinyl, morpholinyl or thiomorpholinyl; (e) $R^{15}S(O)_p (CH_2)_m$ in which p is 0 to 2 and $R^{15}$ is hydrogen, $C_{1-3}$ alkyl, amino, $C_{1-3}$ alkylamino or di($C_{1-3}$ alkyl)-amino; Z is hydrogen, $C_{1-5}$ alkyl or $C_{1-5}$ alkyl substituted with a member of the group consisting of phenyl, dimethylamino or acetylamino; and pharmaceutically acceptable salts of the compounds of the Formula VI in which Z is hydrogen.

In certain embodiments, the anti-methanogenic lovastatin analog or derivative may have functionalized 8-acyloxy groups as described, for example, in U.S. Pat. Nos. 4,864,038, 4,937,264, 4,847,306, 5,049,696, 4,766,145, 4,876,279, 4,876,366, 4,937263, 4,771,071, and 4,916,162, the entire contents of which are incorporated by reference herein (including, by way of illustration, disclosures of specific compounds and synthetic schemes).

In an embodiment, the anti-methanogenic lovastatin analog or derivative may be any one described in U.S. Pat. No. 4,864,038, the entire contents of which are incorporated by reference herein (including, by way of illustration, disclosures of specific compounds and synthetic schemes) and have the formula:

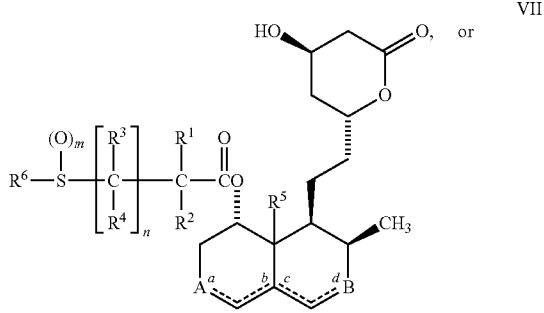

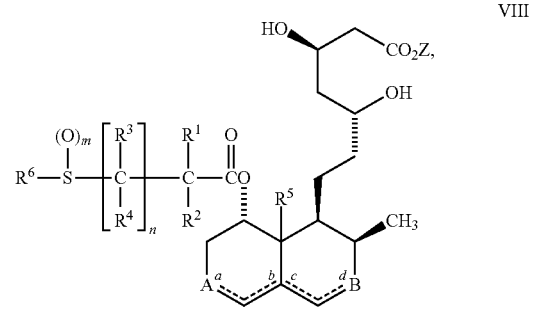

wherein: m is 0 to 2; n is 0 to 5; $R^1$ is $C_{1-3}$ alkyl; $R^2$ is hydrogen or $C_{1-3}$ alkyl; $R^3$ and $R^4$ independently are hydrogen, $C_{1-3}$ alkyl, $C_{3-7}$ cycloalkyl, phenyl or substituted phenyl in which the substituents are X and Y and when n is 2 to 5, each of the $R^3$s and $R^4$s are independently hydrogen or $C_{1-3}$ alkyl, $C_{3-7}$ cycloalkyl or only one of the $R^3$s and $R^4$s is phenyl or substituted phenyl; $R^5$ is hydrogen or hydroxy; $R^6$ is phenyl or substituted phenyl wherein the substituents are X and Y; A is

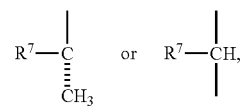

in which $R^7$ is hydrogen or hydroxy; B is $CHR^8$ which $R^8$ is hydrogen or hydroxy; and a, b, c and d represent single bonds, one of a, b, c or d represents a double bond, or both a and c or both b and d represent double bonds provided that when a is a double bond, A is

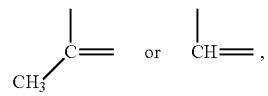

and when d is a double bond, B is

and X and Y independently are hydrogen, halogen, trifluoromethyl, $C_{1-3}$ alkyl, nitro, cyano or a group selected from (a) $R^9O(CH_2)_m$ in which m is 0 to 3 and $R^9$ is hydrogen, $C_{1-3}$ alkyl or hydroxy-$C_{1-3}$ alkyl; (b)

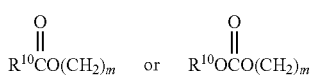

in which $R^{10}$ is hydrogen, $C_{1-3}$ alkyl, hydroxy-$C_{2-3}$ alkyl, phenyl, naphthyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{2-3}$ alkylamino-$C_{1-3}$ alkyl or di(hydroxy-$C_{2-3}$ alkyl)amino-$C_{1-3}$ alkyl; (c)

om which $R^{11}$ is hydrogen, $C_{1-3}$ alkyl, hydroxy-$C_{1-3}$ alkyl, $C_{1-3}$ alkoxy-$C_{1-3}$ alkyl, phenyl or naphthyl; (d) $R^{12}R^{13}N(CH_2)_m$,

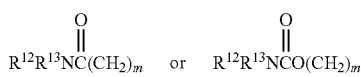

in which $R^{12}$ and $R^{13}$ independently are hydrogen, $C_{1-3}$ alkyl, hydroxy-$C_2$-3 alkyl or together with the nitrogen atom to which they are attached form a heterocycle group selected from piperidinyl, pyrrolidinyl, piperazinyl, morpholinyl or thiomorpholinyl; (e) $R^{14}S(O)_p(CH_2)_m$ in which p is 0 to 2 and $R^{14}$ is hydrogen, $C_{1-3}$ alkyl, amino, $C_{1-3}$ alkylamino or di ($C_{1-3}$ alkyl) amino; Z is hydrogen, $C_{1-5}$ alkyl or $C_{1-5}$ alkyl substituted with a member of the group consisting of phenyl, dimethylamino or acetylamino; and pharmaceutically acceptable salts of the compounds of the Formula VIII in which Z is hydrogen.

In an embodiment, the anti-methanogenic lovastatin analog or derivative may be any one described in U.S. Pat. No. 4,847,306, the entire contents of which are incorporated by reference herein (including, by way of illustration, disclosures of specific compounds and synthetic schemes) and have the formulae:

IX

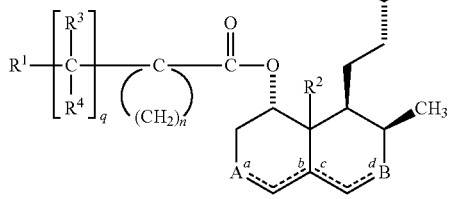

X

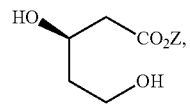

wherein, q is 0 to 5; n is 2 to 7; $R^1$ is $C_{1-6}$ alkyl, $C_{1-6}$ alkyl substituted with a group selected from halogen, hydroxy, $C_{1-3}$ alkylthio, $C_{1-3}$ alkylsulfinyl and $C_{1-3}$ alkylsulfonyl, $C_{1-6}$ alkylthio, $C_{1-6}$ alkylsulfinyl, $C_{1-6}$ alkylsulfonyl, $C_{3-7}$ cycloalkylthio, $C_{3-7}$ cycloalkylsulfinyl, $C_{3-7}$ cycloalkylsulfonyl, $C_{3-7}$ cycloalkyl, phenyl, or phenyl substituted with X and Y; $R^2$ is hydrogen or hydroxy; $R^3$ and $R^4$ independently are hydrogen, $C_{1-3}$ alkyl, $C_{3-7}$ cycloalkyl, phenyl or phenyl substituted with X and Y and when q is 2 to 5, each of the $R^3$s and $R^4$s are independently hydrogen, $C_{1-3}$ alkyl, $C_{3-7}$ cycloalkyl or only one of the $R^3$s and $R^4$s is phenyl or substituted phenyl; A is

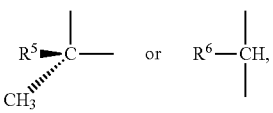

in which $R^5$ is hydrogen or hydroxy; B is $CHR^6$ in which $R^6$ is hydrogen or hydroxy; a, b, c and d represent single bonds, one of a, b, c or d represents a double bond or both a and c or both b and d represent double bonds, provided that when a is a double bond, A is

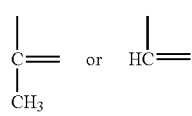

and when d is a double bond, B is

and X and Y independently are hydrogen, halogen, trifluoromethyl, $C_{1-3}$ alkyl, nitro, cyano or a group selected from:
(a) $R^7O(CH_2)_m$ in which m is 0 to 3 and $R^7$ is hydrogen, $C_{1-3}$ alkyl or hydroxy-$C_{1-3}$ alkyl; (b)

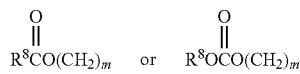

in which $R^8$ is hydrogen, $C_{1-3}$ alkyl, hydroxy-$C_{2-3}$ alkyl, phenyl, naphthyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{2-3}$ alkylamino-$C_{1-3}$ alkyl or di(hydroxy-$C_{2-3}$ alkyl)amino-$C_{1-3}$ alkyl; (c)

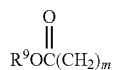

in which $R^9$ is hydrogen, $C_{1-3}$ alkyl, hydroxy-$C_{1-3}$ alkyl, $C_{1-3}$ alkoxy-$C_{1-3}$ alkyl, phenyl, or naphthyl; (d) $R^{10}R^{11}N(CH_2)_m$,

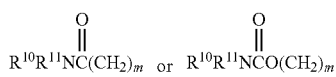

in which $R^{10}$ and $R^{11}$ independently are hydrogen, $C_{1-3}$ alkyl, hydroxy-$C_{2-3}$ alkyl or together with the nitrogen atom to which they are attached form a heterocycle group selected from piperidinyl, pyrrolidinyl, piperazinyl, morpholinyl or thiomorpholinyl; (e) $R^{12}S(O)_p(CH_2)_m$ in which p is 0 to 2 and $R^{12}$ is hydrogen, $C_{1-3}$ alkyl, amino, $C_{1-3}$ alkylamino or di($C_{1-3}$ alkyl)amino; Z is hydrogen, $C_{1-5}$ alkyl or $C_{1-5}$ alkyl substituted with a group selected from phenyl, dimethyl amino or acetylamino; and pharmaceutically acceptable salts of the compounds of the Formula X in which Z is hydrogen.

In some embodiments, the anti-methanogenic lovastatin analog or derivative may be as described in U.S. Pat. No. 4,766,145, the entire contents of which are incorporated by reference herein (including, by way of illustration, disclosures of specific compounds and synthetic schemes) and be of formulae:

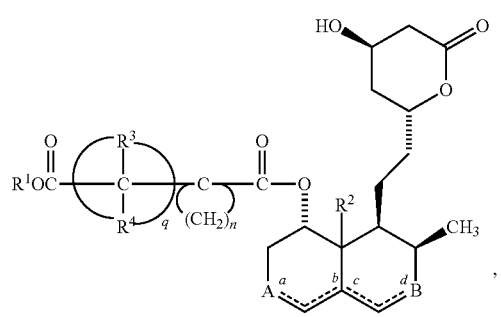

wherein, q is 0 to 5; n is 2 to 7; $R^1$ is $C_{1-6}$ alkyl; $R^2$ is hydrogen or hydroxy; $R^3$ and $R^4$ independently are hydrogen, $C_{1-3}$ alkyl, $C_{3-7}$ cycloalkyl, phenyl or phenyl substituted with X and Y and when q is 2 to 5, each of the $R^3$s and $R^4$s are independently hydrogen, $C_{1-3}$ alkyl, $C_{3-7}$ cycloalkyl or only one of the $R^3$s and $R^4$s is phenyl or substituted phenyl; A is in which $R^5$ is hydrogen or hydroxy; B is —$CHR^6$— in which $R^6$ is hydrogen or hydroxy; a, b, c and d represent single bonds, one of a, b, c or d represents a double bond or both a and c or both b and d represent double bonds, provided that when a is a double bond, A is and when d is a double bond, B is and X and Y independently are hydrogen, halogen, trifluoromethyl, $C_{1-3}$ alkyl, nitro, cyano or a group selected from: (a) $R^7O(CH_2)_m$ in which m is 0 to 3 and $R^7$ is hydrogen, $C_{1-3}$ alkyl or hydroxy-$C_{1-3}$ alkyl; (b)

in which $R^8$ is hydrogen, $C_{1-3}$ alkyl, hydroxy-$C_{2-3}$ alkyl, phenyl, naphthyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{2-3}$ alkylamino-$C_{1-3}$ alkyl or di(hydroxy-$C_{2-3}$ alkyl)amino-$C_{1-3}$ alkyl; (c)

in which $R^9$ is hydrogen, $C_{1-3}$ alkyl, hydroxy-$C_{1-3}$ alkyl, $C_{1-3}$ alkoxy-$C_{1-3}$ alkyl, phenyl, or naphthyl; (d) $R^{10}R^{11}N(CH_2)_m$, in which $R^{10}$ and $R^{11}$ independently are hydrogen, $C_{1-3}$ alkyl, hydroxy-$C_{2-3}$ alkyl or together with the nitrogen atom to which they are attached form a heterocycle group selected from piperidinyl, pyrrolidinyl, piperazinyl, morpholinyl or thiomorpholinyl; (e) $R^{12}S(O)_p(CH_2)_m$ in which p is 0 to 2 and $R^{12}$ is hydrogen, $C_{1-3}$ alkyl, amino, $C_{1-3}$ alkylamino or di($C_{1-3}$ alkyl)amino; Z is hydrogen, $C_{1-5}$ alkyl or $C_{1-5}$ alkyl substituted with a group selected from phenyl, dimethylamino or acetylamino; and pharmaceutically acceptable salts of the compounds of the Formula XII in which Z is hydrogen.

In some embodiments, the anti-methanogenic lovastatin analog or derivative may be as described in U.S. Pat. No.

4,876,366, the entire contents of which are incorporated by reference herein (including, by way of illustration, disclosures of specific compounds and synthetic schemes) and may be of formulae:

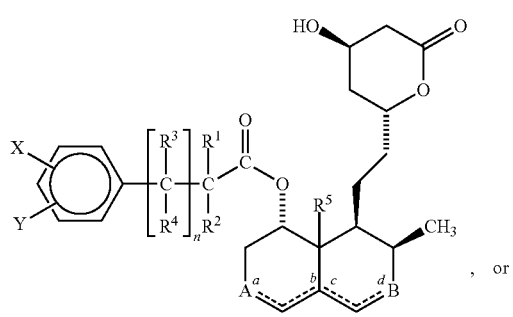

XIII

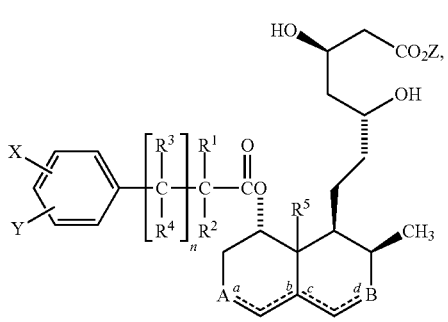

XIV wherein n is 0 to 5; $R^1$ is $C_{1-3}$ alkyl; $R^2$ is hydrogen or $C_{1-3}$ alkyl; $R^3$ and $R^4$ independently are hydrogen, $C_{1-3}$ alkyl, $C_{3-7}$ cycloalkyl, phenyl or substituted phenyl wherein the substituents are X and Y and when n is 2 to 5, each of the $R^3$s and $R^4$s are independently hydrogen, $C_{1-3}$ alkyl, $C_{3-7}$ cycloalkyl or only one of the $R^3$s and $R^4$s is phenyl or substituted phenyl; $R^5$ is hydrogen or hydroxy; X and Y independently are hydrogen, halogen (F, Cl or Br), trifluoromethyl, $C_{1-3}$ alkyl, nitro, cyano or a group selected from:
(a) $R^6O(CH_2)_m$ in which m is 0 to 3 and $R^6$ is hydrogen, $C_{1-3}$ alkyl or hydroxy-$C_{1-3}$ alkyl; (b)

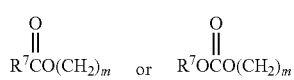

in which $R^7$ is hydrogen, $C_{1-3}$ alkyl, hydroxy-$C_{2-3}$ alkyl, phenyl, naphthyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{2-3}$ alkylamino-$C_{1-3}$ alkyl or di(hydroxy-$C_{2-3}$ alkyl)amino-$C_{1-3}$ alkyl; (c)

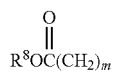

in which $R^8$ is hydrogen, $C_{1-3}$ alkyl, hydroxy-$C_{2-3}$-alkyl, $C_{1-3}$ alkoxy-$C_{1-3}$ alkyl, phenyl or naphthyl; (d) $R^9R^{10}N(CH_2)_m$,

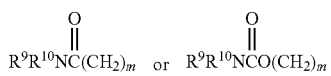

in which $R^9$ and $R^{10}$ independently are hydrogen, $C_{1-3}$ alkyl, hydroxy-$C_{2-3}$ alkyl or together with the nitrogen atom to which they are attached form a heterocyclic group selected from piperidinyl, pyrrolidinyl, piperazinyl, morpholinyl or thiomorpholinyl; (e) $R^{11}S(O)_p (CH_2)_m$ in which p is 0 to 2 and $R^{11}$ is hydrogen, $C_{1-3}$ alkyl, amino, $C_{1-3}$ alkylamino or di($C_{1-3}$ alkyl)amino; A is

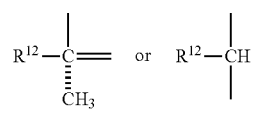

in which $R^{12}$ is hydrogen or hydroxy; B is $CHR^{13}$ in which $R^{13}$ is hydrogen or hydroxy; and a, b, c and d represent single bonds, one of a, b, c or d represents a double bond, both a and c or both b and d represent double bonds provided that when a is a double bond, A is

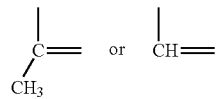

and when d is a double bond, B is

and Z is hydrogen, $C_{1-5}$ alkyl or $C_{1-5}$ alkyl substituted with a member of the group consisting of phenyl, dimethyl amino or acetylamino; and pharmaceutically acceptable salts of the compounds of the Formula XIV in which Z is hydrogen.

In some embodiments, the anti-methanogenic lovastatin analog or derivative may be as described in U.S. Pat. No. 4,771,071, the entire contents of which are incorporated by reference herein (including, by way of illustration, disclosures of specific compounds and synthetic schemes) and may be of formulae:

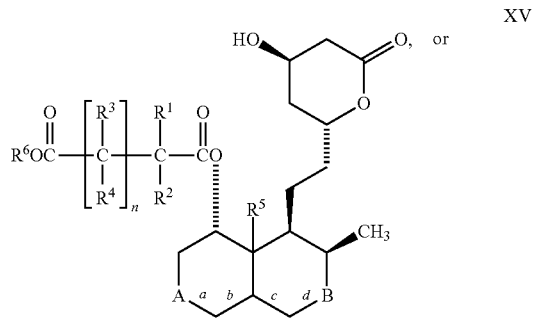

XV

-continued

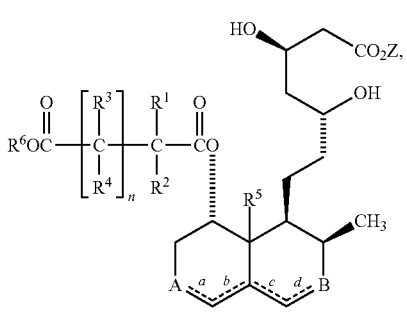

XVI wherein, n is 0 to 5; $R^1$ is $C_{1-3}$ alkyl; $R^2$ is hydrogen or $C_{1-3}$ alkyl; $R^3$ and $R^4$ independently are hydrogen, $C_{1-3}$ alkyl, $C_{3-7}$ cycloalkyl, phenyl or substituted phenyl in which the substituents are X and Y and when n is 2 to 5, each of the $R^3$s and $R^4$s are independently hydrogen, $C_{1-3}$ alkyl, $C_{3-7}$ cycloalkyl or only one of the $R^3$s and $R^4$s is phenyl or substituted phenyl; $R^5$ is hydrogen or hydroxy; $R^6$ is hydrogen or $C_1$-3 alkyl; A is

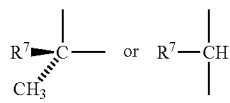

in which $R^7$ is hydrogen or hydroxy; B is

in which $R^8$ is hydrogen or hydroxy; and a, b, c and d represent single bonds, one of a, b, c or d represents a double bond, or both a and c or both b and d represent double bonds provided that when a is a double bond, A is

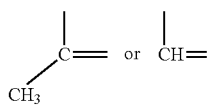

and when d is a double bond, B is

and X and Y independently are hydrogen, halogen, trifluoromethyl, $C_{1-3}$ alkyl, nitro, cyano or a group selected from: (a) $R^9O(CH_2)_m$ in which m is 0 to 3 and $R^9$ is hydrogen, $C_{1-3}$ alkyl or hydroxy-$C_{1-3}$ alkyl; (b)

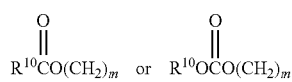

in which $R^{10}$ is hydrogen, alkyl, hydroxy-$C_{2-3}$ alkyl, phenyl, naphthyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{2-3}$ alkylamino-$C_{1-3}$ alkyl or di(hydroxy-$C_{2-3}$ alkyl)amino-$C_{1-3}$ alkyl; (c)

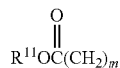

in which $R^{11}$ is hydrogen, $C_{1-3}$ alkyl, hydroxy-$C_{1-3}$ alkyl, $C_{1-3}$ alkoxy-$C_{1-3}$ alkyl, phenyl or naphthyl; (d) $R^{12}R^{13}N(CH_2)_m$,

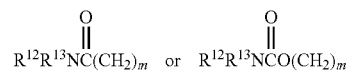

in which $R^{12}$ and $R^{13}$ independently are hydrogen, $C_{1-3}$ alkyl, hydroxy-$C_{2-3}$ alkyl or together with the nitrogen atom to which they are attached form a heterocycle group selected from piperidinyl, pyrrolidinyl, piperazinyl, morpholinyl or thiomorpholinyl; (e) $R^{14}S(O)_p (CH_2)_m$ in which p is 0 to 2 and $R^{14}$ is hydrogen, $C_{1-3}$ alkyl, amino, $C_{1-3}$ alkylamino or di($C_{1-3}$ alkyl)amino; Z is hydrogen, $C_{1-5}$ alkyl or $C_{1-5}$ alkyl substituted with a member of the group consisting of phenyl, dimethylamino or acetylamino; and pharmaceutically acceptable salts of the compounds of the Formula XVI in which Z is hydrogen.

In certain embodiments, the anti-methanogenic lovastatin analog or derivative may have a hydroxymethyl group, acyloxymethyl group, carbamoyloxymethyl group, a carboxy group, an alkoxycarbonyl group or a carbamoyl group substituted on the 6-position of the polyhydronaphthyl moiety as described in, for example, U.S. Pat. Nos. 4,940,727, 4,841,074, 4,894,465, 4,894,466, 4,855,456, RE36520, RE36481, and 5,116,870, the entire contents of which are incorporated by reference herein (including, by way of illustration, disclosures of specific compounds and synthetic schemes). In various embodiments, the anti-methanogenic lovastatin analog or derivative may possess a substituent in the 6-position in either the 6α or 6β stereochemical position.

In an embodiment, the anti-methanogenic lovastatin analog or derivative may have a hydroxyalkyl group, acyloxyalkyl or carbamoyloxyalkyl group, for instance as described in U.S. Pat. No. 4,940,727, the entire contents of which are incorporated by reference herein (including, by way of illustration, disclosures of specific compounds and synthetic schemes) and may be of formulae:

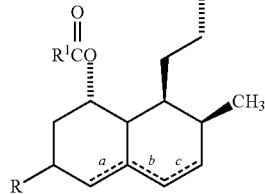

XVII

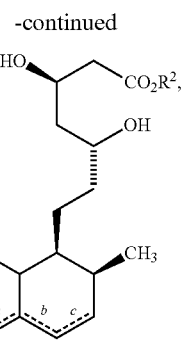

XVIII wherein, R is

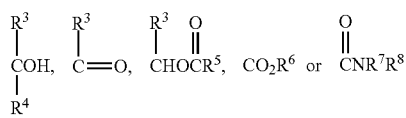

R¹ and R⁵ are independently: (1) $C_{1-10}$ alkyl; (2) substituted $C_{1-10}$ alkyl in which one or more substituent(s) is: halogen, hydroxy, $C_{1-10}$ alkoxy, $C_{1-5}$ alkoxycarbonyl, $C_{1-5}$ acyloxy, $C_{3-8}$ cycloalkyl, phenyl, substituted phenyl in which the substituents are X and Y, $C_{1-10}$ alkylS(O)$_n$ in which n is 0 to 2, $C_{3-8}$ cycloalkylS(O)$_n$, phenylS(O)$_n$, substituted phenylS(O)$_n$ in which the substituents are X and Y, and oxo; (3) $C_{1-10}$ alkoxy; (4) $C_{2-10}$ alkenyl; (5) $C_{3-8}$ cycloalkyl; (6) substituted $C_{3-8}$ cycloalkyl in which one substituent is: $C_{1-10}$ alkyl, substituted $C_{1-10}$ alkyl in which the substituent is: halogen, hydroxy, $C_{1-10}$ alkoxy, $C_{1-5}$ alkoxycarbonyl, $C_{1-5}$ acyloxy, phenyl, substituted phenyl in which the substituents are X and Y, $C_{1-10}$ alkylS(O)$_n$, $C_{3-8}$ cycloalkylS-(C)$_n$, phenylS(O)$_n$, substituted phenylS(C)$_n$ in which the substituents are X and Y, and oxo, $C_{1-10}$ alkylS (O)$_n$, $C_{3-8}$ cycloalkylS(O)$_n$, phenylS(O)$_n$, substituted phenylS(O)$_n$ in which the substituents are X and Y, halogen, hydroxy, $C_{1-10}$ alkoxy, $C_{1-5}$ alkoxycarbonyl, $C_{1-5}$ acyloxy, phenyl, and substituted phenyl in which the substituents are X and Y; (7) phenyl; (8) substituted phenyl in which the substituents are X and Y; (9) amino; (10) $C_{1-5}$ alkyl amino; (11) di($C_{1-5}$ alkyl)amino; (12) phenylamino; (13) substituted phenylamino in which the substituents are X and Y; (14) phenyl $C_{1-10}$ alkylamino; (15) substituted phenyl $C_{1-10}$ alkylamino in which the substituents are X and Y; (16) a member selected from: piperidinyl, pyrrolidinyl, piperazinyl, morpholinyl, and thiomorpholinyl; and (17) R⁹S in which R⁹ is: $C_{1-10}$ alkyl, phenyl, and substituted phenyl in which the substituents are X and Y; R² and R⁶ are independently (1) hydrogen; (2) $C_{1-5}$ alkyl; (3) substituted $C_{1-5}$ alkyl in which the substituent is phenyl, dimethylamino, and acetylamino, and (4) 2,3-dihydroxypropyl; R³ and R⁴ are independently: (1) hydrogen; (2) $C_{1-10}$ alkyl; (3) substituted $C_1$-10 alkyl in which one or more substituent(s) is halogen, hydroxy, $C_{1-10}$ alkoxy, $C_{1-5}$ alkoxycarbonyl, $C_{1-5}$ acyloxy, $C_{3-8}$ cycloalkyl, phenyl, substituted phenyl in which the substituents are X and Y, $C_{1-10}$ alkylS(O)$_n$, $C_{3-8}$ cycloalkylS(C)$_n$, phenylS(C)$_n$, substituted phenylS(C)$_n$ in which the substituents are X and Y, and oxo; (4) $C_{2-10}$ alkenyl; (5) substituted $C_{2-10}$ alkenyl in which one or more substituent(s) is: halogen, hydroxy, $C_{1-10}$ alkoxy, $C_{1-5}$ alkoxycarbonyl, $C_{1-5}$ acyloxy, $C_{3-8}$ cycloalkyl, phenyl, substituted phenyl in which the substituents are X and Y, $C_{1-10}$ alkylS(O)$_n$, $C_{3-8}$ cycloalkylS(C)$_n$, phenylS(C)$_n$, substituted phenylS(C)$_n$ in which the substituents are X and Y, and oxo; (6) $C_{3-8}$ cycloalkyl; (7) substituted $C_{3-8}$ cycloalkyl in which one substituent is: $C_{1-10}$ alkyl, substituted $C_{1-10}$ alkyl in which the substituent is: halogen, hydroxy, $C_{1-10}$ alkoxy, $C_{1-5}$ alkoxycarbonyl, $C_{1-5}$ acyloxy, phenyl, substituted phenyl in which the substituents are X and Y, $C_{1-10}$ alkylS(O)$_n$, $C_{3-8}$ cycloalkylS(O)$_n$, phenylS(O)$_n$, substituted phenylS(O)$_n$ in which the substituents are X and Y, and oxo, $C_{1-10}$ alkylS(O)$_n$, $C_{3-8}$ cycloalkylS(O)$_n$, phenylS(O)$_n$, substituted phenylS(O)$_n$ in which the substituents are X and Y, halogen, hydroxy, $C_{1-10}$ alkoxy, $C_{1-5}$ alkoxycarbonyl, $C_{1-5}$ acyloxy, phenyl, and substituted phenyl in which the substituents are X and Y; (8) phenyl; (9) substituted phenyl in which the substituents are X and Y; R⁷ and R⁸ are independently: (1) hydrogen; (2) $C_1$-10 alkyl; (3) substituted $C_1$-10 alkyl in which one or more substituent(s) is halogen, hydroxy, $C_{1-10}$ alkoxy, $C_{1-10}$ alkoxycarbonyl, $C_{1-5}$ acyloxy, $C_{3-8}$ cycloalkyl, phenyl, substituted phenyl in which the substituents are X and Y, $C_{1-10}$ alkyl S(O)$_n$ in which n is 0 to 2, $C_{3-8}$ cycloalkyl S(O)$_n$, phenyl S(O)$_n$; substituted phenyl S(O)$_n$ in which the substituents are X and Y, and oxo; (4) $C_{2-10}$ alkenyl; (5) $C_{3-8}$ cycloalkyl; (6) aminocarbonyl; (7) substituted aminocarbonyl in which one or more substituent(s) is $C_{1-5}$ alkyl, $C_{3-8}$ cycloalkyl, phenyl, substituted phenyl in which the substituents are X and Y; (8) phenyl; (9) substituted phenyl in which the substituents are X and Y; (10) $C_{1-10}$ alkylcarbonyl; (11) $C_{3-8}$ cycloalkylcarbonyl; (12) phenylcarbonyl; (13) substituted phenylcarbonyl in which the substituents are X and Y; and (14) a nitrogen-containing heterocyclic group selected from piperidinyl, pyrrolidinyl, piperazinyl, morpholinyl and thiomorpholinyl; and X and Y independently are hydrogen, halogen, trifluoromethyl, $C_1$-3 alkyl, nitro, cyano or a group selected from: (1) $R^{10}O(CH_2)_m$ in which m is 0 to 3 and $R^{10}$ is hydrogen, $C_{1-3}$ alkyl or hydroxy-$C_{2-3}$ alkyl; (2)

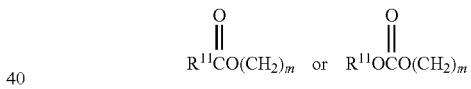

in which $R^{11}$ is hydrogen, $C_{1-3}$ alkyl, hydroxy-$C_{2-3}$ alkyl, phenyl, naphthyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{2-3}$ alkylamino-$C_{1-3}$ alkyl or di(hydroxy-$C_{2-3}$ alkyl) amino-$C_{1-3}$ alkyl; (3)

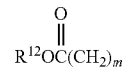

in which $R^{12}$ is hydrogen, $C_{1-3}$ alkyl, hydroxy-$C_{2-3}$ alkyl, $C_{1-3}$ alkoxy-$C_{1-3}$ alkyl, phenyl or naphthyl; (4)

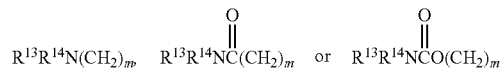

in which $R^{13}$ and $R^{14}$ independently are hydrogen, $C_{1-3}$ alkyl, hydroxy-$C_{2-3}$ alkyl or together with the nitrogen atom to which they are attached form a heterocyclic group selected from piperidinyl, pyrrolidinyl, piperazinyl, morpholinyl or thiomorpholinyl; (5) $R^{15}S(C)_n (CH_2)_m$ in which $R^{15}$ is hydrogen, $C_{1-3}$ alkyl, amino, $C_{1-3}$ alkylamino or di($C_{1-3}$ alkyl)amino; and a, b and c each represent single bonds or one of a, b and c represents a double bond or both a and c represent double bonds; or a pharmaceutically acceptable salt thereof.

In certain embodiments, the anti-methanogenic lovastatin analog or derivative may have a methyl group in the 6-position in the 6β stereochemical position as described, for example, in U.S. patent application Ser. No. 07/092,354 filed Sep. 2, 1987, the entire contents of which are incorporated by reference herein (including, by way of illustration, disclosures of specific compounds and synthetic schemes).

In certain embodiments, the anti-methanogenic lovastatin analog or derivative may have contain gem-disubstitution at the 6,6 positions of the polyhydronaphthyl moiety as described, for example, in U.S. Pat. No. 4,866,090, the entire contents of which are incorporated by reference herein (including, by way of illustration, disclosures of specific compounds and synthetic schemes). For example, the anti-methanogenic lovastatin analog or derivative may have the formula

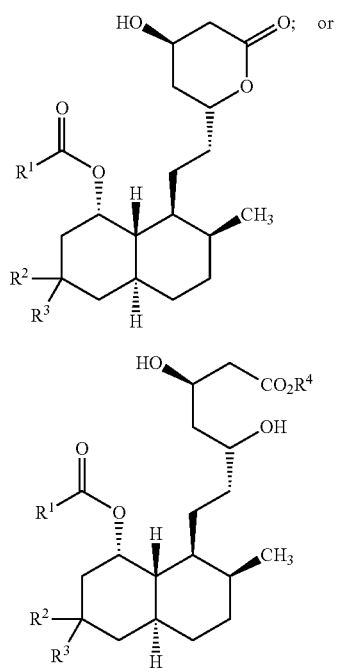

XIX

XX wherein, $R^1$ is selected from: (1) $C_{1-10}$ alkyl; (2) substituted $C_{1-10}$ alkyl in which one or more substituent(s) is selected from (a) halogen, (b) hydroxy, (c) $C_{1-10}$ alkoxy, (d) $C_{1-5}$ alkoxycarbonyl, (e) $C_{1-5}$ acyloxy, (f) $C_{3-8}$ cycloalkyl, (g) phenyl, (h) substituted phenyl in which the substituents are X and Y, (i) $C_{1-10}$ alkylS$(0)_n$ in which n is 0 to 2, (j) $C_{3-8}$ cycloalkylS$(O)_n$, (k) phenylS$(O)_n$, (l) substituted phenylS$(O)_n$ in which the substituents are X and Y, and (m) oxo; (3) $C_{1-10}$ alkoxy; (4) $C_{2-10}$ alkenyl; (5) $C_{3-8}$ cycloalkyl; (6) substituted $C_{3-8}$ cycloalkyl in which one substituent is selected from (a) $C_{1-10}$ alkyl (b) substituted $C_{1-10}$ alkyl in which the substituent is selected from (i) halogen, (ii) hydroxy, (iii) $C_{1-10}$ alkoxy, (iv) $C_{1-5}$ alk oxycarbonyl, (v) $C_{1-5}$ acyloxy, (vi) phenyl, (vii) substituted phenyl in which the substituents are X and Y (viii) $C_{1-10}$ alkylS$(O)_n$, (ix) $C_{3-8}$ cycloalkylS$(O)_n$, (x) phenylS$(O)_n$, (xi) substituted phenylS$(O)_n$ in which the substituents are X and Y, and (xii) oxo, (c) $C_{1-10}$ alkylS$(O)_n$, (d) $C_{3-8}$ cycloalkylS$(0)_n$, (e) phenylS$(0)_n$, (f) substituted phenylS$(0)_n$ in which the substituents are X and Y, (g) halogen, (h) hydroxy, (i) $C_{1-10}$ alkoxy, (j) $C_{1-5}$ alkoxycarbonyl, (k) $C_{1-5}$ acyloxy, (l) phenyl, and (m) substituted phenyl in which the substituents are X and Y; (7) phenyl; (8) substituted phenyl in which the substituents are X and Y; (9) amino; (10) $C_{1-5}$ alkylamino; (11) di($C_{1-5}$ alkyl)amino; (12) phenylamino; (13) substituted phenylamino in which the substituents are X and Y; (14) phenyl $C_{1-10}$ alkylamino; (15) substituted phenyl $C_{1-10}$ alkylamino in which the substituents are X and Y; (16) a member selected from (a) piperidinyl, (b) pyrrolidinyl, (c) piperazinyl, (d) morpholinyl, and (e) thiomorpholinyl; and (17) $R^6S$ in which $R^6$ is selected from (a) $C_{1-10}$ alkyl, (b) phenyl, and (c) substituted phenyl in which the substituents are X and Y; $R^2$ and $R^3$ are independently selected from: (1) $C_{1-10}$ alkyl; and (2) substituted $C_{1-10}$ alkyl in which one or more substituent(s) is selected from (a) halogen, (b) hydroxy, (c) $C_{1-10}$ alkoxy, (d) $C_{1-5}$ alkoxycarbonyl, (e) $C_{1-5}$ acyloxy, (f) $C_{3-8}$ cycloalkyl, (g) phenyl, or (3) together with the carbon atom to which they are attached form a $C_{3-8}$ carbocyclic ring; $R^4$ is selected from: (1) hydrogen; (2) $C_{1-5}$ alkyl; (3) substituted $C_{1-5}$alkyl in which the substituent is selected from (a) phenyl, (b) dimethylamino, and (c) acetylamino, and (4) 2,3-dihydroxypropyl; X and Y independently are hydrogen, halogen, trifluoromethyl, $C_{1-3}$ alkyl, nitro, cyano or group selected from: (1) $R^8O(CH_2)_m$ in which m is 0 to 3 and $R^8$ is hydrogen, $C_{1-3}$ alkyl or hydroxy $C_{2-3}$ alkyl; (2)

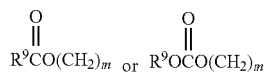

in which $R^9$ is hydrogen, $C_{1-3}$ alkyl, hydroxy $C_{2-3}$ alkyl, phenyl, naphthyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy $C_{2-3}$ alkylamino-$C_{1-3}$ alkyl or di(hydroxy-$C_{2-3}$ alkyl) amino-$C_{1-3}$ alkyl; (3)

in which $R^{10}$ is hydrogen, $C_{1-3}$ alkyl, hydroxy-$C_{2-3}$ alkyl, $C_{1-3}$ alkoxy $C_{1-3}$ alkyl, phenyl or naphthyl; (4)

in which $R^{11}$ and $R^{12}$ independently are hydrogen, $C_{1-3}$ alkyl, hydroxy-$C_{2-3}$ alkyl or together with the nitrogen atom to which they are attached form a heterocyclic group selected from piperidinyl, pyrrolidinyl, piperazinyl, morpholinyl or thiomorpholinyl; (5) $R^{13}S(0)_n$ $(CH_2)_m$ in which $R^{13}$ is hydrogen, $C_{1-3}$ alkyl, amino, $C_{1-3}$ alkylamino or di($C_{1-3}$ alkyl)amino; or a pharmaceutically acceptable salt thereof.

In certain embodiments, the anti-methanogenic lovastatin analog or derivative may have contain two double bonds in the 4,4a- and 5,6-positions or one double bond in the 5,6-position of the polyhydronaphthyl moiety as described, for example, in U.S. Pat. No. 4,857,547, the entire contents of which are incorporated by reference herein (including, by way of illustration, disclosures of specific compounds and synthetic schemes). For example, the anti-methanogenic lovastatin analog or derivative may have the formula:

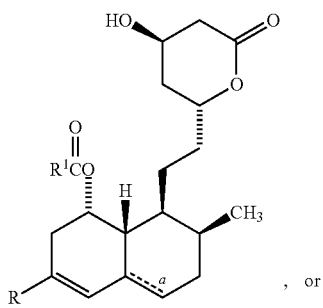

XXI

, or

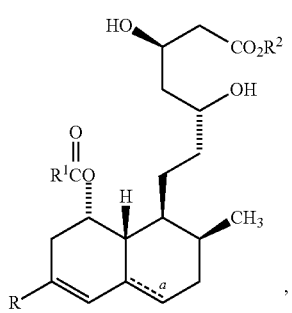

XXII

, wherein, R is $CH_2OH$,

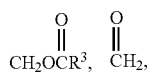

or $CO_2R^4$; $R^1$ and $R^3$ are independently selected from: (1) $C_{1-10}$ alkyl; (2) substituted $C_{1-10}$ alkyl in which one or more substituent(s) is selected from: (a) halogen, (b) hydroxy, (c) $C_{1-10}$ alkoxy, (d) $C_{1-5}$ alkoxycarbonyl, (e) $C_{1-5}$ acyloxy, (f) $C_{3-5}$ cycloalkyl, (g) phenyl, (h) substituted phenyl in which the substituents are X and Y, and (i) oxo; (3) $C_{3-8}$ cycloalkyl; (4) substituted $C_{3-8}$ cycloalkyl in which one substituent is selected from: (a) $C_1$-10 alkyl, (b) substituted $C_1$-10 alkyl in which the substituent is selected from: (I) halogen, (II) hydroxy, (ill) $C_{1-10}$ alkoxy (iv) $C_{1-5}$ acyloxy, (v) $C_{1-5}$ alkoxycarbonyl, (vi) phenyl, (vii) substituted phenyl in which the substituents are X and Y, and (viii) oxo, (c) halogen, (d) hydroxy, (e) $C_{1-10}$ alkoxy, (f) $C_{1-5}$ alkoxycarbonyl, (g) $C_{1-5}$ acyloxy, (h) phenyl, (I) substituted phenyl in which the substituents are X and Y; (5) phenylamino; (6) substituted phenylamino in which the substituents are X and Y; (7) phenyl $C_{1-10}$ alkylamino; and (8) substituted phenyl $C_{1-10}$ alkylamino in which the substituents are X and Y. $R^2$ and $R^4$ are independently selected from: (a) hydrogen; (b) $C_1$-5 alkyl; (c) substituted-$C_1$-5 alkyl in which the substituent is selected from PA4 (i) phenyl, PA4 (ii) dimethyl amino, and PA4 (iii) acetylamino; and (d) 2,3-dihydroxypropyl; X and Y independently are hydrogen, halogen, trifluoromethyl, $C_1$-3 alkyl, nitro, cyano or group selected from: (1) $R^8O$ $(CH_2)_m$ in which m is 0 to 3 and $R^8$ is hydrogen, $C_{1-3}$ alkyl or hydroxy-$C_{2-3}$ alkyl; (2)

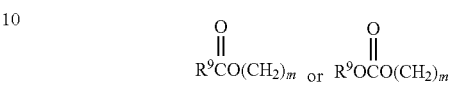

in which $R^9$ is hydrogen, $C_{1-3}$ alkyl, hydroxy-$C_{2-3}$ alkyl, phenyl, naphthyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{2-3}$ alkylamino-$C_{1-3}$ alkyl or di(hydroxy-$C_{2-3}$ alkyl)amino-$C_{1-3}$ alkyl; (3)

in which $R^{10}$ is hydrogen, $C_{1-3}$ alkyl, hydroxy-$C_{2-3}$ alkyl, $C_{1-3}$ alkoxy-$C_{1-3}$ alkyl, phenyl or naphthyl; (4) $R^{11}R^{12}N$ $(CH_2)_m$,

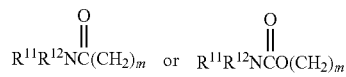

in which $R^{11}$ and $R^{12}$ independently are hydrogen, $C_{1-3}$ alkyl, hydroxy-$C_{2-3}$ alkyl or together with the nitrogen atom to which they are attached form a heterocyclic group selected from piperidinyl, pyrrolidinyl, piperazinyl, morpholinyl or thiomorpholinyl; (5) $R^{13}S(O)_n$ $(CH_2)m$ in which $R^{13}$ is hydrogen, $C_{1-3}$ alkyl, amino, $C_{1-3}$ alkylamino or di($C_1$-3 alkyl)amino; a represents a single bond or a double bond; or a pharmaceutically acceptable salt thereof.

In certain embodiments, the anti-methanogenic lovastatin analog or derivative may have contain an aminoalkyl group, or substituted aminoalkyl group, on the 6-position of the polyhydronaphthyl moiety as described, for example, in U.S. Pat. No. 4,857,546 (including, by way of illustration, disclosures of specific compounds and synthetic schemes), the entire contents of which are incorporated by reference herein. For example, the anti-methanogenic lovastatin analog or derivative may have the formula:

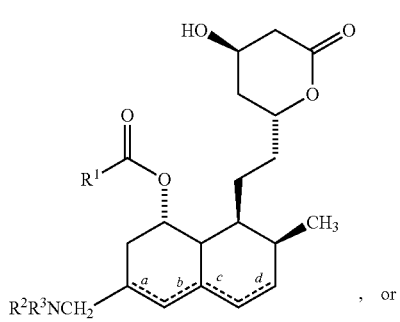

XXIII

, or

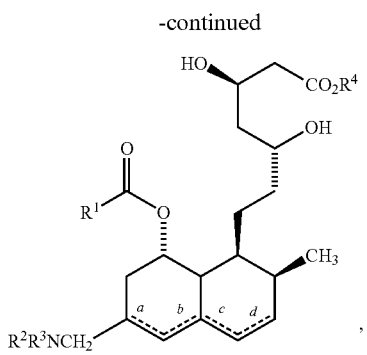

XXIV wherein, R¹ is selected from: (1) $C_{1-10}$ alkyl; (2) substituted $C_{1-10}$ alkyl in which one or more substituent(s) is selected from: (a) halogen, (b) hydroxy, (c) $C_{1-10}$ alkoxy, (d) $C_{1-5}$ alkoxycarbonyl, (e) $C_{1-5}$ acyloxy, (f) $C_{3-8}$ cycloalkyl, (g) phenyl, (h) substituted phenyl in which the substituents are X and Y, (I) $C_{1-10}$ alkylS(O)$_n$ in which n is 0 to 2, (j) $C_{3-8}$ cycloalkyl(O)$_n$, (k) phenylS(O)$_n$, (l) substituted phenylS(O)$_n$ in which the substituents are X and Y, and (m) oxo; (3) $C_{1-10}$ alkoxy; (4) $C_{2-10}$ alkenyl; (5) $C_{3-8}$ cycloalkyl; (6) substituted $C_{3-8}$ cycloalkyl in which one substituent is selected from (a) $C_{1-10}$ alkyl (b) substituted $C_{1-10}$ alkyl in which the substituent is selected from: (i) halogen, (ii) hydroxy, (iii) $C_{1-10}$ alkoxy, (iv) $C_{1-5}$ alkoxycarbonyl, (v) $C_{1-5}$ acyloxy (vi) phenyl, (vii) substituted phenyl in which the substituents are X and Y, (viii) $C_{1-10}$ alkylS(O)$_n$, (lx) $C_{3-8}$ cycloalkylS(O)$_n$, (x) phenylS(O)$_n$, (xi) substituted phenylS(O)$_n$ in which the substituents are X and Y, and (xii) oxo, (c) $C_{1-10}$ alkylS(O)$_n$ (d) $C_{3-8}$ cycloalkylS(O)$_n$, (e) phenylS(O)$_n$, (f) substituted phenylS(O)$_n$ in which the substituents are X and Y, (g) halogen, (h) hydroxy, (i) $C_{1-10}$ alkoxy, (j) $C_{1-5}$ alkoxycarbonyl, (k) $C_{1-5}$ acyloxy, (l) phenyl, and (m) substituted phenyl in which the substituents are X and Y; (7) phenyl; (8) substituted phenyl in which the substituents are X and Y; (9) amino; (10) $C_{1-5}$ alkylamino; (11) di($C_{1-5}$ alkyl)amino; (12) phenylamino; (13) substituted phenylamino in which the substituents are X and Y; (14) phenyl $C_{1-10}$ alkylamino; (15) substituted phenyl $C_{1-10}$ alkylamino in which the substituents are X and Y; (16) a member selected from: (a) piperidinyl, (b) pyrrolidinyl, (c) piperazinyl, (d) morpholinyl, and (e) thiomorpholinyl; and (17) R⁶S in which R⁶ is selected from: (a) $C_{1-10}$ alkyl, (b) phenyl, and (c) substituted phenyl in which the substituents are X and Y; R² and R³ are independently selected from: (1) hydrogen; (2) $C_{1-10}$ alkyl; (3) substituted $C_{1-10}$ alkyl in which one or more substituent(s) is selected from: (a) halogen, (b) hydroxy, (c) $C_{1-10}$ alkoxy, (d) $C_{1-5}$ alkoxycarbonyl, (e) $C_{1-5}$ acyloxy, (f) $C_{3-8}$ cycloalkyl, (g) phenyl, (h) substituted phenyl in which the substituents are X and Y, and (i) oxo; (4) $C_{1-10}$ acyl; (5) substituted $C_{1-10}$ acyl in which one or more substituent(s) is selected from (a) halogen, (b) hydroxy, (c) $C_{1-10}$ alkoxy, (d) $C_{1-5}$ alkoxycarbonyl, (e) $C_{1-5}$ acyloxy, (f) $C_{3-8}$ cycloalkyl, (g) phenyl, (h) substituted phenyl in which the substituents are X and Y, and (I) oxo; (6) phenylcarbonyl; (7) substituted phenylcarbonyl in which the substituents are X and Y; (8) $C_{1-5}$ alkylaminocarbonyl; (9) di($C_{1-5}$ alkyl)aminocarbonyl; (10) phenylaminocarbonyl; (11) substituted phenylaminocarbonyl in which the substituents are X and Y; (12) phenyl $C_{1-10}$ alkylaminocarbonyl; (13) substituted phenyl $C_{1-10}$ alkylaminocarbonyl in which the substituents are X and Y; R⁴ is selected from: (1) hydrogen; (2) $C_{1-5}$ alkyl; (3) substituted $C_{1-5}$ alkyl in which the substituent is selected from: (a) phenyl, (b) dimethylamino, and (c) acetylamino, and (4) 2,3-dihydroxypropyl; X and Y independently are hydrogen, halogen, trifluoromethyl, $C_{1-3}$ alkyl, nitro, cyano or group selected from: (1) $R^8O(CH_2)_m$ in which m is 0 to 3 and R⁸ is hydrogen, $C_{1-3}$ alkyl or hydroxy-$C_{2-3}$ alkyl; (2)

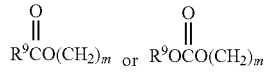

in which R⁹ is hydrogen, $C_{1-3}$ alkyl, hydroxy-$C_{2-3}$ alkyl, phenyl, naphthyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{2-3}$ alkylamino-$C_{1-3}$ alkyl or di(hydroxy-$C_{2-3}$ alkyl; amino-$C_{1-3}$ alkyl; (3)

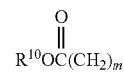

in which $R^{10}$ is hydrogen, $C_{1-3}$ alkYl, hydroxy-$C_{2-3}$ alkyl, $C_{1-3}$ alkoxy-$C_{1-3}$ alkyl, phenyl or naphthyl; (4)

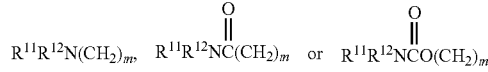

in which $R^{11}$ and $R^{12}$ independently are hydrogen, $C_{1-3}$ alkyl, hydroxy-$C_{2-3}$ alkyl or together with the nitrogen atom to which they are attached form a heterocyclic group selected from piperidinyl, pyrrolidinyl, piperazinyl, morpholinyl or thiomorpholinyl; (5) $R^{13}S(C)_n (CH_2)_m$ in which $R^{13}$ is hydrogen, $C_{1-3}$ alkyl, amino, $C_{1-3}$ alkylamino or di($C_{1-3}$ alkyl)amino; and a, b, c and d each represent single bonds or one of a, b, c and d represents a double bond or both a and c or b and d represent double bonds; or a pharmaceutically acceptable salt thereof.

In certain embodiments, the anti-methanogenic lovastatin analog or derivative may be a 5'-oxygenated derivative of lovastatin and analog thereof at the 8'-acyl side chain and 6'-position of the polyhydronaphthyl ring as described, for example, in U.S. Pat. No. 4,921,974, the entire contents of which are incorporated by reference herein (including, by way of illustration, disclosures of specific compounds and synthetic schemes). For example, the anti-methanogenic lovastatin analog or derivative may have the formula:

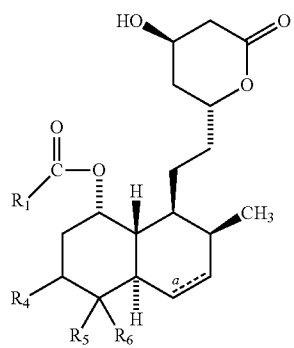

XXV or pharmaceutically acceptable salts thereof, wherein, $R_1$ is selected from: (1) $C_{1-10}$ alkyl; (2) substituted $C_{1-10}$ alkyl in which one or more substituent(s) is selected from: (a) halogen, (b) hydroxy, (c) $C_{1-10}$ alkoxy, (d) $C_{1-5}$ alkoxycarbonyl, (e) $C_{1-5}$ acyloxy, (f) $C_{3-8}$ cycloalkyl, (g) phenyl, (h) substituted phenyl in which the substituents are X and Y, (i) $C_{1-10}$ alkylS(0)$_n$ in which n is 0 to 2, (j) $C_{3-8}$ cycloalkylS(0)$_n$, (k) phenylS(0)$_n$, (l) substituted phenylS(0)$_n$, in which the substituents are X and Y, and (m) oxo; (3) $C_{1-10}$ alkoxy; (4) $C_{2-10}$ alkenyl; (5) $C_{3-8}$ cycloalkyl; (6) substituted $C_{3-8}$ cycloalkyl in which one substituent is selected from (a) $C_{1-10}$ alkyl (b) substituted $C_{1-10}$ alkyl in which the substituent is selected from (i) halogen, (ii) hydroxy, (iii) $C_{1-10}$ alkoxy, (iv) $C_{1-5}$ alkoxycarbonyl, (v) $C_{1-5}$ acyloxy, (vi) phenyl, (vii) substituted phenyl in which the substituents are X and Y (viii) $C_{1-10}$ alkylS(0)$_n$, (ix) $C_{3-8}$ cycloalkylS(0)$_n$, (x) phenylS (0)$_n$, (xi) substituted phenylS(0)$_n$ in which the substituents are X and Y, and (xii) oxo, (c) $C_{1-10}$ alkylS(0)$_n$, (d) $C_{3-8}$ cycloalkylS(0)$_n$, (e) phenylS(0)$_n$, (f) substituted phenylS(0)$_n$ in which the substituents are X anti Y, (g) halogen, (h) hydroxy, (i) $C_{1-10}$ alkoxy, (j) $C_{1-5}$ alkoxycarbonyl, (k) $C_{1-5}$ acyloxy, (l) phenyl, and (m) substituted phenyl in which the substituents are X and Y; (7) phenyl; (8) substituted phenyl in which the substituents are X and Y; (9) amino; (10) On alkylamino; (11) d; ($C_{1-5}$ alkyl)amino; (12) phenyl amino; (13) substituted phenylamino in which the substituents are X and Y; (14) phenyl $C_{1-10}$ alkylamino; (15) substituted phenyl $C_{1-10}$ alkylamino in which the substituents are X and Y; (16) a member selected from (a) piperidinyl, (b) pyrrolidinyl, (c) piperazinyl, (d) morpholinyl, and (e) thiomorpholinyl; and (17) $R_5S$ in which $R_5$ is selected from (a) $C_{1-10}$ alkyl, (b) phenyl, and (c) substituted phenyl in which the substituents are X and Y; $R_4$ is; (1) hydrogen; (2) $C_{1-10}$ alkyl; and (3) substituted $C_{1-10}$ alkyl in which one or more substituents is selected from: (a) halogen, (b) hydroxy, (c) $C_{1-10}$ alkoxy (d) $C_{1-5}$ alkoxycarbonyl, (e) $C_{1-5}$ alkylacyloxy, (f) phenylacyloxy, (g) phenoxycarbonyl, (h) phenyl $C_{1-5}$ alkylacyloxy, (i) phenyl $C_{1-5}$ alkoxy, (j) amino, (k) $C_{1-5}$ alkylamino, (l) di($C_{1-5}$ alkyl)amino, (m) phenylamino, (n) substituted phenylamino in which the substituents are X and Y; (o) phenyl $C_{1-5}$ alkylamino, (p) substituted phenyl $C_{1-5}$ alkylamino in which the substituents are X and Y, (q) $C_{3-8}$ cycloalkyl, (r) phenyl, (s) substituted phenyl in which the substituents are X and Y, (t) phenylS(O)$_n$, (u) substituted phenyl S(0)$_n$ in which the substituents are X and Y, (v) phenyl $C_{1-5}$ alkyl S(O)$_n$, (w) $C_{1-5}$ alkylS(O)$_n$; (x) phenylaminoacyloxy, (y) $C_{1-5}$ alkylaminoacyloxy, (z) $C_{1-5}$ alkylacylamino, (aa) di(phenyl$C_{1-5}$ alkyl)phosphonyl (bb) di($C_{1-5}$ alkyl)phosphinyl (4) $R_4$ together with the carbon atom to which it is attached represents a $C_{3-8}$ carbocyclic ring; $R_5$ and $R_6$ independently are H, OH, $OR_7$ or $R_5$ and $R_6$ together with the carbon to which they are attached represent C=O or $R_5$ and $R_6$ together with the carbon to which they are attached represent a carbocyclic ring of 4 to 7 atoms; provided that when $R_5$ is H, $R_6$ is OH or $OR_7$, and when $R_5$ is OH, $R_6$ is H, and when $R_5$ is $OR_7$, $R_6$ is H; $R_7$ is

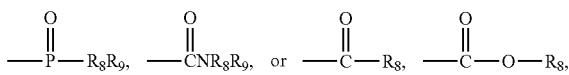

phenyl$C_1$-3 alkyl, $C_1$-5 alkyl; $R_8$ and $R_9$ independently are H, $C_1$-3 alkyl, phenyl$C_1$-3 alkyl or aryl wherein aryl is phenyl naphthyl, pyridyl, furanyl, thienyl or phenyl, naphthyl, pyridyl, furanyl or thienyl substituted with groups X and Y provided that when $R_7$ is

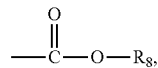

$R_8$ is not H and when $R_7$ is

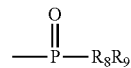

neither $R_8$ nor $R_9$ is H; X and Y are independently selected from: (a) OH, (b) halogen, (c) trifluoromethyl, (d) $C_{1-3}$ alkoxy, (e) $C_{1-3}$ alkylcarbonyloxy, (f) phenylcarbonyloxy, (g) $C_{1-3}$ alkyoxycarbonyl, (h) phenyloxycarbonyl, (i) hydrogen; (j) $C_{1-5}$ alkyl: a is a single bond or a double bond.

In certain embodiments, the anti-methanogenic lovastatin analog or derivative may be a 5-oxygenated derivative of lovastatin and analog thereof wherein position 5 of the polyhydronaphthyl ring is singly or doubly bonded to oxygen or incorporated into a $C_3$-7 carbocyclic ring as described, for example, in U.S. Pat. No. 4,963,538, the entire contents of which are incorporated by reference herein (including, by way of illustration, disclosures of specific compounds and synthetic schemes). For example, the anti-methanogenic lovastatin analog or derivative may have the formula:

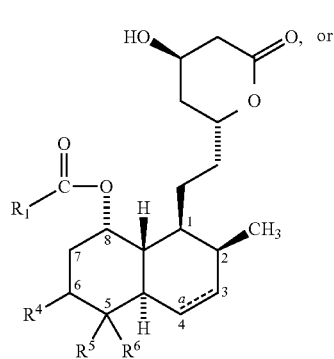

XXVI

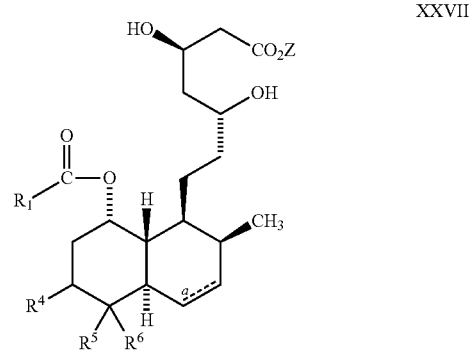

XXVII wherein, R1 is selected from: (1) $C_{1-10}$ alkyl; (2) substituted $C_{1-10}$ alkyl in which one or more substituent(s) is selected from: (a) halogen, (b) hydroxy, (c) $C_{1-10}$ alkoxy, (d) $C_{1-5}$ alkoxycarbonyl, (e) $C_{1-5}$ acyloxy, (f) $C_{3-3}$ cycloalkyl, (g) phenyl, (h) substituted phenyl in which the substituents are X and Y, (i) $C_{1-10}$ alkylS(O)$_n$ in which n is 0 to 2, (j) $C_{3-8}$ cycloalkylS(O)$_n$, (k) phenylS(O)$_n$, (l) substituted phenylS (O)$_n$ in which the substituents are X and Y, and (m) oxo; (3)

$C_{1-10}$ alkoxy; (4) $C_{2-10}$ alkenyl; (5) $C_{3-8}$ cycloalkyl; (6) substituted $C_{3-8}$ cycloalkyl in which one substituent is selected from: (a) $C_{1-10}$ alkyl (b) substituted $C_{1-10}$ alkyl in which the substituent is selected from: (i) halogen, (ii) hydroxy, (ill) $C_{1-10}$ alkoxy, (iv) $C_{1-5}$ alkoxycarbonyl, (v) $C_{1-5}$ acyloxy, (vi) phenyl, (vii) substituted phenyl in which the substituents are X and Y (viii) $C_{1-10}$ alkylS(O)$_n$, (ix) $C_{3-8}$ cycloalkylS(O)$_n$, (x) phenylS(O)$_n$, (xi) substituted phenylS(O)$_n$ in which the substituents are X and Y, and (xii) oxo, (c) $C_{1-10}$ alkylS(O)$_n$, (d) $C_{3-8}$ cycloalkylS(O)$_n$, (e) phenylS(O)$_m$ (f) substituted phenylS(O)$_n$ in which the substituents are X and Y, (g) halogen, (h) hydroxy, (i) $C_{1-10}$ alkoxy, (j) $C_{1-5}$ alkoxycarbonyl, (k) $C_{1-5}$ acyloxy, (l) phenyl, and (m) substituted phenyl in which the substituents are X and Y; (7) phenyl; (8) substituted phenyl in which the substituents are X and Y; (9) amino; (10) $C_{1-5}$ alkylamino; (11) di($C_{1-5}$ alkyl)amino; (12) phenyl amino; (13) substituted phenylamino in which the substituents are X and Y; (14) phenyl $C_{1-10}$ alkylamino; (15) substituted phenyl $C_{1-10}$ alkylamino in which the substituents are X and Y; (16) a member selected from: (a) piperidinyl, (b) pyrrolidinyl, (c) piperazinyl, (d) morpholinyl, and (e) thiomorpholinyl; and (17) $R_{10}$S in which $R_{10}$ is selected from (a) $C_{1-10}$ alkyl, (b) phenyl, and (c) substituted phenyl in which the substituents are X and Y; $R_4$ is: (1) hydrogen; (2) $C_{1-10}$ alkyl; and (3) substituted $C_{1-10}$ alkyl in which one or more substituents is selected from (a) halogen, (b) hydroxy, (c) $C_{1-10}$ alkoxy (d) $C_{1-5}$ alkoxycarbonyl, (e) $C_{1-5}$ alkylacyloxy, (f) phenyl acyloxy, (g) phenoxycarbonyl, (h) phenyl $C_{1-5}$ alkylacyloxy, (i) phenyl $C_{1-5}$ alkoxy, (j) amino, (k) $C_{1-5}$ alkylamino, (l) di($C_{1-5}$ alkyl) amino, (m) phenylamino, (n) substituted phenylamino in which the substituents are X and Y; (o) phenyl $C_{1-5}$ alkylamino, (p) substituted phenyl $C_{1-5}$ alkylamino in which the substituents are X and Y, (q) $C_{3-8}$ cycloalkyl, (r) phenyl, (s) substituted phenyl in which the substituents are X and Y, (t) phenylS(O)$_n$, (u) substituted phenyl S(O)$_n$ in which the substituents are X and Y, (v) phenyl $C_{1-5}$ alkyl S(O)$_n$, (w) $C_{1-5}$ alkylS(O)$_n$; (x) phenylaminoacyloxy, (y) $C_{1-5}$ alkylaminoacyloxy, (z) $C_{1-5}$ alkylacylamino, (aa) di(phenylC-5 alkyl) phosphonyl (bb) di($C_{1-5}$ alkyl)phosphinyl (4) $R_4$ together with the carbon atom to which it is attached represents a $C_{3-8}$ carbocyclic ring; $R_5$ and $R_6$ independently are H, OH, OR$_7$ or $R_5$ and $R_6$ together with the carbon to which they are attached represent C=O or $R_5$ and $R_6$ together with the carbon to which they are attached represent a carbocyclic ring of 3 to 7 atoms; provided that when $R_5$ is H, $R_6$ is OH or OR$_7$, and when $R_5$ is OH, $R_6$ is H, and when $R_5$ is OR$_7$, $R_6$ is H; $R_7$ is

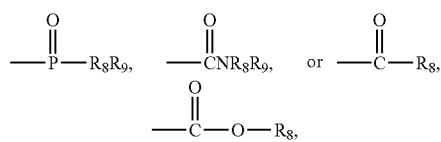

phenylC$_1$-3 alkyl. C$_1$-5 alkyl; $R_8$ and $R_9$ independently are H, $C_1$-3 alkyl, phenylC$_1$-3 alkyl or aryl wherein aryl is phenyl naphthyl, pyridyl, furanyl, thienyl or phenyl, naphthyl, pyridyl, furanyl or thienyl substituted with groups X and Y provided that when $R_7$ is

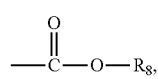

$R_8$ is not H and when $R_7$ is

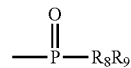

neither $R_8$ nor $R_9$ is H; X and Y are independently selected from: (a) OH, (b) halogen, (c) trifluoromethyl, (d) $C_1$-3 alkoxy, (e) $C_1$-3-alkylcarbonyloxy, (f) phenylcarbonyloxy, (g) $C_{1-3}$ alkoxycarbonyl, (h) phenyloxycarbonyl, (i) hydrogen; (j) $C_{1-5}$ alkyl; Z is selected from: (1) hydrogen; (2) $C_{1-5}$-alkyl; (3) substituted $C_1$-5 alkyl in which the substituent is selected from (a) phenyl, (b) dimethylamino, and (c) acetylamino, and (4) 2,3 hydroxypropyl; Halogen is Cl or F; a is a single bond or a double bond; or a pharmaceutically acceptable salt thereof.

In certain embodiments, the anti-methanogenic lovastatin analog or derivative may be a metabolite of lovastatin which possess a 2,3,5,6,7,8-hexahydronapthyl moiety and a 3-hydroxy group, as described, for example, in U.S. Pat. No. 4,738,982, the entire contents of which are incorporated by reference herein (including, by way of illustration, disclosures of specific compounds and synthetic schemes). For example, the anti-methanogenic lovastatin analog or derivative may have the formula:

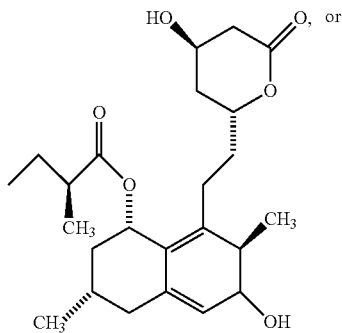

XXVIII

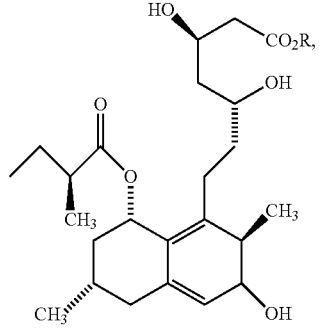

XXIX wherein R is hydrogen, $C_1$-5 alkyl, $C_1$-5 alkyl substituted with a member of the group consisting of phenyl, dimethylamino, or acetylamino, and pharmaceutically acceptable salts of the Formula XXIX in which R is hydrogen.

In certain embodiments, the anti-methanogenic lovastatin analog or derivative may be a metabolite of mevinolin and related compounds which possess a 1,2,7,8,8a-pentahydronaphthyl moiety and a 6-exomethylene group, as described, for example, in U.S. Pat. Nos. 4,782,084 and 4,885,314, the entire contents of which are incorporated by reference herein (including, by way of illustration, disclosures of specific compounds and synthetic schemes). For example, the anti-methanogenic lovastatin analog or derivative may have the formula:

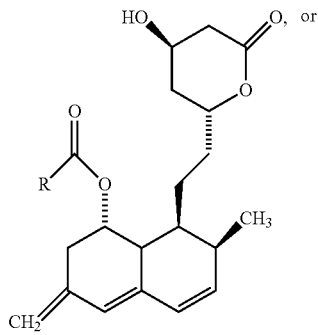

XXX

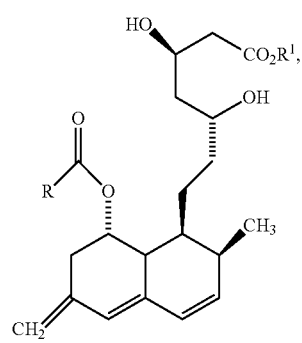

XXXI wherein; R is $C_{1-10}$ alkyl; $R^1$ is hydrogen, $C_{1-5}$ alkyl, $C_{1-5}$ alkyl substituted with a member of the group consisting of phenyl, dimethylamino, or acetylamino, and pharmaceutically acceptable salts of the Formula XXXI in which $R^1$ is hydrogen.

In an embodiment, the anti-methanogenic lovastatin analog or derivative may be a synthetic analog of lovastastin as described, for example, in U.S. Pat. No. 4,654,363, the entire contents of which are incorporated by reference herein (including, by way of illustration, disclosures of specific compounds and synthetic schemes). For example, the anti-methanogenic lovastatin analog or derivative may have the formula:

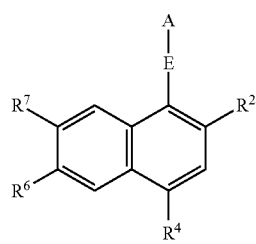

XXXII wherein A is:

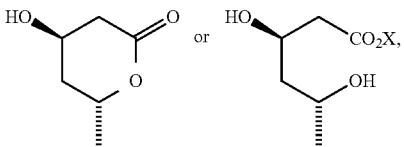

XXX

E is —$CH_2CH_2$— or —CH=CH—; $R^2$ and $R^4$ independently are chloro, fluoro, or $C_{1-3}$ alkyl, especially methyl; $R^6$ is hydrogen or chloro; $R^7$ is hydrogen, chloro or fluoro provided that when $R^6$ is chloro then $R^7$ is hydrogen and when $R^6$ is hydrogen, $R^7$ is chloro or fluoro; X is hydrogen, $C_{1-5}$ alkyl or $C_{1-5}$ alkyl substituted with a member of the group consisting of phenyl, dimethylamino or acetylamino; and pharmaceutically acceptable salts of the compounds of the Formula XXXII in which X is hydrogen.

Additional synthetic anti-methanogenic lovastatin analogs or derivatives are disclosed, for example, in U.S. Pat. Nos. 4,198,425, 4,255,444, 4,604,472, and EP publication No. 0024348, the entire contents of which are incorporated by reference herein (including, by way of illustration, disclosures of specific compounds and synthetic schemes).

In certain embodiments, the anti-methanogenic lovastatin analog or derivative may have a modified lactone ring, as described, for example, in U.S. Pat. No. 6,818,638, the entire contents of which are incorporated by reference herein (including, by way of illustration, disclosures of specific compounds and synthetic schemes). For example, the anti-methanogenic lovastatin analog or derivative may have the formula:

XXXIII wherein, each of a - - - b and α - - - β independently, is either a single bond or a double bond; $R_1$ is —H, —$C_{2-4}$alkyl or —OR, wherein $R_a$ is H, C1-6alkyl optionally substituted by OH or $C_{1-4}$alkoxy, $C_{2-6}$alkenyl or aryl-$C_{1-4}$alkyl; $R_2$ is OH; —O—CO—$R_5$ wherein $R_5$ is $C_{1-8}$alkyl, $C_{3-7}$cycloalkyl, $C_{3-7}$cycloalkyl-$C_{1-4}$alkyl, aryl or aryl-$C_{1-4}$alkyl; or —O—$R_6$ wherein $R_6$ is the residue of an α-amino-acid attached to O through its carbonyl residue or —$CHR_7$—$COR_8$ wherein $R_7$ is H, $C_{1-4}$alkyl, hetero$C_{1-4}$alkyl, $C_{3-7}$cycloalkyl, $C_{3-7}$cycloalkyl-$C_{1-4}$alkyl, aryl or aryl-$C_{1-4}$alkyl and $R_6$ is OH, $C_{1-4}$alkoxy or $NR_9R_{10}$ wherein each of $R_9$ and $R_{10}$ independently is H, $C_{1-4}$alkyl or $R_9$ and $R_{10}$ form together with the nitrogen to which they are bound, a heteroaryl group; $R_3$ is a substituted linear amino alcohol or cyclic carbamate of formula ($c_2$):

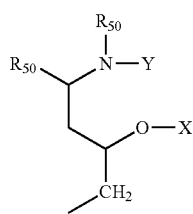

(c2)

wherein each of $R_{50}$, independently is H; $C_{1-8}$alkyl; $C_{3-7}$cycloalkyl; aryl; $C_{3-7}$cycloalkyl-$C_{1-4}$alkyl; aryl-$C_{1-4}$alkyl; heteroaryl; heteroaryl-$C_{1-4}$alkyl; $C_{1-4}$alkylcarbonyl; aryl-carbonyl; heteroaryl-carbonyl; aryl-$C_{1-4}$alkylcarbonyl or heteroaryl-$C_{1-4}$alkyl-carbonyl, and each of $R_{51}$, independently is H; $C_{1-4}$alkyl; hydroxy-$C_{1-4}$alkyl; amino$C_{1-4}$alkyl; $C_{1-4}$alkoxy-$C_{1-4}$alkyl; $C_{1-4}$alkoxy-carbonyl-$C_{1-4}$alkyl wherein $C_{1-4}$alkoxy is optionally substituted by amino, $C_{1-4}$alkylamino or di-($C_{1-4}$alkyl)amino; HOOC—$C_{1-4}$alkyl; or $R_{23}R_{24}$N—CO—$C_{1-4}$alkyl wherein $R_{23}$ is H, $C_{1-4}$alkyl, hydroxy-$C_{1-4}$alkyl, polyhydroxy-$C_{1-8}$alkyl, heteroaryl, heteroaryl-$C_{1-4}$alkyl, amino-$C_{1-4}$alkyl, $C_{1-4}$alkylamino-$C_{1-4}$alkyl, di-($C_{1-4}$alkyl)amino-$C_{1-4}$alkyl or aryl-$C_{1-4}$alkyl and $R_{24}$ is H, $C_{1-4}$alkyl or hydroxy-$C_{1-4}$alkyl, at least one of $R_{50}$ and $R_{51}$ being other than H, each of X and Y is H or X and Y form together each of a - - - b and α - - - β being a single bond when each of $R_{13}$ or $R_{14}$ is OH; and

$R_4$ is H or $OR_{19}$ wherein $R_{19}$ is $C_{1-6}$alkyl, hydroxy-$C_{1-6}$alkyl, $C_{1-4}$alkoxy-$C_{1-6}$alkyl, aryl-$C_{1-4}$alkyl or $C_{1-4}$alkoxy-carbonyl-$C_{1-4}$alkyl. and wherever "aryl" appears as is or in the significances of "aryl-$C_{1-4}$alkyl" in the above definition, it is "phenyl" or "naphthyl" optionally substituted by halogen, OH, $NR_{11}R_{12}$, COOH, $CF_3$, $C_{1-4}$alkoxy, $C_{1-4}$alkyl, hydroxy-$C_{1-4}$alkyl, hydroxy-$C_{1-4}$alkoxy, $C_{1-4}$alkoxy-carbonyl, cyano or $CONR_{11}R_{12}$, each of $R_{11}$ and $R_{12}$ independently being H, $C_{1-4}$alkyl, phenyl, naphthyl, phenyl-$C_{1-4}$alkyl or naphthyl-$C_{1-4}$alkyl or $R_{11}$ and $R_{12}$ together with the nitrogen to which they are bound forming heteroaryl; and wherever "heteroaryl" appears, it is a 5- or 6-membered heteroaryl optionally fused to a benzene ring; in free form or in salt form.

In certain embodiments, the anti-methanogenic lovastatin analog or derivative may be a compound of the following Formula:

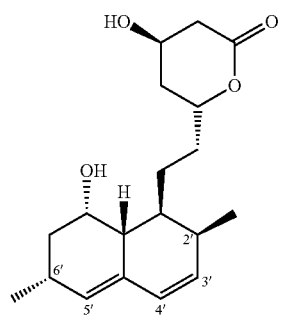

XXXIV and pharmaceutically acceptable salts of the compound.

In certain embodiments, the anti-methanogenic lovastatin analog or derivative may be a compound of the following Formula:

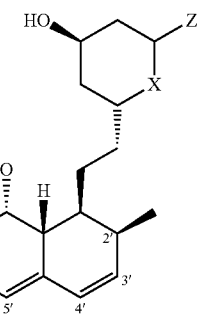

XXXV wherein X is selected from O, N, and S, and Z is selected from hydrogen, substituted or unsubstituted $C_{1-6}$ alkyl, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ alkyl, substituted or unsubstituted $C_{1-10}$ aminoalkyl, substituted or unsubstituted $C_{5-10}$ aryl, substituted or unsubstituted saturated or unsaturated 3-11 member heteroaryl or heteroaryl alkyl containing 1, 2, 3, or 4 heteroatoms selected independently from N, O, S, or $S(O)_2$ or $R_2$ and $R_3$ may be combined with the nitrogen to which they are attached to form a 3, 4, 5, 6, or 7 membered heterocyclein which one or more of the carbons may be substituted with a heteroatom selected from O, N, or S and in which any of the hydrogens of the heterocycle may be substituted with $C_{1-6}$ alkyl, F, Cl, Br, I, cyano, $C_{1-6}$ alkoxy, or $C_{6-10}$ aryloxy, or a stereoisomer thereof, tautomer thereof, solvate thereof, or a pharmaceutically acceptable salt thereof.

In certain embodiments, the anti-methanogenic lovastatin analog or derivative may be a compound of the following Formula:

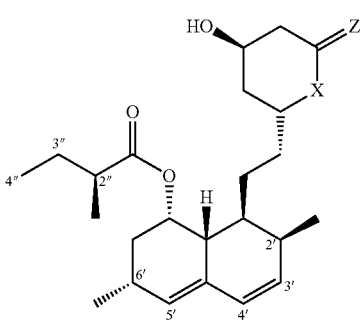

XXXVI wherein X is selected from O, N, and S, and Z is selected from substituted or unsubstituted $C_{1-6}$ alkyl, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ alkyl, substituted or unsubstituted $C_{1-10}$ aminoalkyl, substituted or unsubstituted $C_{5-10}$ aryl, substituted or unsubstituted saturated or unsaturated 3-11 member heteroaryl or heteroaryl alkyl containing 1, 2, 3, or 4 heteroatoms selected independently from N, O, S, or $S(O)_2$ or $R_2$ and $R_3$ may be combined with the nitrogen to which they are attached to form a 3, 4, 5, 6, or 7 membered heterocyclein which one or more of the carbons may be substituted with a heteroatom selected from O, N, or S and in which any of the hydrogens of the heterocycle may be substituted with $C_{1-6}$ alkyl, F, Cl, Br, I, cyano, $C_{1-6}$ alkoxy, or $C_{6-10}$ aryloxy, or a stereoisomer thereof, tautomer thereof, solvate thereof, or a pharmaceutically acceptable salt thereof.

Except where specifically defined to the contrary, the terms "alkyl", "alkenyl", "acyl" "aryloxy" and "alkoxy" include both the straight chain and branched-chain species of the term.

Modified Release Profile

In one aspect, the present invention provides modified release formulations comprising at least one anti-methanogenic lovastatin analog or derivative, wherein the formulation releases at least about 60% of the anti-methanogenic lovastatin analog or derivative after the stomach and into one or more regions of the intestinal tract.

In various embodiments, the anti-methanogenic lovastatin analog or derivative can inhibit the production of methane, inhibit methanogenesis, or inhibit the growth and/or proliferation of methanogens. In some aspects, the anti-methanogenic lovastatin analog or derivative is in a hydroxyacid form which typically is, without wishing to be bound by theory, an effective inhibitor of HMG-CoA reductase, or in a lactone form which typically is, without wishing to be bound by theory, an ineffective HMG-CoA inhibitor.

In one aspect, the present invention provides modified release formulations comprising at least one anti-methanogenic lovastatin analog or derivative, wherein the formulation releases at least 60% of the anti-methanogenic lovastatin analog or derivative after the stomach into one or more regions of the intestinal tract.

In various embodiments, the anti-methanogenic lovastatin analog or derivative is in the lactone form, including substantially in the lactone form, at the site of delivery by the present formulations. For example, in some embodiments, the amount of GI tract-delivered anti-methanogenic lovastatin analog or derivative which is in the lactone form is more than about 95%, or more than about 90%, or more than about 85%, or more than about 80%, or more than about 75%, or more than about 70%, or more than about 65%, or more than about 60%, or more than about 55%, or more than about 50%, or more than about 25%.

In various embodiments, the modified-release formulations of the present invention are designed for immediate release (e.g. upon ingestion). In various embodiments, the modified-release formulations may have sustained-release profiles, i.e. slow release of the active ingredient(s) in the body (e.g., GI tract) over an extended period of time. In various embodiments, the modified-release formulations may have a delayed-release profile, i.e. not immediately release the active ingredient(s) upon ingestion; rather, postponement of the release of the active ingredient(s) until the composition is lower in the gastrointestinal tract; for example, for release in the small intestine (e.g., one or more of duodenum, jejunum, ileum) or the large intestine (e.g., one or more of cecum, ascending, transverse, descending or sigmoid portions of the colon, and rectum). For example, a composition can be enteric coated to delay release of the active ingredient(s) until it reaches the small intestine or large intestine. In some embodiments, there is not a substantial amount of the active ingredient(s) of the present formulations in the stool.

In various embodiments, the modified-release formulation of the present invention releases (optionally as a first release) at least 60% of the anti-methanogenic lovastatin analog or derivative after the stomach into one or more regions of the intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the anti-methanogenic lovastatin analog or derivative in the intestine.

In various embodiments, the modified-release formulation releases (optionally as a first release) the anti-methanogenic lovastatin analog or derivative in the small intestine. In various embodiments, the modified-release formulation of the present invention releases at least 60% of the anti-methanogenic lovastatin analog or derivative in the small intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the anti-methanogenic lovastatin analog or derivative in the small intestine.

In one embodiment, the formulation releases (optionally as a first release) the anti-methanogenic lovastatin analog or derivative in the duodenum. In various embodiments, the modified-release formulation of the present invention releases at least 60% of the anti-methanogenic lovastatin analog or derivative in the duodenum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the anti-methanogenic lovastatin analog or derivative in the duodenum.

In another embodiment, the formulation releases (optionally as a first release) the anti-methanogenic lovastatin analog or derivative in the jejunum. In various embodiments, the modified-release formulation of the present invention releases at least 60% of the anti-methanogenic lovastatin analog or derivative in the jejunum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the anti-methanogenic lovastatin analog or derivative in the jejunum.

In a further embodiment, the formulation releases (optionally as a first release) the anti-methanogenic lovastatin analog or derivative in the ileum and/or the ileocecal junction. In various embodiments, the modified-release formulation of the present invention releases at least 60% of the anti-methanogenic lovastatin analog or derivative in the ileum and/or the ileocecal junction. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the anti-methanogenic lovastatin analog or derivative in the ileum and/or the ileocecal junction.

In other embodiments, the modified-release formulation releases (optionally as a first release) the anti-methanogenic lovastatin analog or derivative in the large intestine. In various embodiments, the modified-release formulation of the present invention releases at least 60% of the anti-methanogenic lovastatin analog or derivative in the large intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the anti-methanogenic lovastatin analog or derivative in the large intestine.

In an embodiment, the modified-release formulation releases (optionally as a first release) the anti-methanogenic lovastatin analog or derivative in the cecum. In various embodiments, the modified-release formulation of the present invention releases at least 60% of the anti-methanogenic lovastatin analog or derivative in the cecum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the anti-methanogenic lovastatin analog or derivative n in the cecum.

In another embodiment, the modified-release formulation releases (optionally as a first release) the anti-methanogenic lovastatin analog or derivative in the ascending colon. In various embodiments, the modified-release formulation of the present invention releases at least 60% of the anti-methanogenic lovastatin analog or derivative in the ascending colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the anti-methanogenic lovastatin analog or derivative in the ascending colon.

In yet another embodiment, the anti-methanogenic lovastatin analog or derivative is released (optionally as a first release) in the transverse colon. In various embodiments, the modified-release formulation of the present invention releases at least 60% of the anti-methanogenic lovastatin analog or derivative in the transverse colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the anti-methanogenic lovastatin analog or derivative in the transverse colon.

In a further embodiment, the anti-methanogenic lovastatin analog or derivative is released (optionally as a first release) in the descending colon. In various embodiments, the modified-release formulation of the present invention releases at least 60% of the anti-methanogenic lovastatin analog or derivative in the descending colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the anti-methanogenic lovastatin analog or derivative in the descending colon.

In another embodiment, the anti-methanogenic lovastatin analog or derivative is released (optionally as a first release) in the sigmoid colon. In various embodiments, the modified-release formulation of the present invention releases at least 60% of the anti-methanogenic lovastatin analog or derivative in the sigmoid colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the anti-methanogenic lovastatin analog or derivative in the sigmoid colon.

In certain embodiments, the modified-release formulation does not substantially release the anti-methanogenic lovastatin analog or derivative in the stomach.

In certain embodiments, the modified-release formulation releases the anti-methanogenic lovastatin analog or derivative at a specific pH. For example, in some embodiments, the modified-release formulation is substantially stable in an acidic environment and substantially unstable (e.g., dissolves rapidly or is physically unstable) in a near neutral to alkaline environment. In some embodiments, stability is indicative of not substantially releasing while instability is indicative of substantially releasing. For example, in some embodiments, the modified-release formulation is substantially stable at a pH of about 7.0 or less, or about 6.5 or less, or about 6.0 or less, or about 5.5 or less, or about 5.0 or less, or about 4.5 or less, or about 4.0 or less, or about 3.5 or less, or about 3.0 or less, or about 2.5 or less, or about 2.0 or less, or about 1.5 or less, or about 1.0 or less. In some embodiments, the present formulations are stable in lower pH areas and therefore do not substantially release in, for example, the stomach. In some embodiments, modified-release formulation is substantially stable at a pH of about 1 to about 4 or lower and substantially unstable at pH values that are greater. In these embodiments, the modified-release formulation is not substantially released in the stomach. In these embodiments, the modified-release formulation is substantially released in the small intestine (e.g. one or more of the duodenum, jejunum, and ileum) and/or large intestine (e.g. one or more of the cecum, ascending colon, transverse colon, descending colon, and sigmoid colon). In some embodiments, modified-release formulation is substantially stable at a pH of about 4 to about 5 or lower and consequentially is substantially unstable at pH values that are greater and therefore is not substantially released in the stomach and/or small intestine (e.g. one or more of the duodenum, jejunum, and ileum). In these embodiments, the modified-release formulation is substantially released in the large intestine (e.g. one or more of the cecum, ascending colon, transverse colon, descending colon, and sigmoid colon). In various embodiments, the pH values recited herein may be adjusted as known in the art to account for the state of the subject, e.g. whether in a fasting or postprandial state.

In some embodiments, the modified-release formulation is substantially stable in gastric fluid and substantially unstable in intestinal fluid and, accordingly, is substantially released in the small intestine (e.g. one or more of the duodenum, jejunum, and ileum) and/or large intestine (e.g. one or more of the cecum, ascending colon, transverse colon, descending colon, and sigmoid colon).

In some embodiments, the modified-release formulation is stable in gastric fluid or stable in acidic environments. These modified-release formulations release about 30% or less by weight of the anti-methanogenic lovastatin analog or derivative and/or additional therapeutic agent in the modified-release formulation in gastric fluid with a pH of about 4 to about 5 or less, or simulated gastric fluid with a pH of about 4 to about 5 or less, in about 15, or about 30, or about 45, or about 60, or about 90 minutes. Modified-release formulations of the of the invention may release from about 0% to about 30%, from about 0% to about 25%, from about 0% to about 20%, from about 0% to about 15%, from about 0% to about 10%, about 5% to about 30%, from about 5% to about 25%, from about 5% to about 20%, from about 5% to about 15%, from about 5% to about 10% by weight of the anti-methanogenic lovastatin analog or derivative and/or additional therapeutic agent in the modified-release formulation in gastric fluid with a pH of 4-5, or less or simulated gastric fluid with a pH of 4-5 or less, in about 15, or about 30, or about 45, or about 60, or about 90 minutes. Modified-release formulations of the invention may release about 1%, about 2%, about 3%, about 4%, about 5%, about 6%, about 7%, about 8%, about 9%, or about 10% by weight of the total anti-methanogenic lovastatin analog or derivative and/or additional therapeutic agent in the modified-release formulation in gastric fluid with a pH of 5 or less, or simulated gastric fluid with a pH of 5 or less, in about 15, or about 30, or about 45, or about 60, or about 90 minutes.

In some embodiments, the modified-release formulation is unstable in intestinal fluid. These modified-release formulations release about 70% or more by weight of the anti-methanogenic lovastatin analog or derivative and/or additional therapeutic agent in the modified-release formulation in intestinal fluid or simulated intestinal fluid in about 15, or about 30, or about 45, or about 60, or about 90 minutes. In some embodiments, the modified-release formulation is unstable in near neutral to alkaline environments. These modified-release formulations release about 70% or more by weight of the anti-methanogenic lovastatin analog or derivative and/or additional therapeutic agent in the modified-release formulation in intestinal fluid with a pH of about 4-5 or greater, or simulated intestinal fluid with a pH of about 4-5 or greater, in about 15, or about 30, or about 45, or about 60, or about 90 minutes. A modified-release formulation that is unstable in near neutral or alkaline environments may release 70% or more by weight of anti-methanogenic lovastatin analog or derivative and/or additional therapeutic agent in the modified-release formulation in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

In one embodiment, the modified-release formulation may remain essentially intact, or may be essentially insoluble, in gastric fluid. The stability of the delayed-release coating can be pH dependent. Delayed-release coatings that are pH dependent will be substantially stable in acidic environments (pH of about 5 or less), and substantially unstable in near neutral to alkaline environments (pH greater than about 5). For example, the delayed-release coating may essentially disintegrate or dissolve in near neutral to alkaline environments such as are found in the small intestine (e.g. one or more of the duodenum, jejunum, and ileum) and/or large intestine (e.g. one or more of the cecum, ascending colon, transverse colon, descending colon, and sigmoid colon).

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

Alternatively, the stability of the modified-release formulation can be enzyme-dependent. Delayed-release coatings that are enzyme dependent will be substantially stable in fluid that does not contain a particular enzyme and substantially unstable in fluid containing the enzyme. The delayed-release coating will essentially disintegrate or dissolve in fluid containing the appropriate enzyme. Enzyme-dependent control can be brought about, for example, by using materials which release the active ingredient only on exposure to enzymes in the intestine, such as galactomannans. Also, the stability of the modified-release formulation can be dependent on enzyme stability in the presence of a microbial enzyme present in the gut flora.

In some embodiments, a dual pulse formulation is provided. In various embodiments, the present invention provides for modified-release formulations that release multiple doses of the anti-methanogenic lovastatin analog or derivative, at different locations along the intestines, at different times, and/or at different pH. In an illustrative embodiment, the modified-release formulation comprises a first dose of the anti-methanogenic lovastatin analog or derivative and a second dose of the anti-methanogenic lovastatin analog or derivative, wherein the first dose and the second dose are released at different locations along the intestines, at different times, and/or at different pH. For example, the first dose is released at the duodenum, and the second dose is released at the ileum. In another example, the first dose is released at the jejunum, and the second dose is released at the ileum. In other embodiments, the first dose is released at a location along the small intestine (e.g., the duodenum), while the second dose is released along the large intestine (e.g., the ascending colon). In various embodiments, the modified-release formulation may release at least one dose, at least two doses, at least three doses, at least four doses, at least five doses, at least six doses, at least seven doses, or at least eight doses of the anti-methanogenic lovastatin analog or derivative at different locations along the intestines, at different times, and/or at different pH. Each individual dose may comprise the same lovastatin analog or derivative or may comprise different lovastatin analog or derivative.

In some embodiments, the dual pulse formulation is an enteric-coated capsule comprising beads that comprise an anti-methanogenic lovastatin analog or derivative and optionally an additional therapeutic agent. In some embodiments, the enteric-coated capsule dissolves in a first area of GI tract to release the beads and/or a first population of beads releases in a second area of the GI tract (and that is not the same as the first area of the GI tract) and a second population of beads releases in a third area of the GI tract (and that is not the same as the first or second areas of the GI tract). In some embodiments, the dose/release ratio (e.g. how much agent is released in various locations) can be tuned as needed. In some embodiments, the enteric-coated capsule dissolves in the duodenum to release the beads and/or a first population of beads releases in the duodenum and/or a second population of beads releases in the ileocecal junction (see, e.g. FIGS. 1-4).

Modified Release Formulation and Dosage Forms

The modified-release formulation of the present invention may further comprise a pharmaceutically acceptable carrier or excipient. As one skilled in the art will recognize, the formulations can be in any suitable form appropriate for the desired use and route of administration. Examples of suitable dosage forms include, for example, oral and parenteral dosage forms.

Suitable dosage forms for oral use include, for example, solid dosage forms such as tablets, dispersible powders, granules, and capsules. In one embodiment, the modified-release formulation is in the form of a tablet. In another embodiment, the modified-release formulation is in the form of a capsule. In yet another embodiment, the modified-release formulation is in the form of a soft-gel capsule. In a further embodiment, the modified-release formulation is in the form of a gelatin capsule.

In such dosage forms, the active compound is mixed with at least one inert, pharmaceutically acceptable excipient or carrier such as sodium citrate, dicalcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinylpyrrolidone, sucrose, acacia, polyvinyl alcohol, polyvinylpyrrolidone, methylcellulose, hydroxypropyl cellulose, and hydroxymethyl cellulose etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium compounds, etc., g) wetting agents such as, for example, cetyl alcohol and glycerol monostearate, etc., h) absorbents such as kaolin and bentonite clay, etc., and i) lubricants such as talc, calcium stearate, magnesium stearate, solid polyethylene glycols, sodium lauryl sulfate, glyceryl behenate, etc., and mixtures of such excipients. One of skill in the art will recognize that particular excipients may have two or more functions in the oral dosage form. In the case of an oral dosage form, for example, a capsule or a tablet, the dosage form may also comprise buffering agents.

The modified release formulation can additionally include a surface active agent. Surface active agents suitable for use in the present invention include, but are not limited to, any pharmaceutically acceptable, non-toxic surfactant. Classes of surfactants suitable for use in the compositions of the invention include, but are not limited to polyethoxylated fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-olyoxypropylene block copolymers, sorbitan fatty acid esters, lower alcohol fatty acid esters, ionic surfactants, and mixtures thereof. In some embodiments, compositions of the invention may comprise one or more surfactants including, but not limited to, sodium lauryl sulfate, polysorbate 20, polysorbate 40, polysorbate 60, polysorbate 80, and triethyl citrate.

The modified-release formulation can also contain pharmaceutically acceptable plasticizers to obtain the desired mechanical properties such as flexibility and hardness. Such plasticizers include, but are not limited to, triacetin, citric acid esters, phthalic acid esters, dibutyl sebacate, cetyl alcohol, polyethylene glycols, polysorbates or other plasticizers.

The modified-release formulation can also include one or more application solvents. Some of the more common solvents that can be used to apply, for example, a delayed-release coating composition include isopropyl alcohol, acetone, methylene chloride and the like.

The modified-release formulation can also include one or more alkaline materials. Alkaline material suitable for use in compositions of the invention include, but are not limited to, sodium, potassium, calcium, magnesium and aluminum salts of acids such as phosphoric acid, carbonic acid, citric acid and other aluminum/magnesium compounds. In addition the alkaline material may be selected from antacid materials such as aluminum hydroxides, calcium hydroxides, magnesium hydroxides and magnesium oxide.

The solid oral dosage forms can be prepared by any conventional method known in the art, for example granulation (e.g., wet or dry granulation) of the active compound (e.g., statins) with one or more suitable excipients. Alternatively, the active compound can be layered onto an inert core (e.g., a nonpareil/sugar sphere or silica sphere) using conventional methods such as fluidized bed or pan coating, or extruded and spheronized using methods known in the art, into active compound-containing beads. Such beads can then be incorporated into tablets or capsules using conventional methods.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, etc., and mixtures thereof.

Besides inert diluents, the oral compositions can also include adjuvants such as sweetening, flavoring, and perfuming agents.

Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

The formulations comprising the therapeutic agents of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In various embodiments, the modified-release formulation of the present invention may utilize one or more modified-release coatings such as delayed-release coatings to provide for effective, delayed yet substantial delivery of the anti-methanogenic lovastatin analog or derivative to the GI tract together with, optionally, other therapeutic agents.

In one embodiment, the delayed-release coating includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT®-type polymer (poly (methacrylic acid, methylmethacrylate), hydroxypropyl methylcellulose acetate succinate, cellulose acetate trimellitate, shellac or other suitable enteric coating polymers. The EUDRAGIT®-type polymer include, for example, EUDRAGIT® FS 30D, L 30 D-55, L 100-55, L 100, L 12,5, L 12.5 P, RL 30 D, RL PO, RL 100, RL 12,5, RS 30 D, RS PO, RS 100, RS 12,5, NE 30 D, NE 40 D, NM 30 D, S 100, S 12,5, and S 12.5 P. In some embodiments, one or more of EUDRAGIT® FS 30D, L 30 D-55, L 100-55, L 100, L 12,5, L 12.5 P RL 30 D, RL PO, RL 100, RL 12,5, RS 30 D, RS PO, RS 100, RS 12,5, NE 30 D, NE 40 D, NM 30 D, S 100, S 12.5 and S 12.5 P is used. The enteric agent may be a combination of the foregoing solutions or dispersions.

In another embodiment, the delayed-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e, a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS®, EUDRAGIT RL®, and EUDRAGIT NE® Insoluble polymers useful in the present invention include polyvinyl esters, polyvinyl acetals, polyacrylic acid esters, butadiene styrene copolymers, and the like. In one embodiment, colonic delivery is achieved by use of a slowly-eroding wax plug (e.g., various PEGS, including for example, PEG6000).

In a further embodiment, the delayed-release coating may be degraded by a microbial enzyme present in the gut flora. In one embodiment, the delayed-release coating may be degraded by a bacteria present in the small intestine. In another embodiment, the delayed-release coating may be degraded by a bacteria present in the large intestine.

The present invention provides for modified-release formulations that release multiple doses of the anti-methanogenic lovastatin analog or derivative along the gastrointestinal tract. The overall release profile of such a formulation may be adjusted by utilizing, for example, multiple particle types or multiple layers. In one embodiment, the first dose of the anti-methanogenic lovastatin analog or derivative may be formulated for release in, for example, the duodenum, whereas the second dose is formulated for delayed release in, for example, the ileum. In another embodiment, the first dose of the anti-methanogenic lovastatin analog or derivative may be formulated for release in, for example, the small intestines, whereas the second dose is formulated for delayed release in, for example, the large intestines. Alternatively, multiple doses are released at different locations alone the intestine.

In one embodiment, one or more doses of the anti-methanogenic lovastatin analog or derivative may be encapsulated in a core particle, for example, in the form of a microbead. For example, the first dose of the anti-methanogenic lovastatin analog or derivative may be encapsulated in a core particle coated with a modified-release coating designed for release at a first location along the intestinal tract, and the second dose of the anti-methanogenic lovastatin analog or derivative may be encapsulated in a core particle coated with a modified-release coating designed for release at a second location along the intestinal tract. The formulation may comprise a plurality of such modified-release particles. For example, the formulation is in the form of capsules comprising multiple microbeads. In such an embodiment, a combination of microbeads may be utilized in which each microbead is designed to release at a specific time point or location. In an alternative embodiment, the formulation is formulated as a capsule within a capsule, with each capsule having different time- or pH-dependent release properties.

In another embodiment, one or more doses of the anti-methanogenic lovastatin analog or derivative may be encapsulated in a layer. For example, the first dose of the anti-methanogenic lovastatin analog or derivative may be encapsulated in a layer coated with a modified-release coating designed for release at a first location along the intestinal tract, and the second dose of the anti-methanogenic lovastatin analog or derivative may be encapsulated in a layer coated with a modified-release coating designed for release at a second location along the intestinal tract. The formulation may comprise a plurality of such modified-release layers. For example, the formulation is in the form of multi-layered tablet or a multi-layered capsule. Each layer may have different time- or pH-dependent release properties.

In the above embodiments, the coated particles or layers with the delayed-release coating may be further covered with an overcoat layer. The overcoat layer can be applied as described for the other coating compositions. The overcoat materials are pharmaceutically acceptable compounds such as sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. The overcoat materials can prevent potential agglomeration of particles coated with the delayed-release coating, protect the delayed-release coating from cracking during the compaction process or enhance the tableting process.

Furthermore, in various embodiments, the agents described herein may be in the form of a pharmaceutically acceptable salt, namely those salts which are suitable for use in contact with the tissues of humans and other animals without undue toxicity, irritation, allergic response and the like, and are commensurate with a reasonable benefit/risk ratio. Pharmaceutically acceptable salts are well known in the art. The salts can be prepared in situ during the final isolation and purification of the therapeutic agents, or separately by reacting the free base function with a suitable acid or a free acid functionality with an appropriate alkaline moiety. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methyl amine, dimethylamine, trimethylamine, triethylamine, ethylamine, and the like.

In various embodiments, the formulation comprises at least one microbead or mini-tablet. In some embodiments, each microbead or mini-tablet comprises about 5-20% by weight the lovastatin analog or derivative (including without limitation lovastatin diol lactone). For example, the lovastatin analog or derivative (including without limitation lovastatin diol lactone) may be present at about 5%, about 6%, about 7%, about 8%, about 9%, about 10%, about 11%, about 12%, about 13%, about 14%, about 15%, about 16%, about 17%, about 18%, about 19%, or about 20% by weight. In some embodiments, each microbead or mini-tablet may further comprise about 50-70% by weight tablet diluent (e.g., about 50%, about 51%, about 52%, about 53%, about 54%, about 55%, about 56%, about 57%, about 58%, about 59%, about 60%, about 61%, about 62%, about 63%, about 64%, or about 65%, or about 66%, about 67%, or about 68%, or about 69%, or about 70%). In some embodiments, each microbead or mini-tablet may further comprise about 1-10% by weight tablet binder (e.g., about 1%, about 2%, about 3%, about 4%, about 5%, about 6%, about 7%, about 8%, about 9%, or about 10%). In some embodiments, each microbead or mini-tablet may further comprise about 0.1-3.0% by weight viscosity and dispersion agent (e.g., about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0%). In some embodiments, each microbead or mini-tablet may further comprise about 0.1-3.0% by weight lubricant, for example, to facilitate tableting (e.g., about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0%). In some embodiments, each microbead or mini-tablet may further comprise about 1-10% by weight tablet disintegrant (e.g., about 1%, about 2%, about 3%, about 4%, about 5%, about 6%, about 7%, about 8%, about 9%, or about 10%). In some embodiments, each microbead or mini-tablet may further comprise about 10-20% by weight an enteric polymer that dissolves at a pH of either about 5.5 or about 7.0 (e.g., about 10%, about 11%, about 12%, about 13%, about 14%, about 15%, about 16%, about 17%, about 18%, about 19%, or about 20%).

In various embodiments, the formulation comprises one or more of, or two or more of, or three or more of, or four or more of, or five or more of, or all of an lovastatin analog or derivative (including without limitation lovastatin diol lactone), the lovastatin analog or derivative (including without limitation lovastatin diol lactone) optionally being in two doses; microcrystalline cellulose (e.g. Avicel PH102); copovidone (e.g. Kollidon VA64 Fine); silicon dioxide (e.g. Aerosil 200); magnesium stearate; crospovidone (e.g. Kollidon CL or Kollidon CL-F); where the first dose of at least one lovastatin analog or derivative (including without limitation lovastatin diol lactone) is encapsulated by an enteric polymer that dissolves at a pH of about 5.5 (e.g. EUDRAGIT L 30 D-55+PlasACRYL HTP20); and the second dose of at least one lovastatin analog or derivative (including without limitation lovastatin diol lactone) is encapsulated by an enteric polymer that dissolves a at pH of about 7.0 (e.g. EUDRAGIT FS 30 D+PlasACRYL T20 and/or EUDRAGIT® S 100).

In various embodiments, the formulation comprises at least one microbead or mini-tablet. Each microbead or mini-tablet comprises about 5-20% by weight of the lovastatin analog or derivative (including without limitation lovastatin did lactone). For example, the lovastatin analog or derivative (including without limitation lovastatin did lactone) may be present at about 5%, about 6%, about 7%, about 8%, about 9%, about 10%, about 11%, about 12%, about 13%, about 14%, about 15%, about 16%, about 17%, about 18%, about 19%, or about 20% by weight. In some embodiments, each microbead or mini-tablet may further comprise about 50-70% by weight microcrystalline cellulose (e.g. Avicel PH102). For example, the microcrystalline cellulose may be present at about 50%, about 51%, about 52%, about 53%, about 54%, about 55%, about 56%, about 57%, about 58%, about 59%, about 60%, about 61%, about 62%, about 63%, about 64%, or about 65%, or about 66%, about 67%, or about 68%, or about 69%, or about 70% by weight. In some embodiments, each microbead or mini-tablet may further comprise about 1-10% by weight copovidone (e.g. Kollidon VA64 Fine). For example, the copovidone may be present at about 1%, about 2%, about 3%, about 4%, about 5%, about 6%, about 7%, about 8%, about 9%, or about 10% by weight. In some embodiments, each microbead or mini-tablet may further comprise about 0.1-3.0% by weight silicon dioxide (e.g. Aerosil 200). For example, the silicon dioxide may be present at about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0% by weight. In some embodiments, each microbead or mini-tablet may further comprise about 0.1-3.0% by weight magnesium stearate (for example, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0%). In some embodiments, each microbead or mini-tablet may further comprise about 1-10% by weight crospovidone (e.g. Kollidon CL or Kollidon CL-F). For example, the crospovidone may be present at about 1%, about 2%, about 3%, about 4%, about 5%, about 6%, about 7%, about 8%, about 9%, or about 10% by weight. In some embodiments, each microbead or mini-tablet may further comprise about 10-20% by weight an enteric polymer that dissolves at a pH of about 5.5 (e.g. EUDRAGIT L 30 D-55+PlasACRYL HTP20) or about 7.0 (e.g. EUDRAGIT FS 30 D+PlasACRYL T20 and/or EUDRAGIT® S 100). For example, the enteric polymer may be about 10%, about 11%, about 12%, about 13%, about 14%, about 15%, about 16%, about 17%, about 18%, about 19%, or about 20% by weight.

In some embodiments, the formulation comprises at least one microbead or mini-tablet with each microbead or mini-tablet comprising about 12% by weight the lovastatin analog or derivative (including without limitation lovastatin diol lactone); about 60% by weight microcrystalline cellulose (e.g. Avicel PH102); about 6% by weight copovidone (e.g. Kollidon VA64 Fine); about 2% by weight silicon dioxide (e.g. Aerosil 200); about 1% by weight magnesium stearate; about 5% by weight crospovidone (e.g. Kollidon CL or Kollidon CL-F); and about 15% by weight an enteric polymer that dissolves at a pH of about 5.5 (e.g. EUDRAGIT L 30 D-55+PlasACRYL HTP20) or about 7.0 (e.g. EUDRAGIT FS 30 D+PlasACRYL T20 and/or EUDRAGIT® S 100).

In some embodiments, the formulation comprises at least one microbead or mini-tablet with each microbead or mini-tablet comprising about 12.2% by weight lovastatin diol lactone; about 60.9% by weight microcrystalline cellulose (Avicel PH102); about 6.1% by weight copovidone (Kollidon VA64 Fine); about 1.7% by weight silicon dioxide (Aerosil 200); about 0.9% by weight magnesium stearate; about 5.2% by weight crospovidone (Kollidon CL-F); and either about 13.0% by weight of EUDRAGIT L 30 D-55+PlasACRYL HTP20 coating (which dissolves at a pH of about 5.5) or 13% by weight of EUDRAGIT FS 30 D+PlasACRYL T20 coating (which dissolves at a pH of about 7.0).

In various embodiments, the present formulation comprise a mini-tablet enteric coating thickness, e.g. EUDRAGIT, e.g. EUDRAGIT L 30 D-55 or EUDRAGIT FS 30 D, of greater than about 10%, about 13%, about 15%, or about 17%, or about 20%, or about 25%.

In various embodiments, the formulation of the present invention may comprise at least one mini-tablet that releases at a first pH (e.g. pH of about 5.5) and at least one mini-tablet that releases at a second pH (e.g., pH of about 7.0) at a ratio of 1:2. In such embodiments, the formulation may comprise about 5-20% by weight the lovastatin analog or derivative (including without limitation lovastatin diol lactone). For example, the lovastatin analog or derivative (including without limitation lovastatin diol lactone) may be present at about 5%, about 6%, about 7%, about 8%, about 9%, about 10%, about 11%, about 12%, about 13%, about 14%, about 15%, about 16%, about 17%, about 18%, about 19%, or about 20% by weight of the entire formulation. In some embodiments, the formulation may further comprise about 30-60% by weight tablet diluent (e.g., about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%). In some embodiments, the formulation may further comprise about 1-10% by weight tablet binder (e.g., about 1%, about 2%, about 3%, about 4%, about 5%, about 6%, about 7%, about 8%, about 9%, or about 10%). In some embodiments, the formulation may further comprise about 0.1-3.0% by weight viscosity and dispersion agent (e.g., about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0%). In some embodiments, the formulation may further comprise about 0.1-3.0% by weight lubricant, for example, to facilitate tableting (e.g., about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0%). In some embodiments, the formulation may further comprise about 1-10% by weight tablet disintegrant (e.g., about 1%, about 2%, about 3%, about 4%, about 5%, about 6%, about 7%, about 8%, about 9%, or about 10%). In some embodiments, the formulation may further comprise about 0.5-10% by weight an enteric polymer that dissolves at a pH of about 5.5 (e.g. EUDRAGIT L 30 D-55+PlasACRYL HTP20). For example, the enteric polymer that dissolves at a pH of about 5.5 may be present in the formulation at about 0.5%, about 0.6%, about 0.7%, about 0.8%, about 0.9%, about 1%, about 2%, about 3%, about 4%, about 5%, about 6%, about 7%, about 8%, about 9%, or about 10% by weight. In some embodiments, the formulation may further comprise about 1-15% by weight an enteric polymer that dissolves at a pH of about 7.0. (e.g. EUDRAGIT FS 30 D+PlasACRYL T20 and/or EUDRAGIT® S 100). For example, the enteric polymer that dissolves at a pH of about 7.0 may be present in the formulation at about 1%, about 2%, about 3%, about 4%, about 5%, about 6%, about 7%, about 8%, about 9%, about 10%, about 11%, about 12%, about 13%, about 14%, or about 15% by weight. In such embodiments, the lovastatin analog or derivative (including without limitation lovastatin diol lactone) may be released in two doses. The first dose of lovastatin analog or derivative (including without limitation lovastatin diol lactone) is encapsulated by the enteric polymer that dissolves at a pH of about 5.5; and the second dose of lovastatin analog or derivative (including without limitation lovastatin diol lactone) is encapsulated by the enteric polymer that dissolves a at pH of about 7.0.

For example, the formulation may comprise at least one mini-tablet that releases at a first pH (e.g. pH of about 5.5) and at least one mini-tablet that releases at a second pH (e.g., pH of about 7.0) at a ratio of 1:2. The formulation may comprise about 9% by weight the lovastatin analog or derivative (including without limitation lovastatin diol lactone); about 42% by weight microcrystalline cellulose (e.g. Avicel PH 102); about 4% by weight copovidone (e.g. Kollidon VA64 Fine); about 1% by weight silicon dioxide (e.g. Aerosil 200); about 0.5% by weight magnesium stearate; about 4% by weight crospovidone (e.g. Kollidon CL or Kollidon CL-F); about 3% by weight an enteric polymer that dissolves at a pH of about 5.5 (e.g. EUDRAGIT L 30 D-55+PlasACRYL HTP20); and about 6% by weight an enteric polymer that dissolves at a pH of about 7.0 (e.g. EUDRAGIT FS 30 D+PlasACRYL T20 and/or EUDRAGIT® S 100).

In another example, the formulation may comprise at least one mini-tablet that releases at a first pH (e.g. pH of about 5.5) and at least one mini-tablet that releases at a second pH (e.g., pH of about 7.0) at a ratio of 1:2. The formulation may comprise about 8.5% by weight the lovastatin analog or derivative (including without limitation lovastatin diol lactone); about 42.4% by weight microcrystalline cellulose (e.g. Avicel PH102); about 4.2% by weight copovidone (e.g. Kollidon VA64 Fine); about 1.2% by weight silicon dioxide (e.g. Aerosil 200); about 0.6% by weight magnesium stearate; about 3.6% by weight crospovidone (e.g. Kollidon CL or Kollidon CL-F); about 3% by weight an enteric polymer that dissolves at a pH of about 5.5 (e.g. EUDRAGIT L 30 D-55+PlasACRYL HTP20); and about 6.1% by weight an enteric polymer that dissolves at a pH of about 7.0 (e.g. EUDRAGIT FS 30 D+PlasACRYL T20 and/or EUDRAGIT® S 100).

In another embodiment, the formulation of the present invention may at least one mini-tablet that releases at a first pH (e.g. pH of about 5.5) and at least one mini-tablet that releases at a second pH (e.g., pH of about 7.0) at a ratio of 1:5. In such embodiments, the formulation may comprise about 5-20% by weight the lovastatin analog or derivative (including without limitation lovastatin diol lactone). For example, the lovastatin analog or derivative (including without limitation lovastatin diol lactone) may be present at about 5%, about 6%, about 7%, about 8%, about 9%, about 10%, about 11%, about 12%, about 13%, about 14%, about 15%, about 16%, about 17%, about 18%, about 19%, or about 20% by weight of the entire formulation. In some embodiments, the formulation may further comprise about 30-60% by weight tablet diluent (e.g., about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%). In some embodiments, the formulation may further comprise about 1-10% by weight tablet binder (e.g., about 1%, about 2%, about 3%, about 4%, about 5%, about 6%, about 7%, about 8%, about 9%, or about 10%). In some embodiments, the formulation may further comprise about 0.1-3.0% by weight viscosity and dispersion agent (e.g., about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0%). In some embodiments, the formulation may further comprise about 0.1-3.0% by weight lubricant, for example, to facilitate tableting (e.g., about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0%). In some embodiments, the formulation may further comprise about 1-10% by weight tablet disintegrant (e.g., about 1%, about 2%, about 3%, about 4%, about 5%, about 6%, about 7%, about 8%, about 9%, or about 10%). In some embodiments, the formulation may further comprise about 0.5-10% by weight an enteric polymer that dissolves at a pH of about 5.5 (e.g. EUDRAGIT L 30 D-55+PlasACRYL HTP20. For example, the enteric polymer that dissolves at a pH of about 5.5 may be present in the formulation at about 0.5%, about 0.6%, about 0.7%, about 0.8%, about 0.9%, about 1%, about 2%, about 3%, about 4%, about 5%, about 6%, about 7%, about 8%, about 9%, or about 10% by weight. In some embodiments, the formulation may further comprise about 1-15% by weight an enteric polymer that dissolves at a pH of about 7.0 (e.g. EUDRAGIT FS 30 D+PlasACRYL T20 and/or EUDRAGIT® S 100. For example, the enteric polymer that dissolves at a pH of about 7.0 may be present in the formulation at about 1%, about 2%, about 3%, about 4%, about 5%, about 6%, about 7%, about 8%, about 9%, about 10%, about 11%, about 12%, about 13%, about 14%, or about 15% by weight. In such embodiments, the lovastatin analog or derivative (including without limitation lovastatin diol lactone) may be released in two doses. The first dose of lovastatin analog or derivative (including without limitation lovastatin diol lactone) is encapsulated by the enteric polymer that dissolves at a pH of about 5.5; and the second dose of lovastatin analog or derivative (including without limitation lovastatin diol lactone) is encapsulated by the enteric polymer that dissolves a at pH of about 7.0.

For example, the formulation may comprise at least one mini-tablet that releases at a first pH (e.g. pH of about 5.5) and at least one mini-tablets that release at a second pH (e.g., pH of about 7.0) at a ratio of 1:5. The formulation may comprise about 10% by weight the lovastatin analog or derivative (including without limitation lovastatin diol lactone); about 50% by weight microcrystalline cellulose (e.g. Avicel PH102); about 5% by weight copovidone (e.g. Kollidon VA64 Fine); about 1% by weight silicon dioxide (e.g. Aerosil 200); about 0.5% by weight magnesium stearate; about 4% by weight crospovidone (e.g. Kollidon CL or Kollidon CL-F); about 2% by weight an enteric polymer that dissolves at a pH of about 5.5 (e.g. EUDRAGIT L 30 D-55+PlasACRYL HTP20); and about 9% by weight an enteric polymer that dissolves at a pH of about 7.0. (e.g. EUDRAGIT FS 30 D+PlasACRYL T20 and/or EUDRAGIT® S 100).

In another example, the formulation may comprise at least one mini-tablet that releases at a first pH (e.g. pH of about 5.5) and at least one mini-tablet that releases at a second pH (e.g., pH of about 7.0) at a ratio of 1:5. The formulation may comprise about 10% by weight the lovastatin analog or derivative (including without limitation lovastatin diol lactone); about 50% by weight microcrystalline cellulose (e.g. Avicel PH102); about 5% by weight copovidone (e.g. Kollidon VA64 Fine); about 1.4% by weight silicon dioxide (e.g. Aerosil 200); about 0.7% by weight magnesium stearate; about 4.3% by weight crospovidone (e.g. Kollidon CL or Kollidon CL-F); about 1.8% by weight an enteric polymer that dissolves at a pH of about 5.5 (e.g. EUDRAGIT L 30 D-55+PlasACRYL HTP20); and about 8.9% by weight an enteric polymer that dissolves at a pH of about 7.0. (e.g. EUDRAGIT FS 30 D+PlasACRYL T20 and/or EUDRAGIT® S 100).

The therapeutic agents or their pharmaceutically acceptable salts which are used in accordance with the present invention may exhibit stereoisomerism by virtue of the presence of one or more asymmetric or chiral centers in the compounds. The present invention contemplates the various stereoisomers and mixtures thereof. Desired enantiomers can be obtained by chiral synthesis from commercially available chiral starting materials by methods well known in the art, or may be obtained from mixtures of the enantiomers by resolution using known techniques.

Solvate as used herein refers to a pharmaceutically acceptable solvate form of a specified therapeutic agent that retains the biological effectiveness of such agent. Examples of solvates include therapeutic agents of the invention in combination with, for example, water, isopropanol, ethanol, methanol, DMSO, ethyl acetate, acetic acid, or ethanolamine.

Prodrug, as used herein refers to a therapeutic agent that is converted under physiological conditions or by solvolysis or metabolically (e.g., in vivo) to a specified agent that is pharmaceutically active.

Active metabolite, as used herein refers to a pharmacologically active product produced through metabolism in the body of a specified therapeutic agent.

Co-crystal as used herein refers to a physical association of two or more molecules which owe their stability through non-covalent interaction. One or more components of this molecular complex provide a stable framework in the crystalline lattice. In certain instances, the guest molecules are incorporated in the crystalline lattice as an hydrates or solvates.

Administration and Dosage

It will be appreciated that the actual dose of the anti-methanogenic lovastatin analog or derivative to be administered according to the present invention will vary according to the particular compound, the particular dosage form, and the mode of administration. Many factors that may modify the action of the anti-methanogenic lovastatin analog or derivative (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

Individual doses of the anti-methanogenic lovastatin analog or derivative can be administered in unit dosage forms (e.g., tablets or capsules) containing, for example, from about 0.01 mg to about 100 mg, from about 0.1 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg active ingredient, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg per unit dosage form, or from about 5 mg to about 80 mg per unit dosage form. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg, inclusive of all values and ranges therebetween.

In one embodiment, the anti-methanogenic lovastatin analog or derivative is administered at an amount of from about 0.01 mg to about 100 mg daily, an amount of from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the anti-methanogenic lovastatin analog or derivative is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg, inclusive of all values and ranges therebetween.

In some embodiments, a suitable dosage of the anti-methanogenic lovastatin analog or derivative is in a range of about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, inclusive of all values and ranges therebetween. In other embodiments, a suitable dosage of the anti-methanogenic lovastatin analog or derivative is in a range of about 0.01 mg/kg to about 10 mg/kg of body weight, in a range of about 0.01 mg/kg to about 9 mg/kg of body weight, in a range of about 0.01 mg/kg to about 8 mg/kg of body weight, in a range of about 0.01 mg/kg to about 7 mg/kg of body weight, in a range of 0.01 mg/kg to about 6 mg/kg of body weight, in a range of about 0.05 mg/kg to about 5 mg/kg of body weight, in a range of about 0.05 mg/kg to about 4 mg/kg of body weight, in a range of about 0.05 mg/kg to about 3 mg/kg of body weight, in a range of about 0.05 mg/kg to about 2 mg/kg of body weight, in a range of about 0.05 mg/kg to about 1.5 mg/kg of body weight, or in a range of about 0.05 mg/kg to about 1 mg/kg of body weight.

In accordance with certain embodiments of the invention, the anti-methanogenic lovastatin analog or derivative may be administered, for example, more than once daily, about once per day, about every other day, about every third day, about once a week, about once every two weeks, about once every month, about once every two months, about once every three months, about once every six months, or about once every year.

In various embodiments, the anti-methanogenic lovastatin analog or derivative may be administered in a patient that is fasting. In various embodiments, the anti-methanogenic lovastatin analog or derivative may be administered in a patient with a meal. In various embodiments, the anti-methanogenic lovastatin analog or derivative may be administered in a patient that is postprandial. In various embodiments, patient is on an elemental diet. A comestible total enteral nutrition (TEN) formulation, which is also called an "elemental diet" are commercially available, for example, VIVONEX T.E.N. (Nestle) and its variants, or the like. A useful total enteral nutrition formulation satisfies all the subject's nutritional requirements, containing free amino acids, carbohydrates, lipids, and all essential vitamins and minerals, but is in a form that is readily absorbable in the upper gastrointestinal tract, thus depriving or "starving" the methanogen syntrophic microorganism of nutrients of at least some of the nutrients they use for proliferating. Thus, methanogen syntrophic microorganism growth is inhibited.

Additional Agents and Combination Therapy or Co-Formulation/Patient Selection

Administration of the present formulations may be combined with additional therapeutic agents. Co-administration of the additional therapeutic agent and the present formulations may be simultaneous or sequential. Further the present formulations may comprise an additional therapeutic agent (e.g. via co-formulation).

In some embodiments, the modified-release formulations of the present invention are administered in combination with an additional therapeutic agent. In an embodiment, the additional therapeutic agent and the anti-methanogenic lovastatin analog or derivative are combined into a single modified-release formulation. In some embodiments, the methods of treatment and/or prevention comprise administering the modified-release formulations of the present invention to a subject that is undergoing treatment with an additional therapeutic agent.

In one embodiment, the additional therapeutic agent and the anti-methanogenic lovastatin analog or derivative are administered to a subject simultaneously. The term "simultaneously" as used herein, means that the additional therapeutic agent and the anti-methanogenic lovastatin analog or derivative are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the anti-methanogenic lovastatin analog or derivative can be by simultaneous administration of a single formulation (e.g., a formulation comprising the additional therapeutic agent and the anti-methanogenic lovastatin analog or derivative) or of separate formulations (e.g., a first formulation including the additional therapeutic agent and a second formulation including the anti-methanogenic lovastatin analog or derivative).

Co-administration does not require the additional therapeutic agents to be administered simultaneously, if the timing of their administration is such that the pharmacological activities of the additional therapeutic agent and the anti-methanogenic lovastatin analog or derivative overlap in time, thereby exerting a combined therapeutic effect. For example, the additional therapeutic agent and the anti-methanogenic lovastatin analog or derivative can be administered sequentially. The term "sequentially" as used herein means that the additional therapeutic agent and the anti-methanogenic lovastatin analog or derivative are administered with a time separation of more than about 60 minutes. For example, the time between the sequential administration of the additional therapeutic agent and the anti-methanogenic lovastatin analog or derivative can be more than about 60 minutes, more than about 2 hours, more than about 5 hours, more than about 10 hours, more than about 1 day, more than about 2 days, more than about 3 days, or more than about 1 week apart. The optimal administration times will depend on the rates of metabolism, excretion, and/or the pharmacodynamic activity of the additional therapeutic agent and the anti-methanogenic lovastatin analog or derivative being administered. Either the additional therapeutic agent or the anti-methanogenic lovastatin analog or derivative may be administered first.

Co-administration also does not require the additional therapeutic agents to be administered to the subject by the same route of administration. Rather, each therapeutic agent can be administered by any appropriate route, for example, parenterally or non-parenterally.

The formulations of the present invention may comprise a pharmaceutically acceptable excipient. In some embodiments, the formulation may further include agent which prevents or reduces lactone ring-opening, such as an esterase inhibitor (e.g. grapefruit juice or components naringenin, kaempferol) and/or a paraoxonase inhibitor (e.g. PON1 or PON3 inhibitor). In some embodiments, the esterase inhibitor and/or a paraoxonase inhibitor is one or more of amiodarone, anastrozole, azithromyzcin, cannabinoids, cimetidine, clarithromycin, clotrimazolem, cyclosporine, danazol, delavirdine, dexamethasone, diethyldithiocarbamate, diltiazem, dirithyromycin, disulfiram, entacapone, erythromycin, ethinyl estradiol, fluconazole, fluoxetine, fluvoaxamine, gestodene, grapefruit juice, indinavir, isoniazid, ketoconazole, metronidazole, mibefradil, miconazole, nefazodone, nelfinavir, nevirapine, norfloxacin, norfluoxetine, omeprazole, oxiconazole, paroxetine, propoxyphene, quinidine, quinine, quinupristine and dalfopristin, ranitidine, ritonavir, saquinavir, sertindole, sertraline, troglitazone, troleandomycin, valproic acid and/or a lactam agent selected from oxindole, isatin, δ-valerolactam, ε-caprolactam, 2-hydroxyquinoline, and 3,4-dihydro-2(1H)-quinoline and N-bromo-ε-caprolactam.

In various embodiments, the modified-release formulation of the present invention is administered in combination with an inhibitor of the organic anion transporting polypeptide (OATP) transporter. In an embodiment, the OATP inhibitor and the anti-methanogenic lovastatin analog or derivative are combined into a single modified-release formulation. Without wishing to be bound by theory, it is believed that inclusion of the OATP inhibitor minimizes absorption of the anti-methanogenic lovastatin analog or derivative from the intestine and/or reduces the enterohepatic recirculation of the anti-methanogenic lovastatin analog or derivative, thereby maximizing retention of the anti-methanogenic lovastatin analog or derivative in the intestine and minimizing any potential systemic side effects of the anti-methanogenic lovastatin analog or derivative. Illustrative OATP inhibitors include, but are not limited to, grapefruit juice or grapefruit juice constituents such as naringin and hesperidin, orange juice and orange juice constituents, apple juice and apple juice constituents, and green tea and green tea extracts such as epicatechin gallate (ECO), epigallocatechin gal late (EGCG). In an embodiment, the OATP inhibitor is released in the intestine prior to release of the anti-methanogenic lovastatin analog or derivative.

In one embodiment, the additional therapeutic agent is a prokinetic agent that facilitates movement of a mass through the intestinal tract. Illustrative prokinetic agents include, but are not limited to, prucalopride (e.g. RESOLOR) or a macrolide antibiotic such as erythromycin. In another embodiment, the additional therapeutic agent is a natural product such as peppermint oil, which alleviates abdominal pain.

The present invention also contemplates the use of additional therapeutic agent that are useful for treating constipation such as, for example, laxatives, guanylate cyclase C agonist (e.g., linaclotide), a serotonin agonist (e.g., prucalorpride, tegaserod), a chloride channel agonist (e.g., lubiprostone), and combinations thereof.

In some embodiments, the additional therapeutic agent is an agent useful for treating IBS (including IBS-C). In some embodiments, the additional therapeutic agent is a selective chloride channel activator, including, for example, molecules derived from prostaglandins such as lubiprostone (e.g. AMITIZA) and those compounds described in U.S. Pat. Nos. 5,284,858, 6,414,016 and 6,583,174, the contents of which are hereby incorporated by reference in their entireties. In some embodiments, the additional therapeutic agent is an agent, including a peptide agent, that increases the secretion of chloride and/or water in the intestines and/or soften stools and/or stimulate bowel movements, such as, for example, linaclotide (e.g. LINZESS) and those compounds described in U.S. Pat. No. 7,304,036, the contents of which are hereby incorporated by reference in their entirety. In some embodiments, the additional therapeutic agent is an agent that relaxes the colon and/or slows the movement of waste through the lower bowel. In some embodiments the additional therapeutic agent is a 5-$HT_3$ antagonist, including, but not limited to, alosetron (e.g. LOTRONEX).

In some embodiments, the additional therapeutic agent is a small molecule that acts as a peripherally selective κ-opioid agonist, such as, for example, EMD-61753 ((N-methyl-N-[(1S)-1-phenyl-2-((3S)-3-hydroxypyrrolidin-1-yl)-ethyl]-2,2-diphenyl-acetamide hydrochloride, ASMADOLINE) and those compounds described in U.S. Pat. No. 6,344,566, the contents of which are hereby incorporated by reference in their entirety. In some embodiments, the additional therapeutic agent is a cholecystokinin antagonist, e.g. one selective for the $CCK_A$ subtype and/or inhibits gastrointestinal motility and reduces gastric secretions, such as, for example, Dexloxiglumide ((4R)-4-[(3,4-dichlorobenzoyl)amino]-5-(3-methoxypropylpentylamino)-5-oxopentanoic acid) and those compounds described in U.S. Pat. No. 5,602,179, the contents of which are hereby incorporated by reference in their entirety. In some embodiments, the additional therapeutic agent is tapentadol (1R,2R)-3-(3-dimethylamino-1-ethyl-2-methyl-propyl)-phenol), as described in US Patent Publication No. 2013/0116334, the contents of which are hereby incorporated by reference in their entirety In some embodiments, the additional therapeutic agent is a laxative, including but not limited to osmotic laxatives (such as, for example, magnesium carbonate, magnesium hydroxide (e.g. Milk of Magnesia), magnesium oxide, magnesium peroxide, magnesium sulfate, lactulose, lactitol, sodium sulfate, pentaerythritol, macrogol, mannitol, sodium phosphate, sorbitol, magnesium citrate, sodium tartrate, laminarid, and polyethylene glycol (e.g., macrogol-containing products, such as MOVICOL and polyethylene glycol 3350, or SOFTLAX, MIRALAX, DULCOLAX BALANCE, CLEARLAX, OSMOLAX OR GLYCOLAX, GOLYTELY, GAVILYTE C, NULYTELY, GLYCOLAX, FORTRANS, TRILYTE, COLYTE, HALFLYTELY, SOFTLAX, LAX-A-DAY, CLEARLAX AND MOVIPREP). In some embodiments, the additional therapeutic agent is a laxative, including but not limited to stimulant laxatives (such as, for example, SENOKOT). Also provided are contact laxatives (e.g. oxyphenisatine, bisacodyl, dantron, phenolphthalein, castor oil, senna glycosides, cascara, sodium picosulfate, and bisoxatin) and bulk-forming laxatives (e.g. ispaghula, ethulose, sterculia, linseed, methylcellulose, triticum, and polycarbophil calcium). In some embodiments, the additional therapeutic agent is an enema, such as, for example, sodium laurilsulfate, sodium phosphate, bisacodyl, dantron, glycerol, oil, and sorbitol. Peripheral opioid antagonists such as, for example, Alvimopan and Methylnaltrexone, as well as Prostaglandins such as, for example, Lubiprostone are also additional therapeutic agents in some embodiments. Also, Linaclotide, Prucalopride, and Tegaserod may be additional therapeutics.

In some embodiments, the additional therapeutic agent is an agent used for long-term pain and cramping, including but not limited to anticholinergics (antispasmodics), such as, for example, dicyclomine (BENTYL) and or antidepressants, including, for example, desipramine (such as, for example, NORPRAMIN), imipramine (TOFRANIL) or nortriptyline (PAMELOR), which are optionally administered at low doses. In low doses, they can help with pain caused by IBS.

In some embodiments, the additional therapeutic agent is fiber supplement, such as, for example, psyllium (METAMUCIL) or methylcellulose (CITRUCEL).

In some embodiments, the additional therapeutic agent is an agent useful for treating obesity. Illustrative agents include, but are not limited to, orlistat, loracaserin, phentermine-topiramate, sibutramine, rimonabant, exenatide, pramlintide, phentermine, benzphetamine, diethylpropion, phendimetrazine, bupropion, and metformin. In various embodiments, the additional agent is an agent that that interfere with the body's ability to absorb specific nutrients in food, such as orlistat, glucomannan, and guar gum. Agents that suppress appetite are also among the additional agents, e.g. catecholamines and their derivatives (such as phentermine and other amphetamine-based drugs), various anti-depressants and mood stabilizers (e.g. bupropion and topiramate), anorectics (e.g. dexedrine, digoxin). Agents that increase the body's metabolism are also among the additional therapeutic agents. In some embodiments, additional therapeutic agents may be selected from among appetite suppressants, neurotransmitter reuptake inhibitors, dopaminergic agonists, serotonergic agonists, modulators of GABAergic signaling, anticonvulsants, antidepressants, monoamine oxidase inhibitors, substance P (NKI) receptor antagonists, melanocortin receptor agonists and antagonists, lipase inhibitors, inhibitors of fat absorption, regulators of energy intake or metabolism, cannabinoid receptor modulators, agents for treating addiction, agents for treating metabolic syndrome, peroxisome proliferator-activated receptor (PPAR) modulators; and dipeptidyl peptidase 4 (DPP-4) antagonists. In some embodiments, additional therapeutic agents may be selected from among amphetamines, benzodiazepines, sulfonyl ureas, meglitinides, thiazolidinediones, biguanides, beta-blockers, ACE inhibitors, diuretics, nitrates, calcium channel blockers, phenlermine, sibutramine, lorcaserin, cetilistat, rimonabant, taranabant, topiramate, gabapentin, valproate, vigabatrin, bupropion, tiagabine, sertraline, fluoxetine, trazodone, zonisamide, methylphenidate, varenicline, naltrexone, diethylpropion, phendimetrazine, repaglinide, nateglinide, glimepiride, pioglitazone, rosiglilazone, and sitagliptin.

In an embodiment, the additional therapeutic agent is an agent for treating pre-diabetes, diabetes, type II diabetes, insulin resistance, glucose intolerance, or hyperglycemia. Examples of drugs include, but are not limited to, alpha-glucosidase inhibitors, amylin analogs, dipeptidyl peptidase-4 inhibitors, GLP1 agonists, meglitinides, sulfonylureas, biguanides, thiazolidinediones (TZD), and insulin. Additional examples of such agents include bromocriptine and Welchol. Examples of alpha-glucosidase inhibitors include but are not limited to acarbose and miglitol. An example of an amylin analog is pramlintide. Examples of dipeptidyl peptidase-4 inhibitors include but are not limited to saxagliptin, sitagliptin, vildagliptin, linagliptin, and alogliptin. Examples of GLP1 agonist include but are not limited to liraglutide, exenatide, exenatide extended release. Examples of meglitinides include but are not limited to nateglinide, and repaglinide. Examples of sulfonylureas include but are not limited to chlorpropamide, glimepiride, glipizide, glyburide, tolazamide, and tolbutamide. Examples of biguanides include but are not limited to metformin, Riomet, Glucophage, Glucophage XR, Glumetza. Examples of thiazolidinedione include but are not limited to rosiglitazone and pioglitazone. Examples of insulin include but are not limited to Aspart, Detemir, Glargine, Glulisine, and Lispro. Examples of combination drugs include but are not limited to glipizide/metformin, glyburide/metformin, pioglitazone/glimepiride, pioglitazone/metformin, repaglinide/metformin, rosiglitazone/glimepiride, rosiglitazone/metformin, saxagliptin/metformin, sitagliptin/simvastatin, sitagliptin/metformin, linagliptin/metformin, alogliptin/metformin, and alogliptin/pioglitazone.

In another embodiment, the additional therapeutic agent is a probiotic. In some embodiments, enteric dietary formulations containing low residual material, such as pre-digested or basic amino acid formulations and other methods and products as described in U.S. Pat. No. 8,110,177 (the contents of which are incorporated herein by reference) may be employed. In a further embodiment, such low residual enteric dietary formulations may be formulated in low carbohydrate and low fat forms either with or without lovastatin analogs or derivatives or red yeast rice which may be particularly useful for weight loss and diabetes. In various embodiments, the probiotic may comprise the following illustrative cells: *E. coli* Nissle 1917, a *lactobacillus* (e.g. *acidophilus, Lactobacillus brevis, L. bulgaricus, L. plantarum, L. rhamnosus, Rhamnosus L. fermentum, L. caucasicus, L. helveticus, L. lactis, L. reuteri* and *L. casei*) or a bifidobacteria (*Bifidobacterium bifidum, B. infantis*) *Streptococcus thermophiles*, and *Enterococcus faecium*. Other suitable probiotics and prebiotics are disclosed for example in R. Spiller, *Aliment Pharmacol Ther* 28, 385-396, the contents of which are hereby incorporated by reference in their entirety.

In some embodiments, a probiotic agent that optionally inhibits the growth of methanogens, for example, *Bifidobacterium* spp. or *Lactobacillus* species or strains, e.g., *L. acidophilus, L. rhamnosus, L. plantarum, L. reuteri, L. paracasei* subsp. *paracasei*, or *L. casei* Shirota, or probiotic *Saccharomyces* species, e.g., *S. cerevisiae*, is selected and/or administered. The probiotic agent that inhibits methanogenesis may be administered in a pharmaceutically acceptable ingestible formulation, such as in a capsule, or for some subjects, consuming a food supplemented with the inoculum is effective, for example milk, yogurt, cheese, meat or other fermentable food preparation. Probiotic agents can inhibit the growth of methanogens, for example, by competing against methanogens for growth and thus reduce or inhibit the growth of methanogens.

Methods of Treatment

In one aspect, the present invention provides methods of treating or preventing a methanogen-associated disorder by administering an anti-methanogenic lovastatin analog or derivative to the intestine (i.e, small and/or large intestine) in a subject in need thereof. In another aspect, the present invention provides methods of treating or preventing a methanogen-associated disorder by administering a modified-release formulation comprising at least one anti-methanogenic lovastatin analog or derivative to the intestine (i.e, small and/or large intestine) in a subject in need thereof.

In some embodiments, the methanogen-associated disorder is a disease or disorder or condition caused by, resulted from, or related to one or more of the abnormal presence or absence of methanogens, abnormal levels of methanogens, overgrowth of methanogens, elevated levels of methanogenesis, elevated enteric methane levels, excessive hydrogen scavenging by hydrogen-consuming methanogens or colonization of methanogens in an abnormal location (e.g., in the small bowel rather than large bowel), either alone or in combination with non-methanogen syntrophic organisms.

Illustrative methanogen-associated disorders include, but are not limited to, enteric methanogen colonization, IBS, IBS-C, IBS-M, constipation, diabetes, type 2 diabetes, metabolic syndrome, insulin resistance, metabolic syndrome, obesity, constipation, chronic constipation, chronic intestinal pseudo-obstruction, systemic sclerosis, systemic lupus, erythematosus, dermatomysitis/polymyositis, periartiytis nodosa, mixed connective tissue disorder, rheumatoid arthritis, spinal cord injury, Parkinson's disease, hypothyroidism/hypoparathyroidism, Hirschsprung's disease, Chagas' disease, intestinal hypoganglionosis, and Ehlers-Danlos Syndrome.

In one aspect, the present invention provides methods of reducing or eliminating the production and/or accumulation of methane in the GI tract by administering an anti-methanogenic lovastatin analog or derivative or a modified-release formulation comprising at least one anti-methanogenic lovastatin analog or derivative to the intestine (e.g. the small and/or large intestine) of a subject in need thereof. In another aspect, the present invention provides methods of reducing or eliminating methane, for example as produced by a methanogen in the GI tract by administering an anti-methanogenic lovastatin analog or derivative or a modified-release formulation comprising at least one anti-methanogenic lovastatin analog or derivative to the intestine (i.e, small and/or large intestine) of a subject in need thereof.

In various embodiments, the methanogen is a microorganism that produces methane as a metabolic byproduct. Methanogens are classified as archaea. Examples of methanogens include but are not limited to *Methanobacterium bryantii, Methanobacterium formicum, Methanobrevibacter arboriphilicus, Methanobrevibacter gottschalkii, Methanobrevibacter ruminantium, Methanobrevibacter smithii, Methanocalculus chunghsingensis, Methanococcoides burtonii, Methanococcus aeolicus, Methanococcus deltae, Methanococcus jannaschii, Methanococcus maripaludis, Methanococcus vannielii, Methanocorpusculum labreanum, Methanoculleus bourgensis (Methanogenium olentangyi, Methanogenium bourgense), Methanoculleus marisnigri, Methanofollis liminatans, Methanogenium cariaci, Methanogenium frigidum, Methanogenium organophilum, Methanogenium wolfei, Methanomicrobium mobile, Methanopyrus kandleri, Methanoregula boonei, Methanosaeta concilii, Methanosaeta thermophile, Methanosarcina acetivorans, Methanosarcina barkeri, Methanosarcina mazei, Methanosphaera stadtmanae, Methanospirillium hungatei, Methanothermobacter defluvii (Methanobacterium defluvii), Methanothermobacter thermautotrophicus (Methanobacterium thermoautotrophicum), Methanothermobacter thermoflexus (Methanobacterium thermoflexum), Methanothermobacter wolfei (Methanobacterium wolfei),* and *Methanothrix sochngenii*.

In one aspect, the present invention provides methods of reducing or eliminating the methane derived from *Methanobrevibacter smithii* in the GI tract. In another aspect, the present invention provides methods of reducing or eliminating methane, for example as produced by *Methanobrevibacter smithii*, in the GI tract by administering an anti-methanogenic lovastatin analog or derivative or a modified-release formulation comprising at least one anti-methanogenic lovastatin analog or derivative to the intestine (i.e, small and/or large intestine) in a subject in need thereof.

In various embodiments, the present invention relates to the substantial reduction of methane gas in a subjects GI tract (e.g. eradication of intestinal methane). In some embodiments the present formulations and methods prevent the increase in levels of methane gas in a subject's GI tract. In some embodiments, the patient's GI methane levels (as assessed by methods described herein and methods known in the art) are reduced to about 1 ppm, or about 2 ppm, or about 3 ppm, or about 4 ppm, or about 5 ppm, or about 10 ppm, or about 15 ppm, or about 20 ppm, or about 25 ppm, or about 30 ppm, or about 35 ppm, or about 40 ppm, or about 45 ppm, or about 50 ppm, or about 55 ppm, or about 60 ppm, or about 65 ppm, or about 70 ppm, or about 75 ppm, or about 80 ppm, or about 85 ppm, or about 90 ppm, or about 100 ppm. In various embodiments, the present formulations and methods reduce the patient's GI methane levels to less than about 250 ppm, or less than about 225 ppm, or less than about 200 ppm, or less than about 175 ppm, or less than about 150 ppm, or less than about 125 ppm, or less than about 100 ppm, or less than about 50 ppm. In various embodiments, substantial reduction of methane gas is not accompanied by a substantial reduction in hydrogen gas.

In various embodiments, the present invention relates to the treatment of IBS, including IBS-C as described by ICD-10 (International Statistical Classification of Diseases and Related Health Problems, WHO edition). In various embodiments, the present invention relates to the treatment of irritable colon, as classified in ICD-10 as [K58], IBS may include irritable bowel syndrome without diarrhea, as classified in ICD-10 as [K58.9], Irritable bowel syndrome without diarrhea may also include irritable bowel syndrome not otherwise specified (NOS). Further, the diseases as classified in ICD-10 as K59 are also included (e.g. constipation; K59.1 Functional diarrhea; K59.2 Neurogenic bowel, not elsewhere classified; K59.3 Megacolon, not elsewhere classified (including dialatation of colon, toxic megacolon, megacolon in Chagas disease (B57.3), congenital (aganglionic) (Q43.1), and Hirschsprung disease (Q43.1)); K59.4 Anal spasm (including Proctalgia fugax); K59.8 Other specified functional intestinal disorders (including atony of colon) and K59.9 Functional intestinal disorder, unspecified).

In various embodiments, the present invention relates to the treatment of spastic colon, nervous colitis, mucous colitis, functional colitis or colonic neurosis. In various embodiments, the present invention relates to the treatment of diseases that have been described as sigma elongatum mobile, cecum mobile, chronic colitis, splanchnoptosia and the like. Typological classification of the disease generally include convulsive large bowel, diarrhea nervosa and colica mucosa, and the disease may also be classified in convulsive constipation type, atonic constipation type, intestinal gas syndrome, or chronic celiopathy.

Furthermore, IBS may also include cholangiodyskinesia, gastric emptying hypofunction, hysteric globus, non-specific esophagus functional abnormalities, nervous vomiting, recurrent abdominal pain, simple constipation, chronic idiopathic constipation and the like. As diagnostic criteria of IBS those of NIH, Manning, Cook et al. and the like are suitable (see Asakura, *Clinical Digestive Internal Medicine,* 8 (8): 1373-1381 (1993), the contents of which are hereby incorporated by reference in their entirety).

In various embodiments, the present invention relates to the treatment of IBS, including IBS-C of varying stages or severity. In one embodiment, stages or severity of the IBS may be evaluated with a health-related quality of life (FIRQoL) evaluation. In some embodiments, the stage or severity of the disease in the patient to be treated is assessed by an evaluation of one or more of patient pain, distension, bowel dysfunction and quality of life/global well-being.

In some embodiments, the stage or severity of the disease in the patient to be treated is assessed by the Rome Scale (for the last 3 months with symptom onset at least 6 months prior to diagnosis: recurrent abdominal pain or discomfort (e.g. uncomfortable sensation not described as pain.) at least 3 days/month in the last 3 months associated with two or more of improvement with defecation, onset associated with a change in frequency of stool, and onset associated with a change in the form (appearance) of stool.

In some embodiments, the stage or severity of the disease in the patient to be treated is assessed by the Kruis scale (*Gastroenterology* 87: 1-7, the contents of which are hereby incorporated by reference). This scale incorporates both the "cardinal" symptoms (pain, bloating, altered bowel function) and "red flag" signs of potential underlying organic disease that would thus exclude an IBS diagnosis. IBS is diagnosed if the sum of scores>44.

TABLE 1

Kruis Scoring System. IBS is diagnosed if the sum of scores >44

| Parameter | Score |
|---|---|
| Signs | |
| Pain, flatulence, or bowel irregularity | 34 |
| Duration of symptoms >2 yr | 16 |
| Description of abdominal pain (Scale, from burning to "not so bed") | 23 |
| Alternating diarrhea and constipation | 14 |
| Red Flags | |
| Abnormal physical findings of history pathognomonic of other disease | −47 |
| ESR > 10 mm/h | −13 |
| WBC > ×10$^9$ | −50 |
| Anemia | −98 |
| History of blood in stool | −98 |

In some embodiments, the patient is evaluated with the assessment described in Francis, et al *Aliment Pharmacol Ther* 1997; 11: 395-402, the contents of which are hereby incorporated by reference in their entirety. For instance, a scoring system based on patient ranking of pain, distension, bowel dysfunction and quality of life/global well-being on a scale of up to 500 is used. Mild, moderate and severe cases were indicated by scores of 75 to 175, 175 to 300 and >300. In some embodiments, the patient of the present invention has a score of 75 to 175. In some embodiments, the patient of the present invention has a score of 175 to 300. In some embodiments, the patient of the present invention has a score of >300. In some embodiments the scales described in Wong and Drossman (*Expert Rev. Gastroenterol. Hepatol.* 4(3), (2010), the contents of which are hereby incorporated by reference in their entirety). For example, in some embodiments, the patients of the present invention are evaluated for the parameters of dysphoria, activity interference, body image, health worry, food avoidance, social reaction, and sexual relationships and optionally scored on a 0-100 as described on the Patrick scale; and/or the patients of the present invention are evaluated for the parameters of daily activities, emotional impact, family relations, food, sleep and fatigue, social impact, sexual relations symptoms and optionally scored on a 0-216 as described on the Groll scale; the patients of the present invention are evaluated for the parameters of activities, anxiety, diet, sleep, discomfort, health perception, disease coping and stress and optionally scored on a 0-100 as described on the Chassany scale; the patients of the present invention are evaluated for the parameters of emotional health, mental health, sleep, energy, physical functioning, diet, social role, physical role, and sexual relations and optionally scored on a 0-100 as described on the Hahn scale; and/or the patients of the present invention are evaluated for the parameters of bowel symptoms, fatigue, activity impairment, emotional dysfunction and optionally scored as domain average scores (calculated by dividing the domain sum score by the number of items: range 1-7) as described on the Wong scale.

In some embodiments, patients may be stratified based on one or more of methane detection (e.g. via breath test) and methanogen detection (e.g. via PCR, e.g. qPCR). In some embodiments, the patient is considered methane breath test positive if the subject presents with greater than about 3 ppm methane. In some embodiments, the patient of the present invention has greater than about $10^4$, or about $10^5$, or about $10^6$ copies of *M. smithii* per grams of wet stool. In some embodiments, the patient of the present invention is defined by a measurement of the fractional methanogen contribution to the total microbial content of the feces. In some embodiments, the patient has greater than about 0.5%, or about 0.6%, or about 0.7%, or about 0.8%, or about 0.9%, or about 1.0%, or about 1.1%, or about 1.2%, or about 1.3%, or about 1.4%, or about 1.5%, or about 2.5% *M. smithii* fraction of the total microbial content of the feces.

In some embodiments, methods of the present invention treat or prevent constipation. Constipation may be associated with, for example, chemotherapy, *vinca* alkaloids, oxaliplatin, taxanes, thalidomide, opioids, sedatives, anticholinergics, gastrointestinal antispasmodics, antiparkinsonism agents, antidepressants, phenothiazines, calcium- and aluminum-based antacids, diuretics, tranquilizers, sleeping medications, general anesthesia, pudendal blocks, inadequate fluid intake, excessive use of laxatives and/or enemas, prolonged immobility, inadequate exercise, spinal cord injury or compression, fractures, fatigue, weakness, inactivity, bedrest, cardiac problems, diverticulitis, neurological lesions, cerebral tumors, spinal cord injury, spinal cord compression, paraplegia, cerebrovascular accident with paresis, weak abdominal muscles, hypothyroidism, lead poisoning, uremia, dehydration, hypercalcemia, hypokalemia, hyponatremia, anorexia, immobility, antidepressants, inability to increase intra-abdominal pressure, emphysema, neuromuscular impairment of the diaphragm, neuromuscular impairment of abdominal muscles, abdominal hernias, malnutrition, cachexia, anemia, carcinoma, and senility.

In various embodiments, the constipation is associated with IBS. But, the present invention, in some embodiments, can also relate to chronic functional constipation.

In various embodiments, the present invention relates to the treatment of increased visceral hypersensitivity. In various embodiments, the present invention relates to the treatment of one or more of stomachaches, pain, nausea, straining, and bloating and/or gas. The present formulations and methods also treat one or more of as hard stools, infrequent stools, difficulty or straining at stools, feeling of being unable to completely empty during a bowel movement, and the sensation of wanting to go but not being able to.

In various embodiments, the present invention relates to the treatment for diabetes (type 1 or type 2) and/or glucose intolerance. In some embodiments, the present invention relates to a method for treating patient at risk of diabetes, one or more of insulin resistance, prediabetes, impaired fasting glucose (IFG), impaired glucose tolerance (IGT), and acanthosis nigricans.

In some embodiments, methods for inducing weight loss or preventing weight gain (or treating or preventing obesity or inducing weight loss or preventing weight gain in a patient that does not substantially change caloric intake), comprising administering an anti-methanogenic lovastatin analog or derivative or a modified-release formulation of the present invention are provided. Patients may have undertaken or will undertake a surgery of the digestive system; be greater than about 80-100 pounds overweight; have a BMI of greater than about 35 kg/m$^2$; or have a health problem related to obesity In some embodiments, administration of the anti-methanogenic lovastatin analog or derivative or the modified-release formulation of the present invention does not confer cholesterol-lowering cardiovascular effects associated with systemic administration. For example, the present formulations and methods may avoid or reduce a subject's systemic exposure to the lovastatin analog or derivative. For example, the present formulations and methods may provide an average reduction of less than about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, or about 2% in serum LDL-C levels after treatment.

In some embodiments, the patient is one who does not require statins or statin analogs or derivatives for their cardiovascular therapeutic uses. In some embodiments, the patient is one who does not require statins or statin analogs or derivatives for their cardiovascular therapeutic uses and is methane-positive (e.g. as assessed by the methods described herein such as the methane breath test and qPCR).

By maximizing retention of the anti-methanogenic lovastatin analog or derivative to the intestines, the methods of the invention also minimize the side effects associated with systemic release. For example, the present method prevents and/or minimizes various adverse effects associated with lovastatin or lovastatin analog or derivative usage including, muscle-associated adverse effects, such as myositis, myalgia, rhabdomyolysis, drug-drug-interactions, cognitive effects, increased cancer risk, increases in liver enzymes, hemorrhagic stroke, increase in blood glucose levels, sleep disorders, peripheral neuropathy, sexual dysfunction, thyroid dysfunction, renal toxicity, irritability, shortness of breath, hyperkalemia, weight gain, neurodegenerative disease, pancreatitis, liver pathology, mitochondrial syndromes, dermatologic conditions, dry mouth, cataracts, olfaction, hematalogic and bone marrow adverse effects, hypotension, gastrointestinal adverse effects, including, ulcerative colitis and gastric ulceration, fatigue and headache. In some embodiments, the methods of the invention also minimizes the following side effects associated with systemic release: muscle pain, tenderness, or weakness, lack of energy, weakness, fever, dark colored urine, jaundice, pain in the stomach, including the upper right part of the stomach, nausea, unusual bleeding or bruising, loss of appetite, flu-like symptoms, rash, hives, itching, difficulty breathing or swallowing, and swelling of the face, throat, tongue, lips, eyes, hands, feet, ankles, or lower legs, hoarseness.

Accordingly, the anti-methanogenic lovastatin analog or derivative or the modified-release formulation of the present invention may be used to target subjects where systemic statin or statin analog or derivative levels are undesirable. In one embodiment, the subject may be women and children who are otherwise healthy and have no need for a cardiovascular medicine (as characterized, for example, as having low or zero myocardial event risk factors as per the ATP III Guideline). In another embodiment, the subject may be a child with IBS-C who has no need for a cholesterol-lowering agent. In such embodiments, administration of the anti-methanogenic lovastatin analog or derivative or the modified-release formulation of the present invention results in an average reduction of less than about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, or about 2% in serum LDL-C levels after treatment.

The anti-methanogenic lovastatin analog or derivative or the modified-release formulation of the present invention may also be utilized as part of a treatment regimen wherein a subject is provided with an initial anti-methanogenic therapy followed by a chronic anti-methanogenic or methane-reducing and/or eliminating maintenance therapy.

The initial anti-methanogenic therapy may employ agents other than statins or statin analogs or derivatives such as, for example, antibiotics which eradicate the methanogens. For example nitroimidazoles such as metronidazole, metronidazole esters and/or isomers or hydrophobic imidazole derivatives or rifaximin or neomycin sufficient to eradicate, substantially reduce, or reduce the enteric methanogen colonization may be used. Such initial therapy may be for 1, 2,3, 4, 5, 6, 7, 8, 9, 10, 14, 28, 42, 56, 60, 90, 120 or 180 days or more. Examples of antibiotics include but are not limited to aminoglycosides (e.g., amikacin, gentamicin, kanamycin, neomycin, netilmicin, streptomycin, tobramycin, paromomycin), ansamycins (e.g., geldanamycin, herbimycin), carbacephems (e.g., loracarbef), carbapenems (e.g., ertapenem, doripenem, imipenem, cilastatin, meropenem), cephalosporins (e.g., first generation: cefadroxil, cefazolin, cefalotin or cefalothin, cefalexin; second generation: cefaclor, cefamandole, cefoxitin, cefprozil, cefuroxime; third generation: cefixime, cefdinir, cefditoren, cefoperazone, cefotaxime, cefpodoxime, ceftazidime, ceftibuten, ceftizoxime, ceftriaxone; fourth generation: cefepime; fifth generation: ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin), antibiotic polypeptides (e.g., bacitracin, colistin, polymyxin b), quinolones (e.g., ciprofloxacin, enoxacin, gatifloxacin, levofloxacin, lomefloxacin, moxifloxacin, norfloxacin, ofloxacin, trovafloxacin), rifamycins (e.g., rifampicin or rifampin, rifabutin, rifapentine, rifaximin), sulfonamides (e.g., mafenide, prontosil, sulfacetamide, sulfamethizole, sulfanilamide, sulfasalazine, sulfisoxazole, trimethoprim, trimethoprim-sulfamethoxazole (co-trimoxazole, "tmp-smx"), and tetracyclines (e.g., demeclocycline, doxycycline, minocycline, oxytetracycline, tetracycline) as well as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin combination, and tinidazole.

Following the initial therapy, a subject may be placed on maintenance therapy in order to maintain reduced methanogen and/or methane levels. In some embodiments, the maintenance therapy utilizes a lovastatin analog or derivative or a modified-release formulation of the present invention. In an embodiment, the initial therapy includes an antibiotic followed by a chronic maintenance regimen of low dose lovastatin analog or derivative formulations. In various embodiments, the maintenance regiment may be administered for at least 1 week, at least 2 weeks, at least 3 weeks, at least 4 weeks, at least one month, at least two months, at least three months, at least four months, at least five months, at least six months, at least seven months, at least eight months, at least nine months, at least ten months, at least eleven months, at least 1 year, at least 2 years, at least 3 years, at least 4 years, at least 5 years, at least 10 years, or indefinitely.

The anti-methanogenic lovastatin analog or derivative or the modified-release formulation of the present invention may be utilized solely for chronic maintenance therapy. In various embodiments, the present invention provides a method of treating previously methane positive patients who do not have one or more of cardiovascular disease, an LDL level of 190 mg/dL or higher, Type 2 diabetes who are between 40 and 75 years of age, an estimated 10-year risk of cardiovascular disease of 7.5 percent or higher who are between 40 and 75 years of age with an anti-methanogenic lovastatin analog or derivative or a modified-release formulation herein in order to maintain their methane negative status. Accordingly, in some embodiments, the anti-methanogenic lovastatin analog or derivative or the modified-release formulation of the present invention finds use as a prevention measure in a high risk patient.

In various embodiments, methods of the invention are useful in treatment a human subject. In some embodiments, the human is a pediatric human. In other embodiments, the human is an adult human. In other embodiments, the human is a geriatric human. In other embodiments, the human may be referred to as a patient. In some embodiments, the human is a female. In some embodiments, the human is a male.

In certain embodiments, the human has an age in a range of from about 1 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old. In one embodiment, the human is a child. In one embodiment, the human is a female.

Methods to Determine Methanogen Levels/Diagnostic and Patient Selections

Intestinal methanogen and/or methane levels can be determined by breath tests that measure breath methane levels. Breath testing may be utilized to identify subjects who are "methane-positive" and who can potentially benefit from methods of the present invention. Further, breath testing can also be used to monitor the efficacy of treatment. Breath testing analysis methods and equipment are known in the art (see, for example, International Patent Publication WO/2014/152754, the entire contents of which are incorporated by reference herein). Examples of such equipment include, for example, the QuinTron BreathTracker gas chromatographic (GC) analyzer or the QuinTron BreathTracker device (QuinTron Instrument Company, Inc., Milwaukee, WI).

Further, abnormal lactulose breath test results are common in subjects with IBS and therefore the present invention provides for the use of lactulose breath tests in evaluating patients. In some embodiments, a patient is evaluated with a lactulose breath test before and/or after administration with the anti-methanogenic lovastatin analog or derivative or the modified release formulations described herein.

In general, individuals having a breath methane level of at least about 3 ppm are generally associated with methanogen-associated disorders and are likely to benefit from methods of the present invention. Alternatively, methods of the invention may be practiced on subjects having a breath methane level of at least 1 ppm, at least 1.5 ppm, at least 2 ppm, at least 2.5 ppm, at least 3 ppm, at least 3.5 ppm, at least 4 ppm, at least 5 ppm, at least 6 ppm, at least 7 ppm, at least 8 ppm, at least 9 ppm, at least 10 ppm.

One method for measuring methanogen levels involves calculation of a subject's breath methane area under the curve (BM-AUC). This method involves obtaining multiple breath samples averaging about 15 minutes apart for a period of about 90 minutes, or about 120 minutes, or for up to 4 hours or more at potentially less frequent intervals. The time period results are used to calculate a person's BM-AUC. For example, a subject may undergo a such as lactulose, xylose, lactose, or glucose breath test after a 12 hour fast. The breadth test may comprise a baseline breath measurement after which the subject ingests about 10 g of such as lactulose, xylose, lactose, or glucose. Following lactulose ingestion, the subject is then asked to provide a breath sample about every 15 minutes for about 90 to about 120 minutes to determine methane production. BM-AUC may be utilized for more precisely determining and monitoring, for example, the efficacy of the anti-methanogenic therapy. BM-AUC measurements could also be utilized to segregate "methane positive" from "methane negative" subjects for improved clinical decision making. BM-AUC may be compared to or utilized with measurement of methanogen levels in stool samples via PCR, e.g. qPCR. Alternatively, measurement of methanogen levels in stool samples via PCR, e.g. qPCR may supplant the use of a breath test. More precise techniques may also involve measurement of breath methane taking into account and subtracting ambient methane levels.

Spot breath methane analysis via commercially available equipment such as BreathTracker may be used in discriminating "methane-positive" from "methane-negative" individuals, and monitoring the success, failure, dose titration, dosing schedule (daily or non-daily, for example) of the anti-methanogenic lovastatin analog or derivative or the modified-release formulation described herein. For example, the lowest minimum effective dose may be identified as such. Additional instruments and techniques for measuring methane levels include, but are not limited to, cavity enhanced absorption techniques such as a LGR-FMR methane measurement instrument having a range as low as 0.01 ppm (Los Gatos Research, Inc., Mountain View, Calif.), wavelength-scanned cavity down-ring spectroscopy, carbon isotope analysis (G2132-i13C, Picarro, Inc, Santa Clara, Calif.), gas chromatography, mass spectroscopy, membrane extracted carbon isotope analysis (Pollock, 2012 GSA Annual Meeting, "Membrane Extracted Carbon Isotope Analysis Of Dissolved Methane"), headspace gas chromatography with FID detector and GC combustion with IRMS instruments, for example. Other instruments having the ability to measure low concentration breath methane levels at higher precision than the clinical validated instrument marketed as the QuinTron BreathTracker include high precision breath methane analysis (HPBMA). Use of HPBMA may be used to test spot breath methane levels or in BM-AUC form.

In some embodiments, detection of hydrogen quantity and methane quantity is by gas chromatography with mass spectrometry and/or radiation detection to measure breath emissions of isotope-labeled carbon dioxide, methane, or hydrogen, after administering an isotope-labeled substrate that is metabolizable by gastrointestinal bacteria but poorly digestible by the human host, such as lactulose, xylose, mannitol, or urea (e.g., G. R. Swart and J. W. van den Berg, $^{13}C$ breath test in gastrointestinal practice, Scand. J. Gastroenterol. [Suppl.] 225:13-18 [1998]; S. F. Dellert et al., The $^{13}C$-xylose breath test for the diagnosis of small bowel bacterial overgrowth in children, J. Pediatr. Gastroenterol. Nutr. 25(2): 153-58 [1997]; C. E. King and P. P. Toskes, Breath tests in the diagnosis of small intestinal bacterial overgrowth, Crit. Rev. Lab. Sci. 21 (3):269-81 [1984]). A poorly digestible substrate is one for which there is a relative or absolute lack of capacity in a human for absorption thereof or for enzymatic degradation or catabolism thereof.

Suitable isotopic labels include $^{13}C$ or $^{14}C$. For measuring methane suitable isotopic labels can also include $^2H$ and $^3H$ or $^{17}O$ and $^{18}O$, as long as the substrate is synthesized with the isotopic label placed in a metabolically suitable location in the structure of the substrate, i.e., a location where enzymatic biodegradation by intestinal microflora results in the isotopic label being sequestered in the gaseous product. If the isotopic label selected is a radioisotope, such as $^{14}C$, $^3H$, or $^{15}O$, breath samples can be analyzed by gas chromatography with suitable radiation detection means (e.g., C. S. Chang et al., Increased accuracy of the carbon-14 D-xylose breath test in detecting small-intestinal bacterial overgrowth by correction with the gastric emptying rate, Eur. J. Nucl. Med. 22(10): 1118-22 [1995]; C. E. King and P. P. Toskes, Comparison of the 1-gram [$^{14}C$]xylose, 10-gram lactulose-$H_2$, and 80-gram glucose-$H_2$ breath tests in patients with small intestine bacterial overgrowth, Gastroenterol. 91 (6): 1447-51 [1986]; A. Schneider et at, Value of the $^{14}C$-D-xylose breath test in patients with intestinal bacterial overgrowth, Digestion 32(2):86-91 [1985]).

In various embodiments, treatments using the anti-methanogenic lovastatin analog or derivative or the modified-release formulation of the invention result in a reduction of breath methane level of at least about 1 ppm, at least about 2 ppm, at least about 3 ppm, at least about 4 ppm, at least about 5 ppm, at least about 6 ppm, at least about 7 ppm, at least about 8 ppm, at least about 9 ppm, at least about 10 ppm, at least about 20 ppm, at least about 30 ppm, at least about 40 ppm, at least about 50 ppm, at least about 60 ppm, at least about 70 ppm, at least about 80 ppm, at least about 90 ppm, at least about 100 ppm, at least about 110 ppm, at least about 120 ppm, at least about 130 ppm, at least about 140 ppm, at least about 150 ppm, at least about 160 ppm, at least about 170 ppm, at least about 180 ppm, at least about 190 ppm, at least about 200 ppm, at least about 210 ppm, at least about 220 ppm, at least about 230 ppm, at least about 240 ppm, and at least about 250 ppm.

The samples used for the present invention include a patient's breath. In various embodiments, measurement of methanogen levels in stool samples via PGR, e.g. qPCR or other molecular biology approaches, for example, is also provided. Further, aspirates of the fluid in the GI tract may be analyzed for methanogen and/or methane levels. Also mucosal biopsies from a site in the gastrointestinal tract may be analyzed for methanogen and/or methane levels.

Methods of "quantitative" amplification are well known to those of skill in the art. For example, quantitative PGR involves simultaneously co-amplifying a known quantity of a control sequence using the same primers. This provides an internal standard that may be used to calibrate the PGR reaction. Detailed protocols for quantitative PGR are provided in, for example, Innis, et al. (1990) PGR Protocols, A Guide to Methods and Applications, Academic Press, Inc. N.Y.). Measurement of DNA copy number at microsatellite loci using quantitative PGR analysis is described in, for example, Ginzonger, et al. (2000) Cancer Research 60:5405-5409. The known nucleic acid sequence for the genes is sufficient to enable one of skill in the art to routinely select primers to amplify any portion of the gene. Fluorogenic quantitative PGR may also be used in the methods of the invention. In fluorogenic quantitative PGR, quantitation is based on amount of fluorescence signals, e.g., TaqMan and Sybr green.

Other suitable amplification methods include, but are not limited to, ligase chain reaction (LCR) (see, for example, Wu and Wallace (1989) Genomics 4: 560, Landegren, et al. (1988) Science 241:1077, and Barringer et al. (1990) Gene 89: 117), transcription amplification (Kwoh, et al. (1989) Proc. Natl. Acad. Sci. USA 86: 1173), self-sustained sequence replication (Guatelli, et al. (1990) Proc. Nat. Acad. Sci. USA 87: 1874), dot PGR, and linker adapter PGR, etc.

In still other embodiments of the methods provided herein, sequencing of individual nucleic molecules (or their amplification products) is performed. In one embodiment, a high throughput parallel sequencing technique that isolates single nucleic acid molecules of a population of nucleic acid molecules prior to sequencing may be used. Such strategies may use so-called "next generation sequencing systems" including, without limitation, sequencing machines and/or strategies well known in the art, such as those developed by Illumina/Solexa (the Genome Analyzer; Bennett et al. (2005) Pharmacogenomics, 6:373-20 382), by Applied Biosystems, Inc. (the SOLID Sequencer; solid.appliedbiosystems.com), by Roche (e.g., the 454 GS FLX sequencer; Margulies et al. (2005) Nature, 437:376-380; U.S. Pat. Nos. 6,274,320; 6,258,568; 6,210,891) and others. Other sequencing strategies such as stochastic sequencing (e.g., as developed by Oxford Nanopore) may also be used, e.g., as described in International Patent Publication No. WG/2010/004273.

In still other embodiments of the methods provided herein, deep sequencing can be used to identify and quantify the methanogen or methanogen syntrophic microorganism. These techniques are known in the art.

Kits

The present invention is also directed to a kit for the treatment of a methanogen-associated disorder. The kit is an assemblage of materials or components, including at least one of the anti-methanogenic lovastatin analog or derivative or the modified-release formulations described herein. The kit may further include materials and components for the quantification of methanogens. The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to affect a desired outcome, such as to treat a disorder associated with methanogens. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials and components assembled in the kit can be provided to the practitioner store in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label which indicates the contents and/or purpose of the kit and/or its components.

EXAMPLES

Example 1: Evaluation of Anti-Methanogenic Lovastatin Analogs or Derivatives in Stool Samples of Human IBS-C Patients Fresh stool samples were provided by two methane-producing human IBS-C patients (breath methane>10 ppm) who had provided an informed consent. Different concentrations of stool from each patient were homogenized in deoxygenated PBS (3 ml PBS/2 g stool) inside an anaerobic incubation chamber. Plead gas was extracted through a stopcock at various timepoints (0, 90, 180 and 270 minutes, and following overnight incubation) and methane levels in the head gas at each timepoint were analyzed by gas chromatography using a Quintron SC gas chromatograph (Quintron Instrument Company, Milwaukee, Wis.). 4 g of stool appeared adequate to capture both methane-producing subjects within an acceptable concentration range.

The effects of lovastatin lactone, lovastatin ß-hydroxyacid and lovastatin diol on methane production were evaluated by incubating various concentrations of these molecules (0 mg, 0.5 mg, 1 mg, 5 mg and 10 mg of statin per g of human stool) with human stool homogenates in an anaerobic chamber as described above. Plead gas samples were drawn from each flask for methane analysis at baseline and at 90 minute intervals for 3 hours, followed by a final sample after overnight incubation (~720 min).

Figure 4:
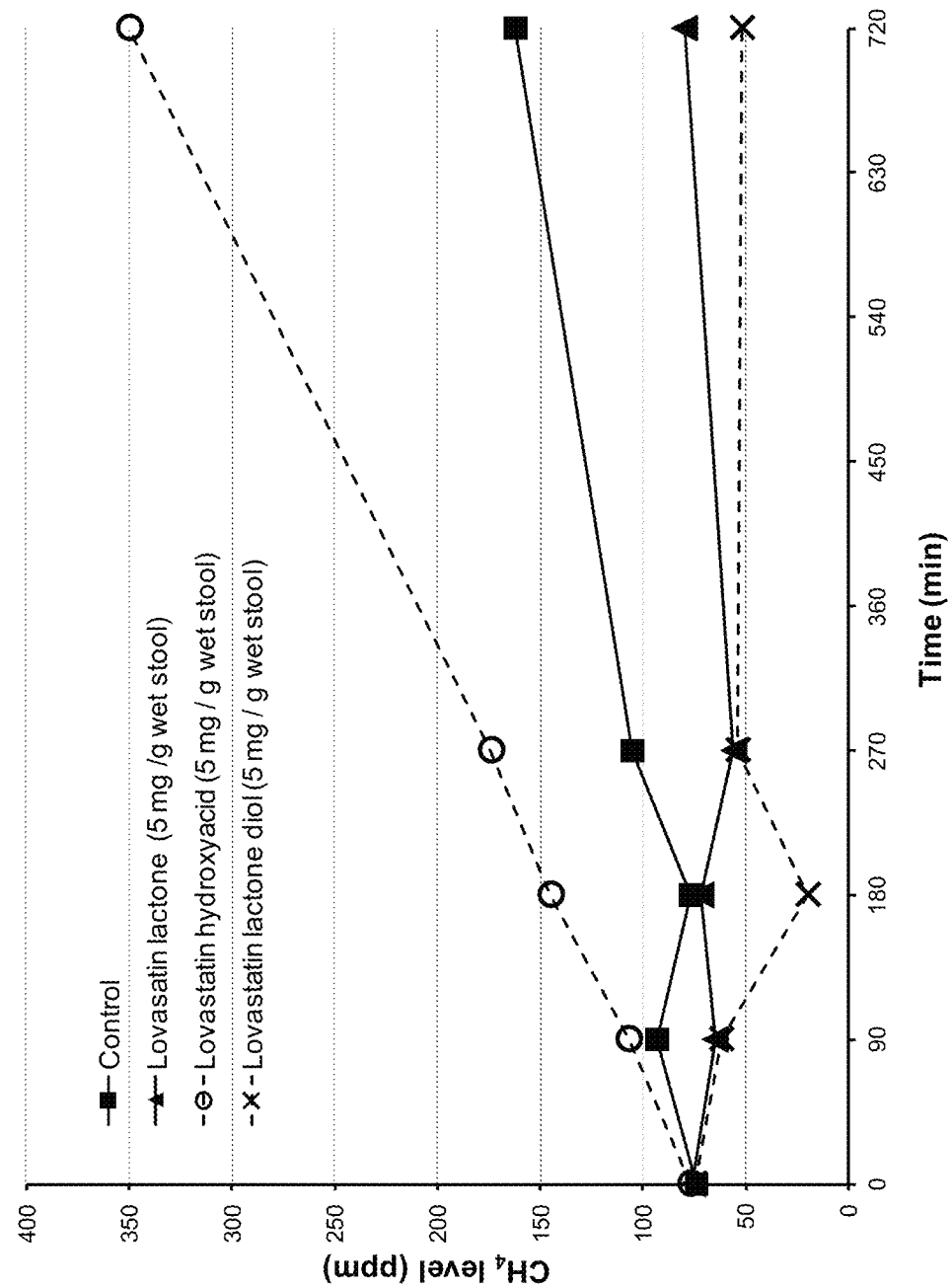
FIG. 4 shows illustrative methane versus time profiles for human stool samples treated with the different lovastatin species.

Illustrative methane vs. time profiles for human stool samples treated with the different lovastatin species are presented in FIG. 4. Lovastatin lactone and lovastatin diol lactone were both effective inhibitors of methane production in human stool; however, lovastatin R-hydroxyacid was ineffective as an inhibitor of methane production in this system.

Further studies using this experimental design are used to evaluate the compounds of Formulae Ia-e, IIa-e, IIIa-e, IVa-e, V, VI, VII, VIII, IX, X, XI, XII, XIII, XIV, XV, XVI, XVII, XVIII, XIX, XX, XXI, XXII, XXIII, XXIV, XXV, XVI, XVII, XVIII, XVIX, XXX, XXXI, XXXII, XXXIII, XXXIV, XXXV and XXXVI.

Example 2: Animal Studies of Anti-Methanogenic Lovastatin Analogs or Derivatives The effects of anti-methanogenic lovastatin analogs or derivatives in a rat model of diet-induced constipation and M. smithii proliferation are evaluated. Adult, male Sprague-Dawley rats are placed on a high fat diet (e.g. about 60% kcal from fat, Teklad high fat diet TD.06414, Harlan Laboratories Inc, Madison, Wis.) for about 7 weeks. The rats are assessed for increased M. smithii by qPCR before and after the diet and then divided into 3 groups. Group 1 is given anti-methanogenic lovastatin analogs or derivatives (e.g. compounds of Formulae Ia-e, IIa-e, IIIa-e, IVa-e, V, VI, VII, VIII, IX, X, XI, XII, XIII, XIV, XV, XVI, XVII, XVIII, XIX, XX, XXI, XXII, XXIII, XXIV, XXV, XVI, XVII, XVIII, XVIX, XXX, XXXI, XXXII, XXXIII, XXXIV, XXXV, and XXXVI), optionally in the lactone form (about 1.5 mg/rat), group 2 is given anti-methanogenic lovastatin analogs or derivatives (e.g. compounds of Formulae Ia-e, IIa-e, IIIa-e, IVa-e, V, VI, VII, VIII, IX, X, XI, XII, XIII, XIV, XV, XVI, XVII, XVIII, XIX, XX, XXI, XXII, XXIII, XXIV, XXV, XVI, XVII, XVIII, XVIX, XXX, XXXI, XXXII, XXXIV, XXXV, and XXXVI) hydroxy acid (about 1.5 mg/rat), and the Group 3 was gavaged with a placebo. Each group is gavaged daily for about 10 days. Three day stool collections are performed to assess average stool wet-weight and daily variability prior to commencing the high fat diet, after about 7 weeks of high fat diet, and the finals days of the lovastatin gavage (still on high fat diet). On day 10 of the gavage, rats are euthanized and DMA is extracted from contents of ligated bowel segments (ileum, jejunum, duodenum, cecum and left colon). qPCR is performed using primers for total luminal bacteria and M. smithii.

The studies of Example 2 are optionally carried out using lovastatin diol lactone.

Example 3: Clinical Evaluation of Different Release Profiles

Figure 5:
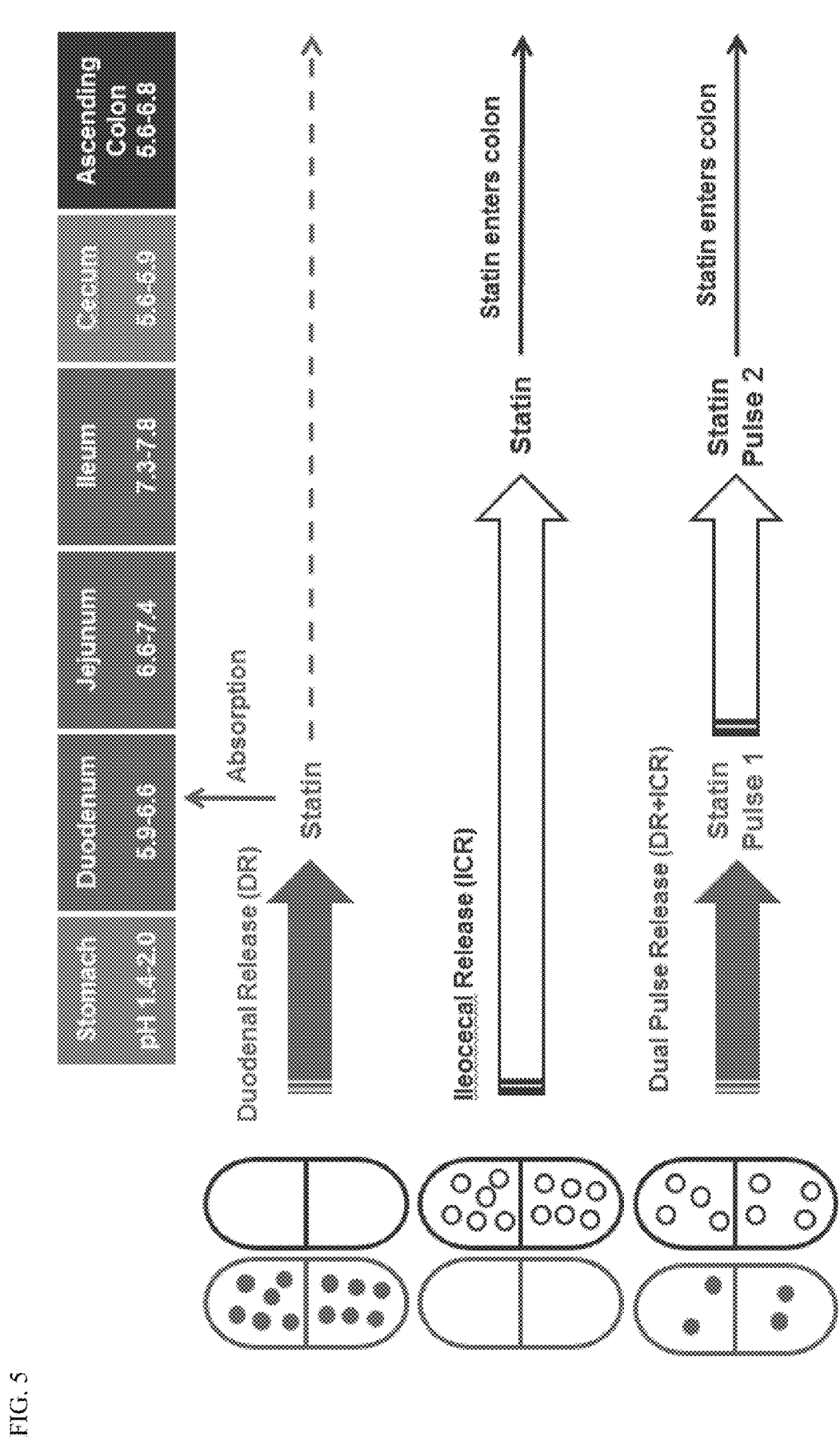
FIG. 5 depicts various embodiments of modified-release formulations in the form of capsules that delivers either one or two doses of anti-methanogenic lovastatin analogs or derivatives to the intestines.
Figure 6:
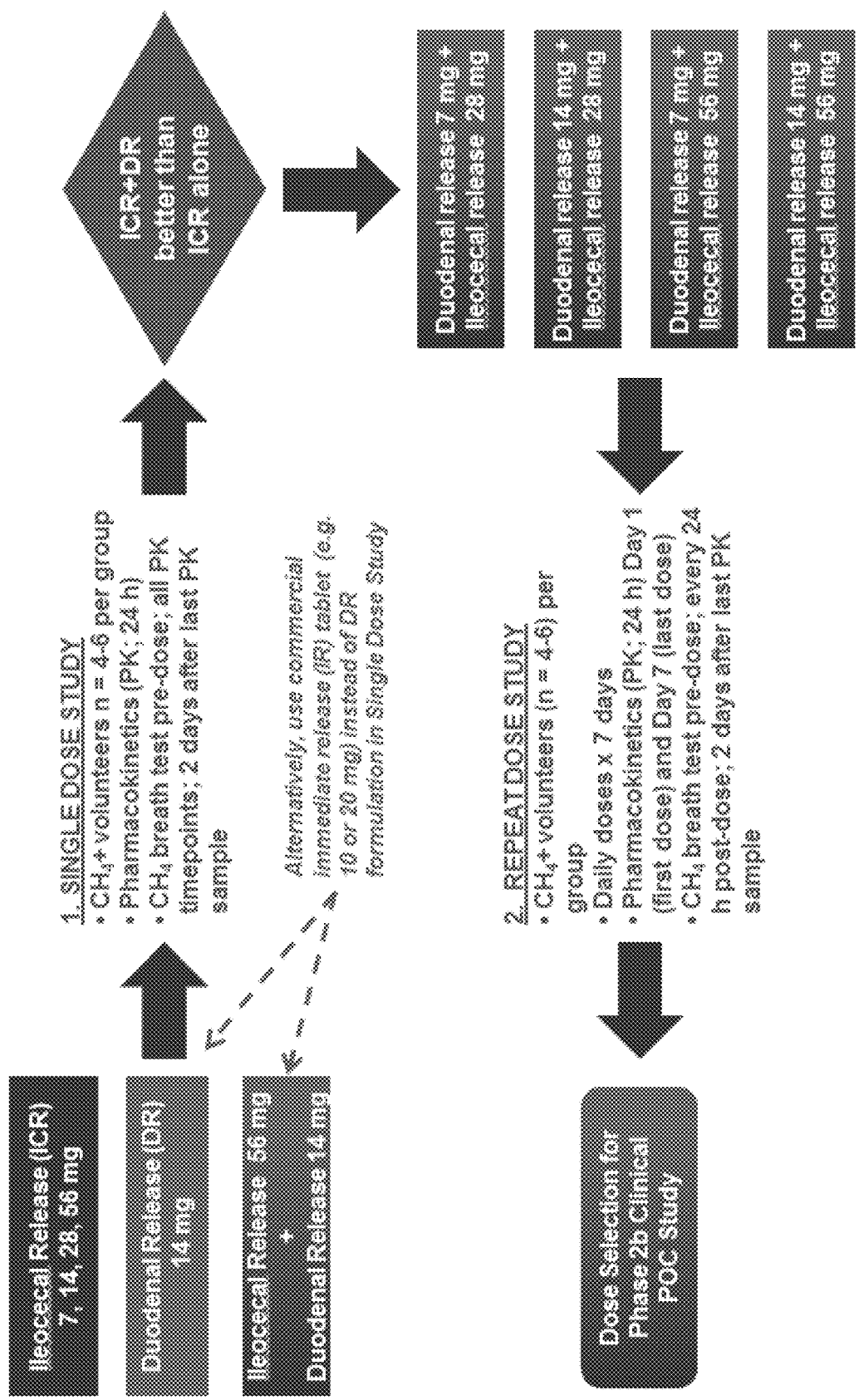
FIG. 6 depicts a clinical study design with the present compositions.

The present formulations are evaluated clinically as shown in FIG. 5. Duodenal and ileocecal release profiles are compared separately and in combination to evaluate any benefit of one over the other or synergy in the combination. Further, FIG. 6 shows a clinical study design with the present formulations. Further an evaluation of the pharmacokinetics and breath methane effects of different doses and dosing profiles in methane positive subjects may be undertaken. Such evaluations are optionally of lovastatin diol lactone.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50%" covers the range of 45% to 55%.

An "effective amount," when used in connection with medical uses is an amount that is effective for providing a measurable treatment, prevention, or reduction in the rate of pathogenesis of a disorder of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents (e.g., anti-methanogenic lovastatin analog or derivative and/or additional therapeutic agents described herein) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures, tissue samples, tissue homogenates or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays or measurements or methane production in stool samples. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A method for treating irritable bowel syndrome (IBS) or constipation-associated IBS (IBS-C) in a human subject, comprising:
   administering to the subject a modified-release formulation comprising
   a coating having a pH-dependent erosion profile; and an effective amount of lovastatin diol lactone releasably enclosed within the coating,
   wherein the modified-release formulation releases at least 60% of the lovastatin diol lactone into the small and/or large intestine of the subject,
   wherein the modified-release formulation avoids or reduces systemic exposure to lovastatin diol lactone,
   wherein the modified-release formulation reduces or inhibits methanogenesis in the small and/or large intestine, and
   wherein the lovastatin diol lactone does not result in effective inhibition of HMG-CoA reductase in the subject.

2. The method of claim 1, wherein the coating does not release the lovastatin diol lactone at pH of 5 or less and releases the lovastatin diol lactone at a pH greater than 5 in the small and/or large intestine of the subject.

3. The method of claim 2, wherein the coating does not release the lovastatin diol lactone in the stomach and/or small intestine of the subject.

4. The method of claim 1, wherein the modified-release formulation is suitable for oral administration.

5. The method of claim 4, wherein the modified-release formulation is in the form of a capsule or a tablet.

6. The method of claim 1, wherein the coating has a time-dependent erosion profile.

7. A method for treating irritable bowel syndrome (IBS) or constipation-associated IBS (IBS-C) in a human subject, comprising:
   administering an effective amount of a lovastatin diol lactone to a human subject in need thereof,
   wherein the lovastatin diol lactone is in a modified-release formulation comprising a coating having a pH-dependent erosion profile and having the lovastatin diol lactone releasably enclosed therein for release in the gastrointestinal (GI) tract of a human,
   wherein the modified-release formulation releases at least 60% of the lovastatin diol lactone into the small and/or large intestine,
   wherein the administration of the lovastatin diol lactone in the modified-release formulation avoids or reduces systemic exposure to the lovastatin diol lactone,
   wherein the modified-release formulation reduces or inhibits methanogenesis in the small and/or large intestine, and
   wherein the lovastatin diol lactone does not result in effective inhibition of HMG-CoA reductase in the human subject.

8. The method of claim 7, wherein the coating does not release the lovastatin diol lactone at pH of 5 or less and releases the lovastatin diol lactone at a pH greater than 5 in the small and/or large intestine of the subject.

9. The method of claim 8, wherein the coating does not release the lovastatin diol lactone in the stomach and/or small intestine of the subject.

10. The method of claim 7, wherein the modified-release formulation is suitable for oral administration.

11. The method of claim 10, wherein the modified-release formulation is in the form of a capsule or a tablet.

12. The method of claim 7, wherein the coating has a time-dependent erosion profile.

* * * * *